(12) United States Patent
Nishide et al.

(10) Patent No.: US 12,198,258 B2
(45) Date of Patent: Jan. 14, 2025

(54) PROCESSOR FOR ENDOSCOPE, PROGRAM, INFORMATION PROCESSING METHOD, AND INFORMATION PROCESSING DEVICE

(71) Applicant: HOYA CORPORATION, Tokyo (JP)

(72) Inventors: Akihiko Nishide, Tokyo (JP); Kohei Iketani, Saitama (JP); Junko Isawa, Kanagawa (JP)

(73) Assignee: HOYA CORPORATION, Tokyo (JP)

( * ) Notice: Subject to any disclaimer, the term of this patent is extended or adjusted under 35 U.S.C. 154(b) by 404 days.

(21) Appl. No.: 17/436,739

(22) PCT Filed: Sep. 16, 2020

(86) PCT No.: PCT/JP2020/035079
§ 371 (c)(1),
(2) Date: Sep. 7, 2021

(87) PCT Pub. No.: WO2021/054360
PCT Pub. Date: Mar. 25, 2021

(65) Prior Publication Data
US 2022/0198742 A1 Jun. 23, 2022

(30) Foreign Application Priority Data

Sep. 20, 2019 (JP) ................................. 2019-171874
Dec. 9, 2019 (JP) ................................. 2019-222349

(51) Int. Cl.
*A61B 1/00* (2006.01)
*A61B 1/005* (2006.01)
(Continued)

(52) U.S. Cl.
CPC ........ *G06T 15/10* (2013.01); *A61B 1/000095* (2022.02); *A61B 1/000096* (2022.02);
(Continued)

(58) Field of Classification Search
CPC ... A61B 1/005; A61B 1/000095; A61B 6/032; A61B 5/055; A61B 1/000096;
(Continued)

(56) References Cited

U.S. PATENT DOCUMENTS 11,992,178 B2 *  5/2024  Kamon ............... A61B 1/00018
2005/0152588 A1 *  7/2005  Yoshida ................... G06T 15/08
                                                                                600/407
(Continued)

FOREIGN PATENT DOCUMENTS

CN       103298407 A  *  9/2013   ......... A61B 1/00045
CN       110831487 B  *  6/2022   ......... A61B 1/00009
(Continued)

OTHER PUBLICATIONS

Interanational Search Report issued in International Bureau of WIPO Patent Application No. PCT/JP2020/035079, dated Dec. 1, 2020, along with an English translation thereof.
(Continued)

*Primary Examiner* — Chante E Harrison
(74) *Attorney, Agent, or Firm* — GREENBLUM & BERNSTEIN, P.L.C.

(57) ABSTRACT

A processor for an endoscope includes: an endoscopic image acquisition unit that acquires an endoscopic image of a patient from the endoscope; a virtual endoscopic image acquisition unit that acquires a virtual endoscopic image reconstructed on the basis of a three-dimensional medical image obtained by capturing an image of the patient in advance; a virtual endoscopic image reconstruction unit that reconstructs a corrected virtual endoscopic image that matches most with the endoscopic image on the basis of the degree of matching between the virtual endoscopic image and the endoscopic image; and a diagnosis support information output unit that outputs diagnosis support informa-
(Continued)

tion based on a feature parameter corrected according to a correspondence between each pixel of the endoscopic image and a distance image obtained from the corrected virtual endoscopic image.

10 Claims, 37 Drawing Sheets

(51) Int. Cl.
*A61B 6/03* (2006.01)
*A61B 6/40* (2024.01)
*G06F 18/22* (2023.01)
*G06T 5/50* (2006.01)
*G06T 7/00* (2017.01)
*G06T 7/70* (2017.01)
*G06T 15/10* (2011.01)

(52) U.S. Cl.
CPC .......... *A61B 1/00193* (2013.01); *A61B 1/005* (2013.01); *A61B 6/032* (2013.01); *A61B 6/4085* (2013.01); *G06F 18/22* (2023.01); *G06T 5/50* (2013.01); *G06T 7/0012* (2013.01); *G06T 7/70* (2017.01); *G06T 2207/10068* (2013.01); *G06T 2207/30004* (2013.01)

(58) Field of Classification Search
CPC ........ G06F 18/22; G06T 5/50; G06T 7/0012; G06T 7/62; G06T 7/70; G06T 7/75; G06T 2207/10068; G06T 2207/10081; G06T 2207/10088; G06T 2207/30004; G06T 15/10; G06V 10/751; G06V 2201/03

See application file for complete search history.

(56) References Cited

U.S. PATENT DOCUMENTS

| | | |
|---|---|---|
| 2013/0018255 A1 | 1/2013 | Kitamura et al. |
| 2014/0081079 A1 | 3/2014 | Kawasaki et al. |
| 2018/0160990 A1 | 6/2018 | Weingarten et al. |

FOREIGN PATENT DOCUMENTS

| | | | | |
|---|---|---|---|---|
| JP | 2000-148983 | | 5/2000 | |
| JP | 2002-238887 | | 8/2002 | |
| JP | 2003-265408 | | 9/2003 | |
| JP | 2011-000173 | | 1/2011 | |
| JP | 2011-212245 | | 10/2011 | |
| JP | 2013-009956 | | 1/2013 | |
| JP | 2016-039874 | | 3/2016 | |
| JP | 2016-077727 | | 5/2016 | |
| JP | 2016518148 A | * | 6/2016 | |
| JP | 2019-136508 | | 8/2019 | |
| JP | 2020014711 A | * | 1/2020 | ......... A61B 1/00009 |
| JP | 2023003728 A | * | 1/2023 | ............. A61B 1/045 |
| WO | WO-2005077272 A1 | * | 8/2005 | ......... A61B 1/00009 |
| WO | WO-2011122032 A1 | * | 10/2011 | ......... A61B 1/00009 |
| WO | WO-2014011925 A2 | * | 1/2014 | ............. A61B 5/055 |
| WO | WO-2018002935 A1 | * | 1/2018 | ......... A61B 1/00009 |
| WO | WO-2020066807 A1 | * | 4/2020 | ......... A61B 1/00004 |
| WO | WO-2021054360 A1 | * | 3/2021 | ....... A61B 1/000095 |

OTHER PUBLICATIONS

Apr. 18, 2023 Chinese Office Action in corresponding Chinese Application No. 202080019466.X.

* cited by examiner

| PATIENT ID | SEX | NAME | THREE-DIMENSIONAL MEDICAL IMAGE | 471 |
|---|---|---|---|---|
| 0000001 | MALE | *** | ****** | |

FIG. 7
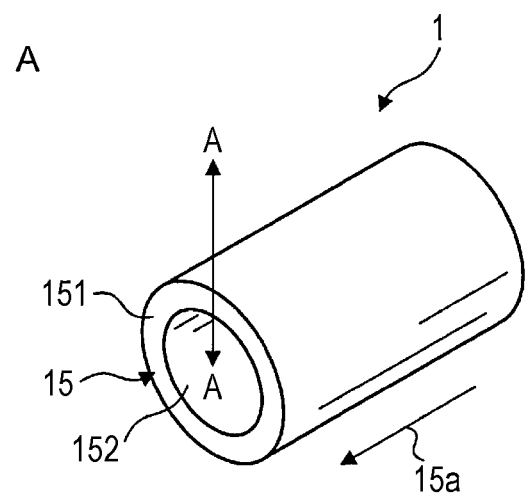
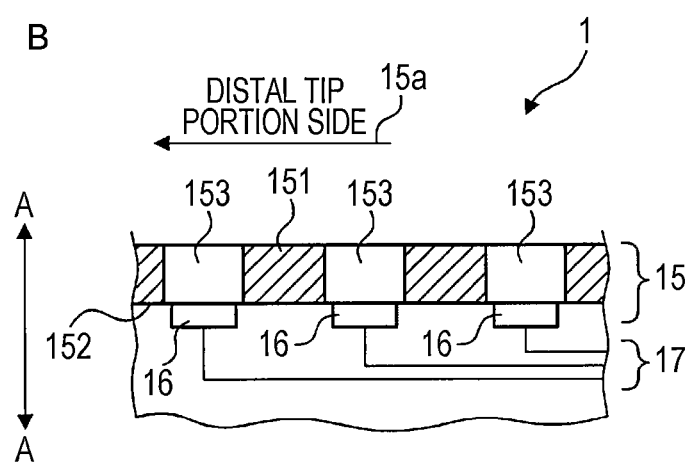

| MANAGEMENT ID | PATIENT ID | DIAGNOSIS CONTENT | DIAGNOSIS DATE AND TIME |
|---|---|---|---|
| 00001 | 0000001 | ****** | ****** |

PROCESSOR FOR ENDOSCOPE, PROGRAM, INFORMATION PROCESSING METHOD, AND INFORMATION PROCESSING DEVICE

TECHNICAL FIELD

The present invention relates to a processor for an endoscope, a program, an information processing method, an information processing method, and an information processing device.

The present application claims priority based on Japanese Patent Application No. 2019-171874 filed on Sep. 20, 2019 and Japanese Patent Application No. 2019-222349 filed on Dec. 9, 2019, the entire contents of which are incorporated herein by reference.

BACKGROUND ART

The majority of tumor examinations of patients is conducted by inserting an endoscope into a tubular organ site such as the trachea, the bronchus, the upper digestive tract, the pancreas, the biliary tract, or the intestinal tract, in particular, and by using an image obtained by the inserted endoscope. However, in two-dimensional image information of the endoscopic image, a distance to each pixel is not known, there is also geometric distortion of the image, and an error at the time of image measurement is large. Therefore, it is inappropriate to provide, as image diagnosis support information, the endoscopic image as it is. A virtual endoscope disclosed in Patent Literature 1 can provide a virtual endoscopic image using data of an X-ray computed tomography (CT) image. The virtual endoscopic image is created from a three-dimensional image of an X-ray CT, and in a case where an endoscopic image and the virtual endoscopic image are associated with each other, information on a distance to each pixel of the endoscopic image can also be known from the three-dimensional image of the X-ray CT. Therefore, there is a possibility that accuracy in image measurement can be improved and accuracy of the image diagnosis support information can also be improved.

The majority of tumor examinations of patients is conducted by inserting an endoscope into a tubular organ site such as the trachea, the bronchus, the upper digestive tract, the pancreas, the biliary tract, or the intestinal tract, in particular, and by using an image obtained by the inserted endoscope. However, in two-dimensional image information of the endoscopic image, a distance to each pixel is not known, there is also geometric distortion of the image, and an error at the time of image measurement is large. Therefore, it is difficult to provide, as image diagnosis support information, the endoscopic image as it is. On the other hand, the virtual endoscope disclosed in Patent Literature 1 provides a virtual endoscopic image using data of an X-ray computed tomography (CT) image. The virtual endoscopic image is created from a three-dimensional image of the X-ray CT.

CITATION LIST

Patent Literature

Patent Literature 1: JP 2002-238887 A

SUMMARY OF INVENTION

Technical Problem

However, the invention according to Patent Literature 1 has a problem that only a cross-sectional reconstructed image (virtual endoscopic image) of the X-ray CT is displayed, and diagnosis using the endoscopic image and the virtual endoscopic image in combination is not considered. In addition, the virtual endoscope disclosed in Patent Literature 1 simply displays a cross-sectional reconstructed image (virtual endoscopic image) of the X-ray CT, and no consideration is given to associating the endoscopic image with the three-dimensional image obtained by the X-ray CT in performing diagnosis support.

In one aspect, an object is to provide a processor for an endoscope and the like that can be effectively used for diagnosis.

Solution to Problem

A processor for an endoscope according to one aspect includes: an endoscopic image acquisition unit that acquires an endoscopic image of a patient from the endoscope; a virtual endoscopic image acquisition unit that acquires a virtual endoscopic image reconstructed on the basis of a three-dimensional medical image obtained by capturing an image of the patient in advance; a virtual endoscopic image reconstruction unit that reconstructs a corrected virtual endoscopic image that matches most with the endoscopic image on the basis of the degree of matching between the virtual endoscopic image acquired by the virtual endoscopic image acquisition unit and the endoscopic image acquired by the endoscopic image acquisition unit; and a diagnosis support information output unit that outputs diagnosis support information based on a feature parameter corrected according to a correspondence between each pixel of the endoscopic image acquired by the endoscopic image acquisition unit and a distance image obtained from the corrected virtual endoscopic image reconstructed by the virtual endoscopic image reconstruction unit.

A program according to one aspect of the present disclosure causes a computer to perform processing of: acquiring an endoscopic image obtained in a manner in which an endoscope captures an image of a subject; acquiring a three-dimensional medical image obtained in a manner in which an image of the inside of the body of the subject is captured by at least one of an X-ray CT scan, an X-ray cone beam CT scan, or an MRI-CT scan; deriving position information in a coordinate system of the three-dimensional medical image specified by the endoscopic image and the three-dimensional medical image; and storing the endoscopic image and the three-dimensional medical image in association with each other on the basis of the derived position information.

An information processing method according to one aspect of the present disclosure causes a computer to perform processing of: acquiring an endoscopic image obtained in a manner in which an endoscope captures an image of a subject; acquiring a three-dimensional medical image obtained in a manner in which an image of the inside of the body of the subject is captured by at least one of an X-ray CT scan, an X-ray cone beam CT scan, or an MRI-CT scan; deriving position information in a coordinate system of the three-dimensional medical image specified by the endoscopic image and the three-dimensional medical image; and storing the endoscopic image and the three-dimensional medical image in association with each other on the basis of the derived position information.

An information processing device according to one aspect of the present disclosure includes: an acquisition unit that acquires an endoscopic image obtained in a manner in which an endoscope captures an image of a subject, and a three-dimensional medical image obtained in a manner in which an image of the inside of the body of the subject is captured by at least one of an X-ray CT scan, an X-ray cone beam CT scan, or an MRI-CT scan; a deriving unit that derives position information in a coordinate system of the three-dimensional medical image specified by the endoscopic image and the three-dimensional medical image; and a storing unit that stores the endoscopic image and the three-dimensional medical image in association with each other on the basis of the derived position information.

Advantageous Effects of Invention

In one aspect, an object is to provide a processor for an endoscope and the like that can be effectively used for diagnosis.

BRIEF DESCRIPTION OF DRAWINGS

FIG. 7 is a configuration diagram in a case where an optical sensor is disposed in a flexible tube.

DESCRIPTION OF EMBODIMENTS

Hereinafter, the present invention will be described in detail with reference to the drawings illustrating the embodiments thereof.

First Embodiment

A first embodiment is an embodiment in which an endoscopic image acquired from an endoscope is output in association with a virtual endoscopic image corresponding to a distance by which the endoscope is inserted into a body. The virtual endoscopic image is a virtual endoscopic image of the inside of a body cavity based on a three-dimensional image, which is reconstructed on the basis of a three-dimensional medical image obtained by an X-ray CT scan, MRI scan, or X-ray cone beam CT scan in which an image of the inside of trachea, the inside of the bronchus, or a tubular organ such as the intestinal tract is captured.

Examples of the three-dimensional medical image include an image represented by volume data reconstructed from slice data output from a CT device, a magnetic resonance imaging (MRI) device, or the like, and an image represented by volume data output from an X-ray cone beam CT device using a multi slice (MS) CT device and an X-ray flat panel. For example, the virtual endoscopic image of the large intestine may be reconstructed by performing CT scanning in a state where air is introduced into the large intestine and performing volume rendering of a three-dimensional image obtained by the scanning from the inner side of the large intestine.

Figure 1:
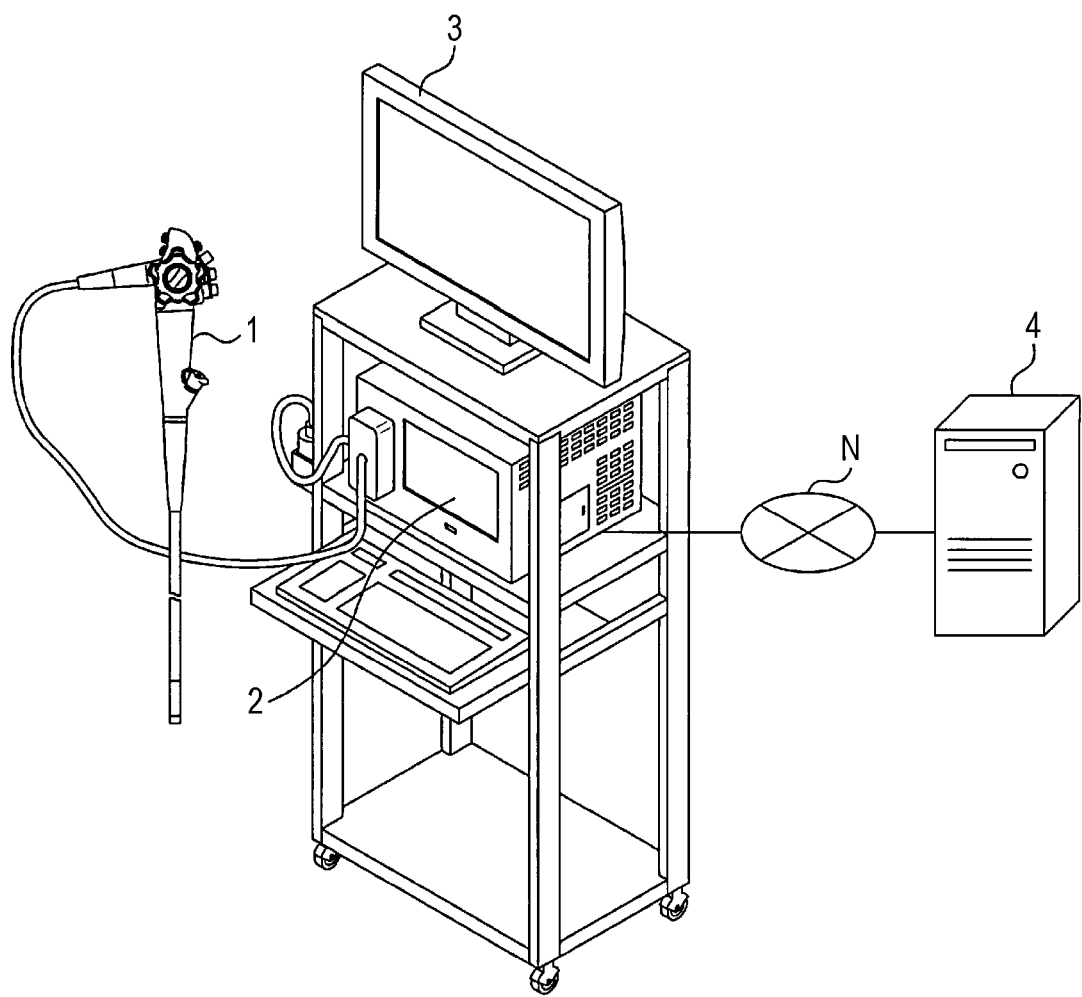
FIG. 1 is a schematic diagram illustrating a configuration example of an endoscope system.

FIG. 1 is a schematic diagram illustrating a configuration example of an endoscope system. The system illustrated in FIG. 1 includes an endoscope 1 which is inserted into a body of a subject to capture an image and outputs a video signal of an observation target, a processor 2 for an endoscope which converts the video signal output by the endoscope 1 into an endoscopic image, a display device 3 which displays the endoscopic image and the like, and an information processing device 4. The endoscope 1, the processor 2 for an endoscope, and the display device 3 transmit and receive an electric signal, a video signal, and the like via a connector. The processor 2 for an endoscope and the information processing device 4 transmit and receive information via a network N such as the Internet.

The endoscope 1 is an instrument whose insertion portion having an image sensor provided at a distal tip portion is inserted into the body of the subject to perform diagnosis or treatment. The endoscope 1 transfers, to the processor 2, a captured image taken by the image sensor provided at the distal tip.

The processor 2 for an endoscope is an information processing device that performs image processing on the captured image acquired from the image sensor provided at the distal tip of the endoscope 1, collects an endoscopic image, and outputs the endoscopic image to the display device 3. Hereinafter, for the sake of brevity, the processor 2 for an endoscope will be referred to as the processor 2.

The display device 3 is a liquid crystal display, an organic electroluminescence (EL) display, or the like, and displays the endoscopic image or the like output from the processor 2.

The information processing device 4 is an information processing device that stores and transmits/receives information regarding a patient and a virtual endoscopic image reconstructed on the basis of a three-dimensional medical image obtained by capturing an image of the patient. The information processing device 4 is, for example, a server device, a personal computer, or the like. In the present embodiment, the information processing device 4 is assumed to be a server device, and is hereinafter referred to as a server 4 for brevity.

Figure 2:
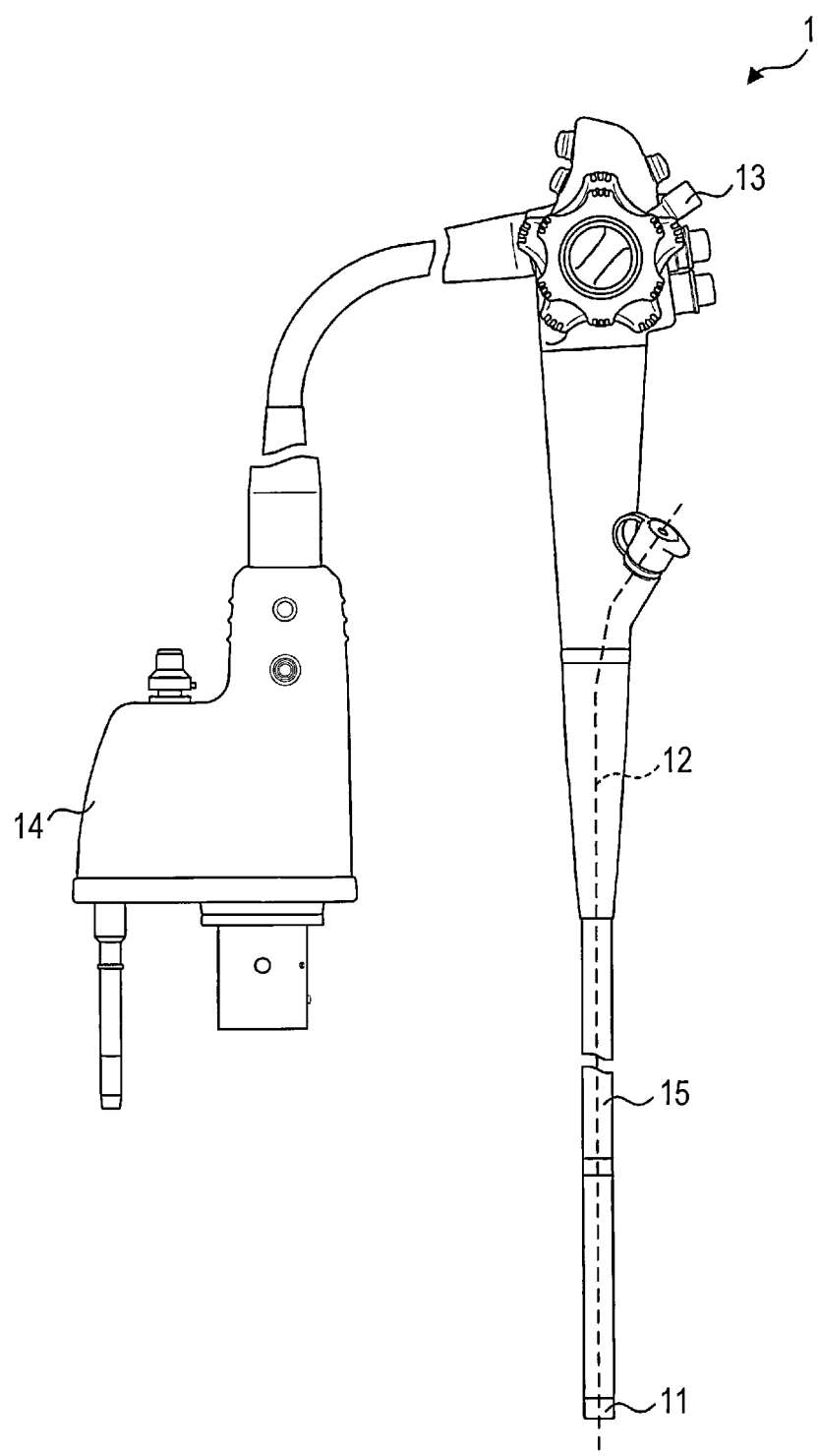
FIG. 2 is an exterior view of an endoscope.

FIG. 2 is an exterior view of the endoscope 1. The endoscope 1 includes an image sensor 11, a treatment tool insertion channel 12, an operation unit 13, a connector 14, and a flexible tube 15. The image sensor 11 is, for example, a charge coupled device (CCD) image sensor, a charge modulation device (CMD) image sensor, or a complementary metal oxide semiconductor (CMOS) image sensor installed at the distal tip portion of the endoscope 1, and performs photoelectrical transformation on incident light. An electric signal reconstructed by the photoelectric transformation is subjected to signal processing such as A/D conversion and noise removal by a signal processing circuit (not illustrated), and is output to the processor 2.

The treatment tool insertion channel 12 is a channel for passing a treatment tool. Examples of the treatment tool include a gripper, a biopsy needle, forceps, a snare, a clamp, scissors, a scalpel, incision instrument, an endoscopic stapler, a tissue loop, a clip plier, suture delivery instrument, energy-based tissue clotting instrument, and tissue cutting instrument. The operation unit 13 is provided with a release button, an angle knob for bending the distal tip of the endoscope, and the like, and receives a signal for instructing an operation of a peripheral device such as air supply, water supply, and gas supply. The connector 14 is connected to the processor 2. The flexible tube 15 is a flexible endoscope conduit that can be inserted into the body of a patient.

Figure 3:
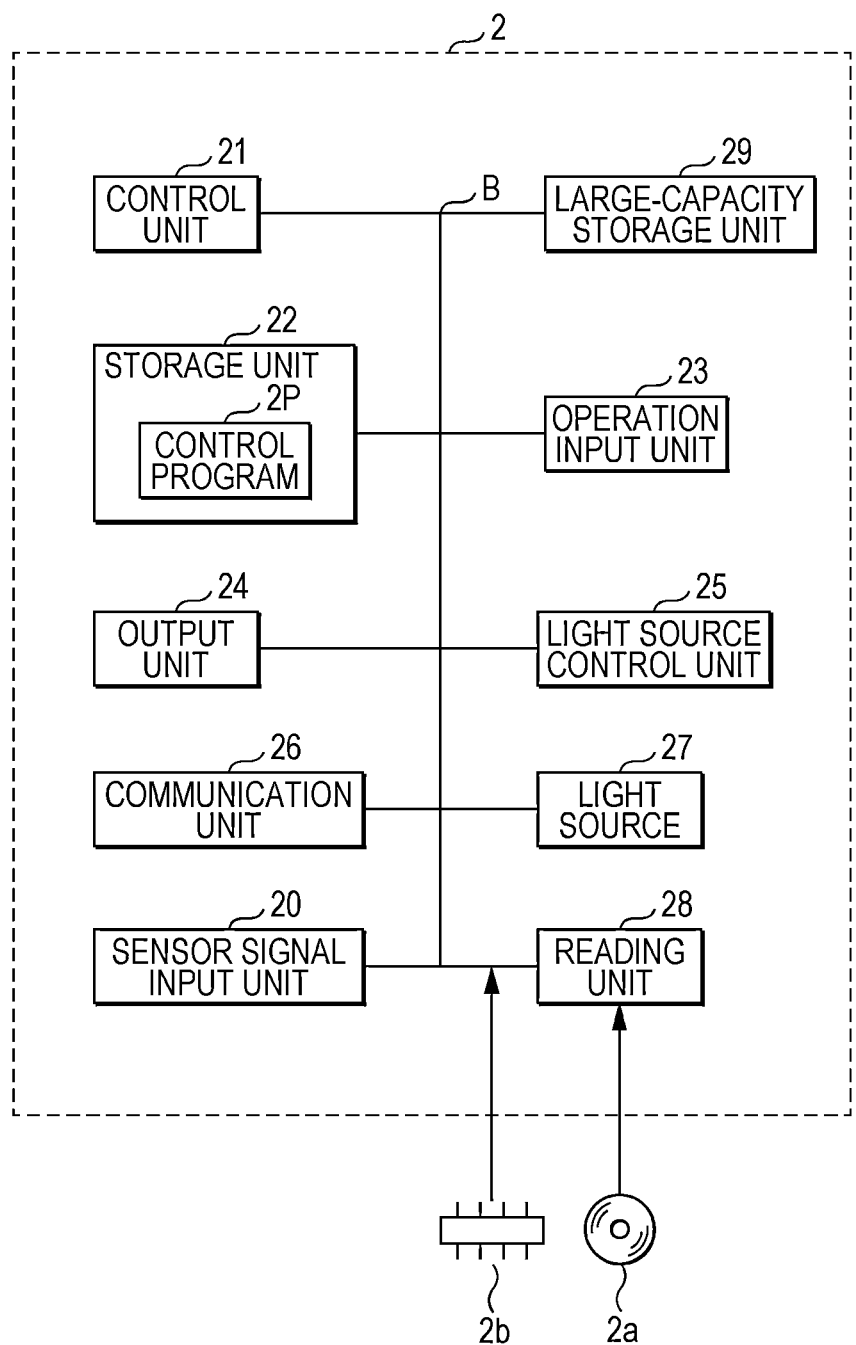
FIG. 3 is a block diagram illustrating a configuration example of a processor.

FIG. 3 is a block diagram illustrating a configuration example of the processor 2. The processor 2 includes a control unit 21, a storage unit 22, an operation input unit 23, an output unit 24, a light source control unit 25, a communication unit 26, a light source 27, a reading unit 28, a large-capacity storage unit 29, and a sensor signal input unit 20. The respective components are connected by a bus B.

The control unit 21 includes arithmetic processing devices such as a central processing unit (CPU), a micro-processing unit (MPU), and a graphics processing unit (GPU), and reads and executes a control program 2P stored in the storage unit 22 to perform various types of information processing, control processing, and the like related to the processor 2. Note that, although the control unit 21 is described as a single processor in FIG. 3, it may be a multiprocessor.

The storage unit 22 includes a memory element such as a random access memory (RAM) or a read only memory (ROM), and stores the control program 2P or data necessary for the control unit 21 to perform processing. In addition, the storage unit 22 temporarily stores data and the like necessary for the control unit 21 to perform arithmetic processing. The operation input unit 23 is implemented by input devices such as a touch panel and various switches, and inputs an input signal generated in response to an external operation performed on these input devices to the control unit 21. Under the control of the control unit 21, the output unit 24 outputs an image signal for display and various types of information to the display device 3 to display the image and information.

The light source control unit 25 controls the quantity of emitted illumination light by turning on/off an LED and the like and by adjusting a drive current and a drive voltage of the LED and the like. Further, the light source control unit 25 controls a wavelength band of the illumination light by changing an optical filter or the like. The light source control unit 25 adjusts an emission timing, an emission period, the quantity, and a spectral spectrum of the illumination light by independently controlling the turning-on or off of each LED and the quantity of emitted light when each LED is turned on. The communication unit 26 is a communication module for performing processing related to communication, and transmits/receives information to/from the server 4, an external information processing device, or the like via the network N.

The light source 27 includes a light source that emits illumination light used for illuminating the observation target. Examples of the light source include a semiconductor light source such as a multi-color light emitting diode (LED) with different wavelength ranges, a combination of a laser diode and a phosphor, a xenon lamp, and a halogen lamp. The light source 27 adjusts brightness and the like under the control of the light source control unit 25 of the processor 2. Note that, in the present embodiment, the processor 2 is integrated with the light source, but the present invention is not limited thereto. For example, the processor 2 may be separate from the light source device.

The reading unit 28 reads a portable storage medium 2*a* including a compact disc (CD)-ROM or a digital versatile disc (DVD)-ROM. The control unit 21 may read the control program 2P from the portable storage medium 2*a* via the reading unit 28 and store the control program 2P in the large-capacity storage unit 29. Further, the control unit 21 may download the control program 2P from another computer via the network N or the like and store the control program 2P in the large-capacity storage unit 29. Furthermore, the control unit 21 may read the control program 2P from a semiconductor memory 2*b*.

The large-capacity storage unit 29 includes, for example, a recording medium such as a hard disk drive (HDD) or a solid state drive (SSD). Note that, in the present embodiment, the storage unit 22 and the large-capacity storage unit 29 may be implemented as an integrated storage device. Further, the large-capacity storage unit 29 may be implemented by a plurality of storage devices. Furthermore, the large-capacity storage unit 29 may be an external storage device connected to the processor 2. The sensor signal input unit 20 receives signals obtained from various sensors.

Figures 4, 5:
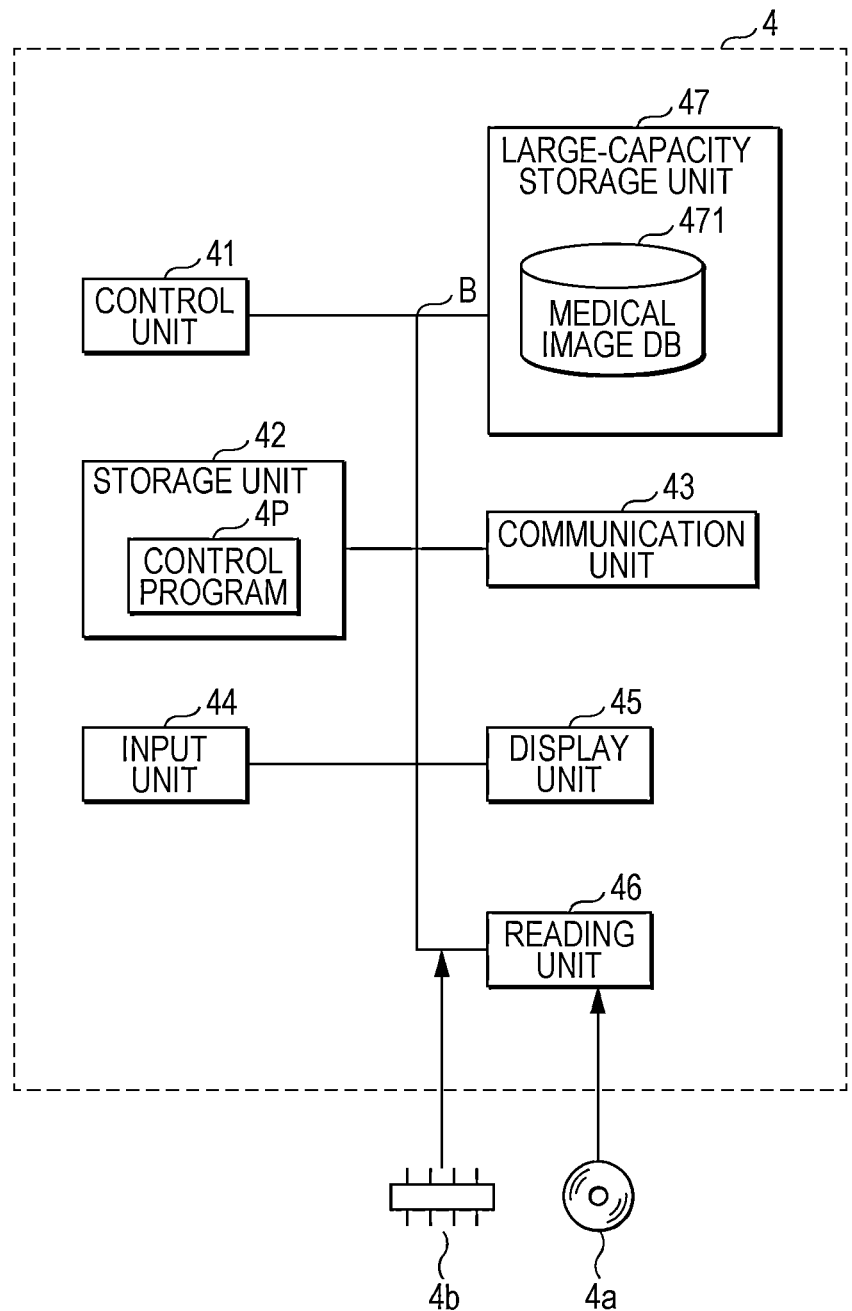
FIG. 4 is a block diagram illustrating a configuration example of a server.
FIG. 5 is an explanatory diagram illustrating an example of a record layout of a medical image DB.

FIG. 4 is a block diagram illustrating a configuration example of the server 4. The server 4 includes a control unit 41, a storage unit 42, a communication unit 43, an input unit 44, a display unit 45, a reading unit 46, and a large-capacity storage unit 47. The respective components are connected by a bus B.

The control unit 41 includes an arithmetic processing device such as a CPU, an MPU, or a GPU, and performs various types of information processing, control processing, and the like related to the server 4 by reading and executing a control program 4P stored in the storage unit 42. Note that, although the control unit 41 is described as a single processor in FIG. 4, it may be a multiprocessor.

The storage unit 42 includes a memory element such as a RAM or a ROM, and stores the control program 4P, data, or the like necessary for the control unit 41 to perform processing. In addition, the storage unit 42 temporarily stores data and the like necessary for the control unit 41 to perform arithmetic processing. The communication unit 43 is a communication module for performing processing related to communication, and transmits/receives information to/from the processor 2 via the network N.

The input unit 44 is an input device such as a mouse, a keyboard, a touch panel, or a button, and outputs received operation information to the control unit 41. The display unit 45 is a liquid crystal display, an organic electroluminescence (EL) display, or the like, and displays various types of information according to an instruction from the control unit 41.

The reading unit 46 reads a portable storage medium 4*a* including a compact disc (CD)-ROM or a digital versatile disc (DVD)-ROM. The control unit 41 may read the control program 4P from the portable storage medium 4*a* via the reading unit 46 and store the control program 4P in the large-capacity storage unit 47. Further, the control unit 41 may download the control program 4P from another computer via the network N or the like and store the control program 4P in the large-capacity storage unit 47. Furthermore, the control unit 41 may read the control program 4P from a semiconductor memory 4*b*.

The large-capacity storage unit 47 includes a recording medium such as an HDD or an SSD. The large-capacity storage unit 47 stores a medical image database (DB) 471. Note that, in the present embodiment, the storage unit 42 and the large-capacity storage unit 47 may be implemented as an integrated storage device. Further, the large-capacity storage unit 47 may be implemented by a plurality of storage devices. Furthermore, the large-capacity storage unit 47 may be an external storage device connected to the server 4.

Note that, in the present embodiment, the server 4 is described as one information processing device. However, the server 4 may be implemented by a plurality of devices in a distributed manner or may be implemented by a virtual machine.

FIG. 5 is an explanatory diagram illustrating an example of a record layout of the medical image DB 471. The medical image DB 471 includes a patient ID column, a sex column, a name column, and a three-dimensional medical image column. The patient ID column stores a patient ID uniquely specified to identify each patient. The sex column stores the sex of the patient. The name column stores the name of the patient. The three-dimensional medical image column stores a three-dimensional medical image obtained by capturing an image of the patient. The three-dimensional medical image column may store, for example, a three-dimensional medical image in a digital imaging and communication in medicine (DICOM) format. Note that an endoscopic image and diagnosis support information associated with the three-dimensional medical image may be stored in the medical image DB 471.

Figure 6:
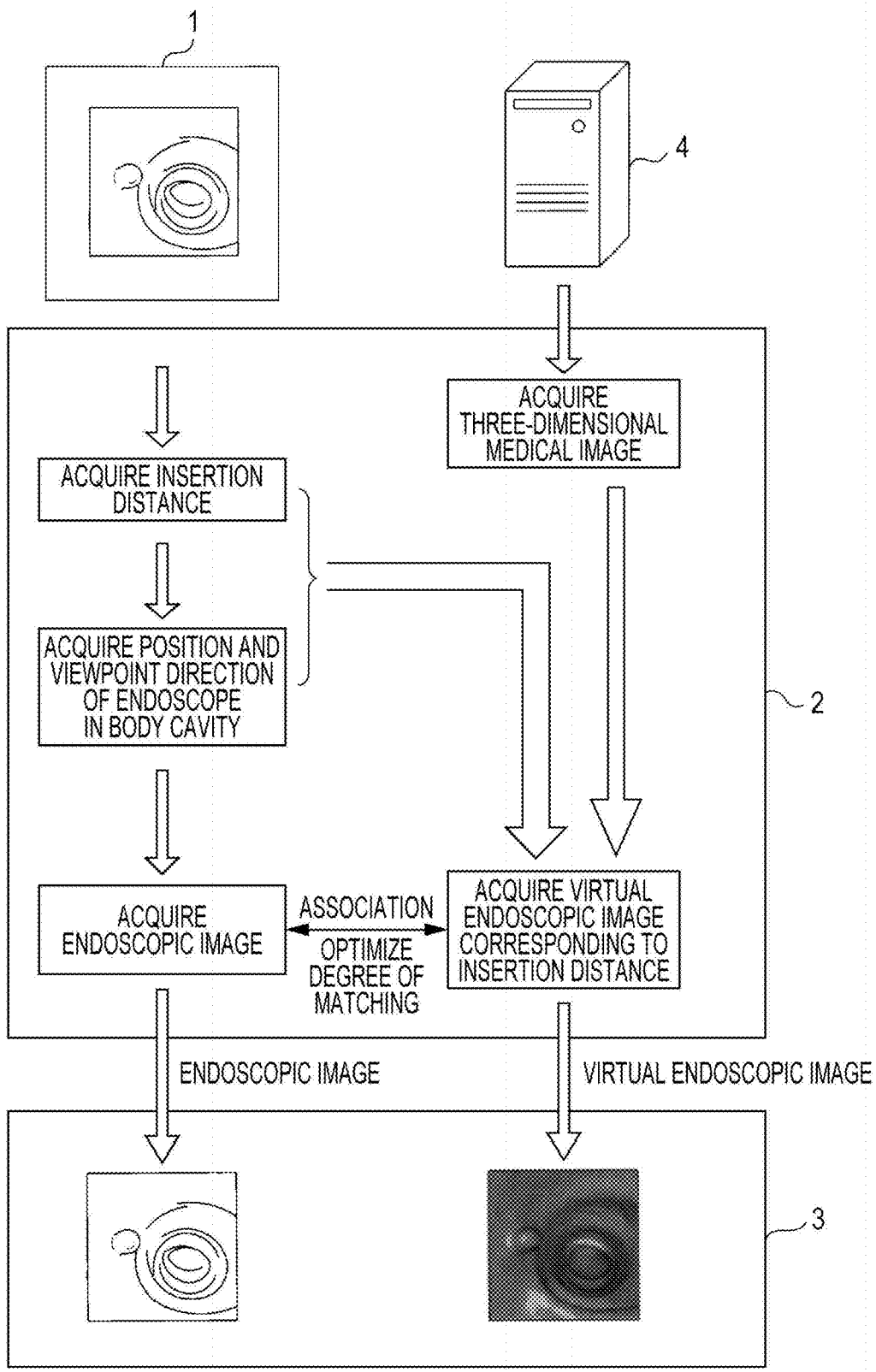
FIG. 6 is an explanatory diagram for describing processing of outputting an endoscopic image in association with a virtual endoscopic image.

FIG. 6 is an explanatory diagram illustrating processing of outputting the endoscopic image in association with the virtual endoscopic image. The control unit 41 of the server 4 acquires a three-dimensional medical image obtained by capturing an image of the patient in advance before surgery, before examination, or the like from the medical image DB 471 of the large-capacity storage unit 47. The control unit 41 transmits the acquired three-dimensional medical image to the processor 2 via the communication unit 43. The control unit 21 of the processor 2 receives the three-dimensional medical image transmitted from the server 4 via the communication unit 26.

The control unit 21 reconstructs a virtual endoscopic image on the basis of the received three-dimensional medical image. Hereinafter, an example of reconstructing a virtual endoscopic image of the large intestine by using a three-dimensional medical image of the large intestine will be described. Note that the three-dimensional medical image is not limited to the three-dimensional medical image of the large intestine, and may be a three-dimensional medical image of another hollow organ such as the bronchus or the stomach.

The control unit 21 extracts voxel data of an organ in the subject from the acquired three-dimensional medical image. The organ is, for example, the large intestine, the small intestine, the kidney, the bronchus, and a blood vessel. However, the organ is not limited thereto and may be other organs. Note that, in the present embodiment, the voxel data of the large intestine is extracted and acquired.

In a method of extracting a large intestine region, specifically, first, processing of reconstructing a plurality of axial images of cross sections perpendicular to a body axis on the basis of the three-dimensional medical image, and separating an extracorporeal region and an intracorporeal region from each other based on a body surface in each axial image by a known method is performed. For example, binarization processing is performed on the reconstructed axial image, a contour is extracted by contour extraction processing, and the inside of the extracted contour is extracted as the intracorporeal (human body) region.

Next, binarization processing using a threshold is performed on the axial image of the intracorporeal region, and a candidate for a region of the large intestine in each axial image is extracted. Specifically, since air is in the tract of the large intestine, a threshold (for example, −600 or less) corresponding to a CT value of air is set and binarization processing is performed, and an air region in the body in each axial image is extracted as the candidate for the region of the large intestine.

Note that an inner wall image of the present embodiment is an image obtained by virtually capturing an image of the lumen of the large intestine with the endoscope. Specifically, the control unit 21 reconstructs, as the virtual endoscopic image, an image obtained by central projection in a manner of projecting voxel data on a plurality of ray directions radially extending around a line-of-sight vector based on a preset viewpoint and line-of-sight direction onto a predetermined projection plane. Note that, as a specific method of the central projection, for example, a known volume rendering method or the like can be used.

Furthermore, the viewpoint of the virtual endoscopic image may be set by automatically or manually specifying a predetermined point on a center line of the large intestine extracted on the basis of voxel data of the lumen of the large intestine on the three-dimensional medical image of the large intestine displayed on the display device 3, for example. As for the line-of-sight direction, the user may manually set an arbitrary direction, or a heading direction of the center line of the large intestine may be set as the line-of-sight direction.

Note that, in the above-described processing, an example of reconstructing the virtual endoscopic image on the basis of the three-dimensional medical image has been described, but the present invention is not limited thereto. For example, the control unit 21 may directly acquire the virtual endoscopic image reconstructed in advance from the server 4.

When the distal tip of the endoscope 1 is inserted into the body of the patient (subject), the control unit 21 of the processor 2 acquires the endoscopic image acquired from the image sensor provided at the distal tip of the endoscope 1. The control unit 21 acquires a distance (length) by which the endoscope 1 is inserted into the body.

As for the processing of acquiring the insertion distance of the endoscope 1, for example, various sensors for measuring an environment around the endoscope 1 are disposed in the flexible tube 15 of the endoscope 1. As these sensors, a temperature sensor, an optical sensor, a pressure sensor, a vibration sensor, a wetting sensor (electrode), a humidity sensor, and the like are used. Hereinafter, a case where the sensor is an optical sensor will be described.

FIG. 7 is a configuration diagram in a case where an optical sensor is disposed in the flexible tube 15. FIG. 7A is a perspective view of the flexible tube 15. A direction indicated by an arrow 15a in FIG. 7A indicates a longitudinal direction of the flexible tube 15. The flexible tube 15 has an outer endoscope surface 151 that comes into contact with the outside of the endoscope 1 and an inner endoscope surface 152.

FIG. 7B illustrates a schematic cross-sectional view taken along line A-A in FIG. 7A. The flexible tube 15 includes a flexible body 153 that transmits light, an optical sensor 16, and an optical sensor cable 17. The optical sensors 16 are disposed on the inner endoscope surface 152 while being in contact with the flexible body 153 at predetermined intervals along the direction of the arrow 15a. Note that, as an alternative to the flexible body 153, the entire flexible tube 15 may be formed of a material having high transmittance. With this configuration, the optical sensor 16 can receive more light as compared with a case of the flexible body 153. Each optical sensor 16 is connected to the optical sensor cable 17, and the optical sensor cable 17 is connected to the sensor signal input unit 20 of the processor 2.

The quantity of light in a treatment room in which an endoscopic examination is performed is kept substantially the same as that in a normal room. On the other hand, the inside of the body is in a dark state unless there is illumination light. The optical sensor 16 is disposed inside the flexible tube 15, but can receive light even when the flexible tube 15 is inserted into the body. Therefore, it is possible to determine that a portion where the optical sensor receives more light is the outside of the body and a portion where the optical sensor receives less light is the inside of the body. Then, the control unit 21 of the processor 2 can calculate a Z coordinate, which is a distance (length) by which the flexible tube 15 is inserted into the body, by specifying the optical sensor 16 that is positioned at a boundary position which is a body cavity insertion portion on the basis of a signal obtained by the optical sensor 16.

In addition, a roller encoder is attached to a mouthpiece (not illustrated) or the like that is in contact with the flexible tube 15, and the roller encoder rotates by the distance by which the flexible tube 15 is inserted into the body, whereby the Z coordinate, which is the distance by which the endoscope 1 is inserted into the body, can be acquired. The roller encoder of the mouthpiece or the like rotates as the flexible tube 15 moves forward and backward, and can measure a length between the distal tip portion of the endoscope 1 inserted into the body and an opening portion communicating with the lumen of the mouth, the nose, or the like, that is, an insertion distance of the flexible tube 15. The roller encoder is electrically connected to the processor 2 and sends the measured distance to the processor 2. Further, an optical encoder may be used instead of the roller encoder.

In addition, in a case where an auxiliary device for measuring the insertion distance of the endoscope 1 is attached to the body cavity insertion portion which is an entrance of the subject, it is possible to acquire the Z coordinate which is the distance by which the endoscope 1 is inserted into the body by measuring a passing distance of the endoscope. The auxiliary device may measure a distance by a scale of a magnetic field such as a linear scale attached to the flexible tube 15 and a linear head attached to the mouthpiece, or may be a mouthpiece of the endoscope 1 to which a roller is attached. Note that, in a case where the endoscope is inserted into the nose, the anus, or the like, an auxiliary device that is provided with a roller and is similar to the mouthpiece may be used.

Furthermore, chips in which the insertion distances are recorded may be embedded in the flexible tube 15 of the endoscope 1 at regular intervals. The processor 2 can acquire the Z coordinate which is the distance by which the endoscope 1 is inserted into the body from Z coordinate information recorded in the chip obtained by the mouthpiece or the like.

Figure 8:
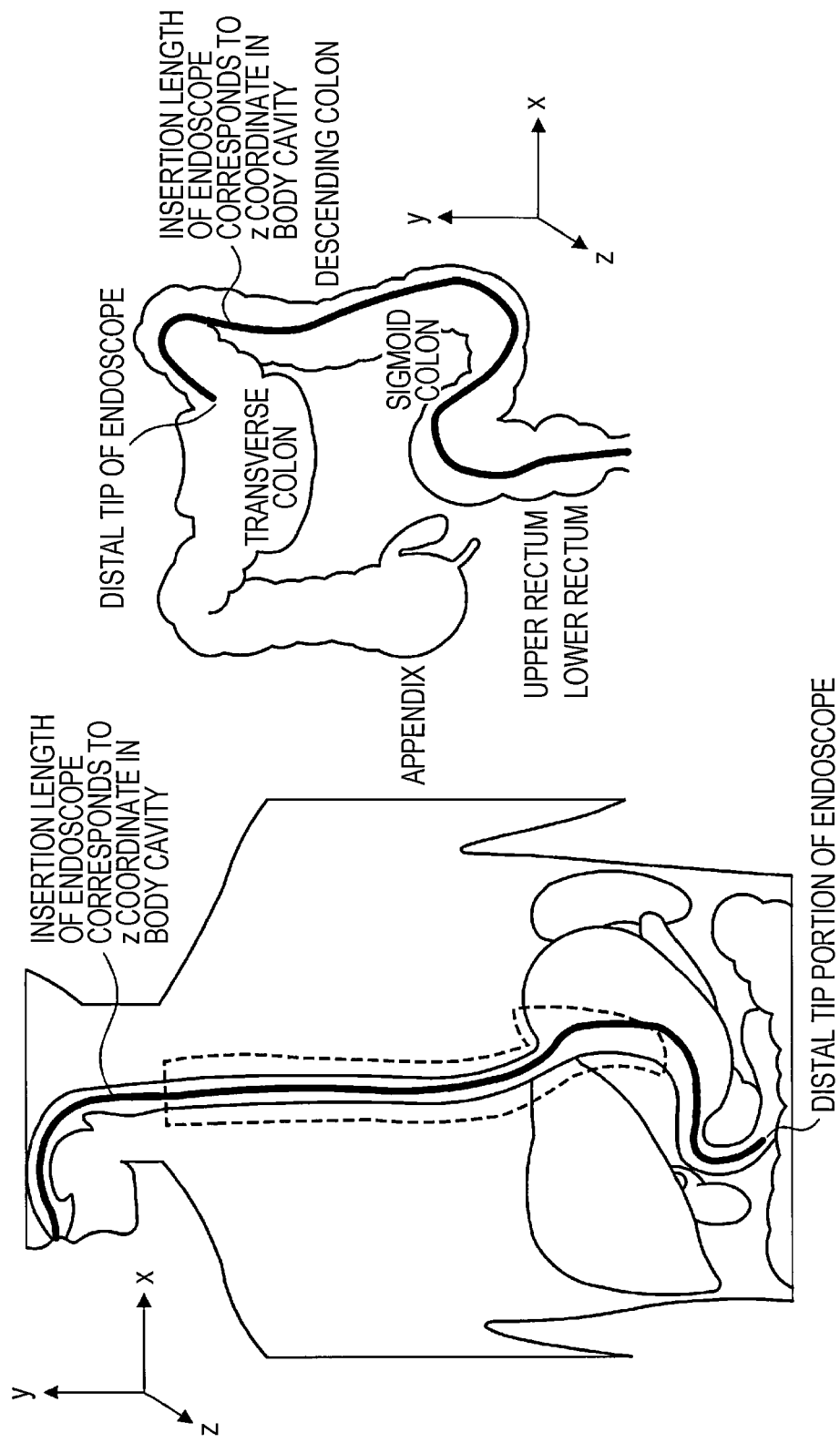
FIG. 8 is an explanatory view illustrating a Z coordinate in a body cavity.

FIG. 8 is an explanatory view illustrating the Z coordinate in the body cavity. The Z coordinate is a distance by which the endoscope 1 is inserted into the body. The control unit 21 of the processor 2 performs processing of converting parameters of a line-of-sight position of the endoscopic image from the length along the body cavity to three-dimensional image coordinates (x, y, z) on the basis of the Z coordinate in the body cavity. The parameters of the line-of-sight position are a position (x, y, z) and angles (θx, θy, θz) which is not illustrated.

Next, referring back to FIG. 6, the control unit 21 reconstructs the virtual endoscopic image corresponding to the Z coordinate which is the insertion distance (length) of the endoscope 1 acquired from the endoscopic image, the position of the endoscope in the body cavity obtained from endoscope bending information, and an endoscope viewpoint direction. Specifically, the control unit 21 acquires the parameters of the line-of-sight position of the endoscopic image acquired from the endoscope 1. The control unit 21 performs processing of converting the parameters of the line-of-sight position of the endoscopic image from the length along the body cavity to the three-dimensional image coordinates (x, y, z) on the basis of the Z coordinate in the body cavity in FIG. 8.

However, the origin of the three-dimensional image is determined to be a certain point of the subject. The parameters of the line-of-sight position are the position (x, y, z) and the angles (θx, θy, θz). The control unit 21 reconstructs the virtual endoscopic image corresponding to the three-dimensional image coordinates after the conversion, the line-of-sight angle, and the insertion distance of the endoscope 1 from the virtual endoscopic image reconstructed by the above-described virtual endoscopic image reconstruction processing. The control unit 21 associates the endoscopic image acquired from the endoscope 1 with the virtual endoscopic image corresponding to the Z coordinate which is the insertion distance of the endoscope 1, and outputs the endoscopic image and the virtual endoscopic image to the display device 3. The display device 3 displays the endoscopic image and the virtual endoscopic image associated with the endoscopic image, the endoscopic image and the virtual endoscopic image being output from the processor 2.

Figure 9:
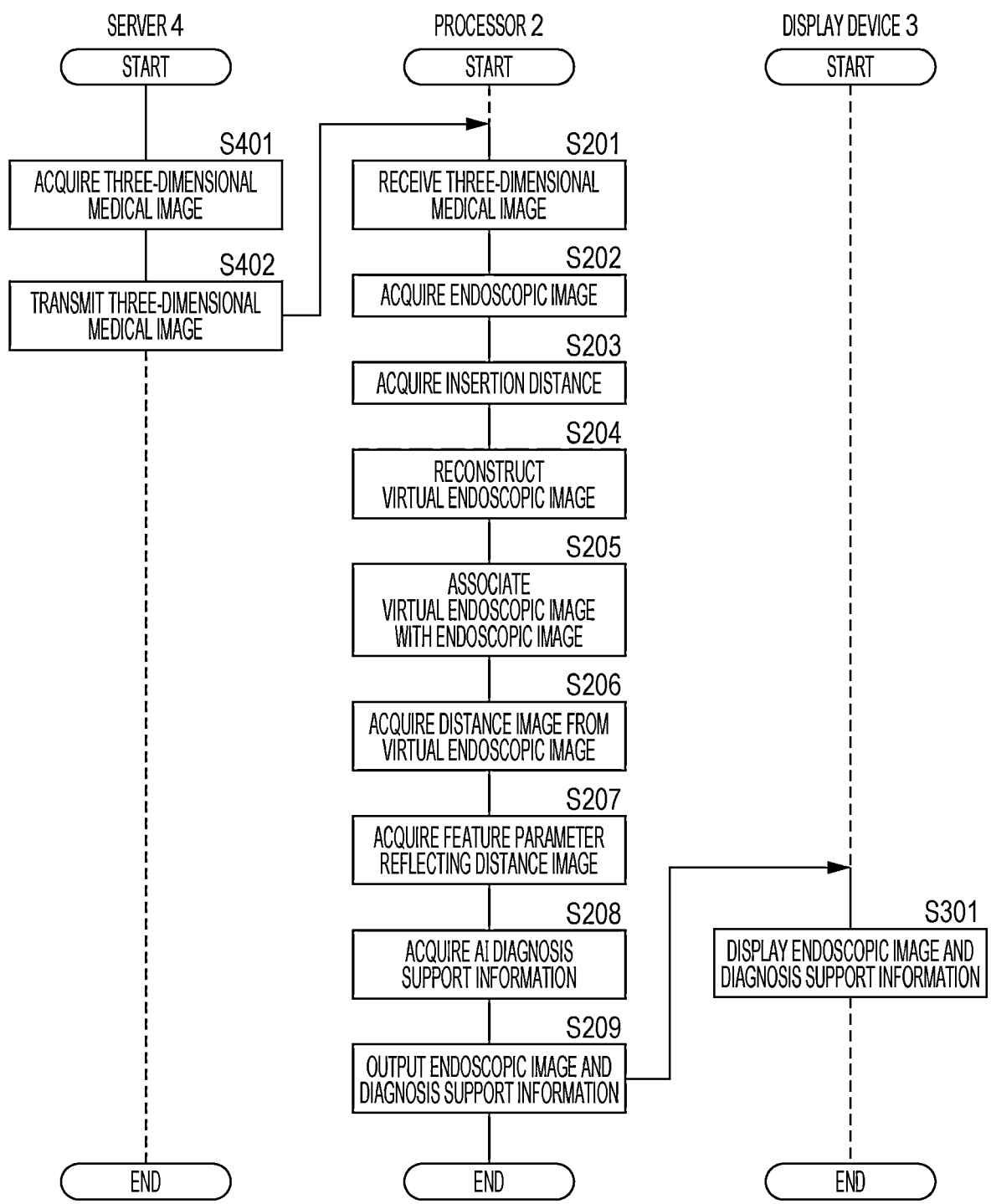
FIG. 9 is a flowchart illustrating a processing procedure when outputting the endoscopic image in association with the virtual endoscopic image.

FIG. 9 is a flowchart illustrating a processing procedure when outputting the endoscopic image in association with the virtual endoscopic image. The control unit 41 of the server 4 acquires a three-dimensional medical image obtained by capturing an image of the patient in advance from the medical image DB 471 of the large-capacity storage unit 47 (Step S401). The control unit 41 transmits the acquired three-dimensional medical image to the processor 2 via the communication unit 43 (Step S402). The control unit 21 of the processor 2 receives the three-dimensional medical image transmitted from the server 4 via the communication unit 26 (Step S201).

The control unit 21 acquires an endoscopic image acquired from the image sensor provided at the distal tip of the endoscope 1 (Step S202). The control unit 21 acquires a Z-coordinate position, which is a distance by which the endoscope 1 is inserted into the body, based on a signal obtained by endoscope insertion distance measurement means (Step S203). Note that a description of the processing of acquiring the Z-coordinate position will be omitted so as not to overlap with the above description.

The control unit 21 reconstructs a virtual endoscopic image on the basis of the received three-dimensional medical image (Step S204). Specifically, the control unit 21 reconstructs, as the virtual endoscopic image, an image obtained by central projection in a manner of projecting voxel data on a plurality of ray directions radially extending around a line-of-sight vector based on a preset viewpoint in the line-of-sight direction onto a predetermined projection plane as in FIG. 18 to be described later, in the lumen of the subject in the acquired three-dimensional medical image. The control unit 21 associates the virtual endoscopic image with the endoscopic image (Step S205). At this time, the viewpoint position and the angle of the endoscope are estimated from the Z-coordinate position (insertion length) and the bending state of the endoscope to reconstruct the virtual endoscopic image, and subtle differences from the endoscopic image are adjusted as below.

The visual field and the line-of-sight direction of the virtual endoscopic image of the observation target are preferably the same as the visual field and the line-of-sight direction of the endoscopic image. The visual field and the line-of-sight direction of the endoscope can be adjusted based on the position and orientation of the endoscopic image. In a case where the position and orientation of the endoscopic image acquired from the endoscope 1 do not match the position and orientation of the virtual endoscopic image corresponding to the insertion distance, the control unit 21 corrects the position and orientation of the virtual endoscopic image on the basis of the endoscopic image and reconstructs the virtual endoscopic image.

In Step S205, a method based on AI may be used to measure the degree of matching between the endoscopic image and the virtual endoscopic image. However, the degree of matching is measured with an index that correlates a shadow image of the endoscopic image and a shadow image of the virtual endoscopic image, and the virtual endoscopic image is continuously reconstructed with the viewpoint position and the angle of the endoscope by finely adjusting the Z-coordinate position (insertion length) and the bending state of the endoscope so as to obtain the highest degree of matching. The endoscopic image and the virtual endoscopic image are caused to match each other. When the endoscopic image and the virtual endoscopic image match each other, the control unit 21 reconstructs the virtual endoscopic image that matches the endoscopic image and acquires a distance image from the virtual endoscopic image (Step S206). The control unit 21 obtains a distance to each pixel of the endoscopic image from the acquired distance image information.

The control unit 21 acquires (obtains) a feature parameter amount obtained by correcting a feature parameter amount obtained from the endoscopic image by image measurement, by using the distance image information (Step S207). The control unit 21 acquires AI diagnosis support information (Step S208). In Step S208, a tumor candidate may be found by AI from the feature parameter amount information obtained by correction using the distance image information described above, a tumor candidate may be found on the basis of determination logic by measuring a feature parameter of each region of the endoscopic image, or a tumor candidate may be found by AI from the feature parameter of each region of the endoscopic image. The tumor candidate information can be provided as image diagnosis support information. As a result, it is possible to provide the image diagnosis support information having higher accuracy than the feature parameter amount information obtained by image measurement in consideration of the distance image information obtained from the virtual endoscopic image that matches the endoscopic image.

The control unit 21 adds the diagnosis support information to the endoscopic image acquired from the endoscope 1 and outputs the endoscopic image added with the diagnosis support information to the display device 3 (Step S209). The display device 3 displays the endoscopic image output from the processor 2 and the diagnosis support information (Step S301), and ends the processing. Note that the associated virtual endoscopic image may also be displayed at this time. In addition, a portion considered to be a tumor candidate may be displayed in a different color or may be highlighted for easy visual recognition.

Next, processing of correcting the position and orientation of the virtual endoscopic image on the basis of the endoscopic image acquired from the endoscope 1 in Steps S203 to 205 will be described.

Specifically, the control unit 21 obtains, as three-dimensional intracorporeal coordinates, a position advanced by the Z coordinate along the body cavity as illustrated in FIG. 8 from the Z-coordinate position of the distal tip portion of the endoscope, the position of the viewpoint, and the direction information acquired from the endoscope 1. The three-dimensional intracorporeal coordinates are determined with a certain position of the subject as the origin. The Z-coordinate position of the distal tip portion of the endoscope is converted into a three-dimensional intracorporeal image, and the virtual endoscopic image and the endoscopic image at the three-dimensional intracorporeal image position are caused to match each other. In order to quantitatively determine the degree of matching between the virtual endoscopic image and the endoscopic image, the degree of matching may be determined on the basis of the degree of correlation of shadow image information obtained from luminance information. Alternatively, the degree of matching may be determined on the basis of similarity between the endoscopic image and the endoscopic image.

Note that the processing method is not limited to the above. For example, the control unit 21 of the processor 2 may adjust the position and orientation of the virtual endoscopic image in a manner in which AI searches for the virtual endoscopic image having high similarity with the endoscopic image. Specifically, when reconstructing the virtual endoscopic image from the three-dimensional image data in the DICOM format, the control unit 21 reconstructs a plurality of virtual endoscopic images at a large number of different line-of-sight positions by forward/backward movement and angle adjustment made by changing six line-of-sight parameters, which are the above-described position (x, y, z) and angles ($\theta x$, $\theta y$, $\theta z$). The control unit 21 compares the similarities between the plurality of reconstructed virtual endoscopic images and the endoscopic image. Here, the similarity comparison between the two images is performed by known image processing, and either pixel data matching or matching of features extracted from the images may be used. The control unit 21 extracts the virtual endoscopic image having the highest similarity with the endoscopic image, and completes the correction processing.

Figure 10:
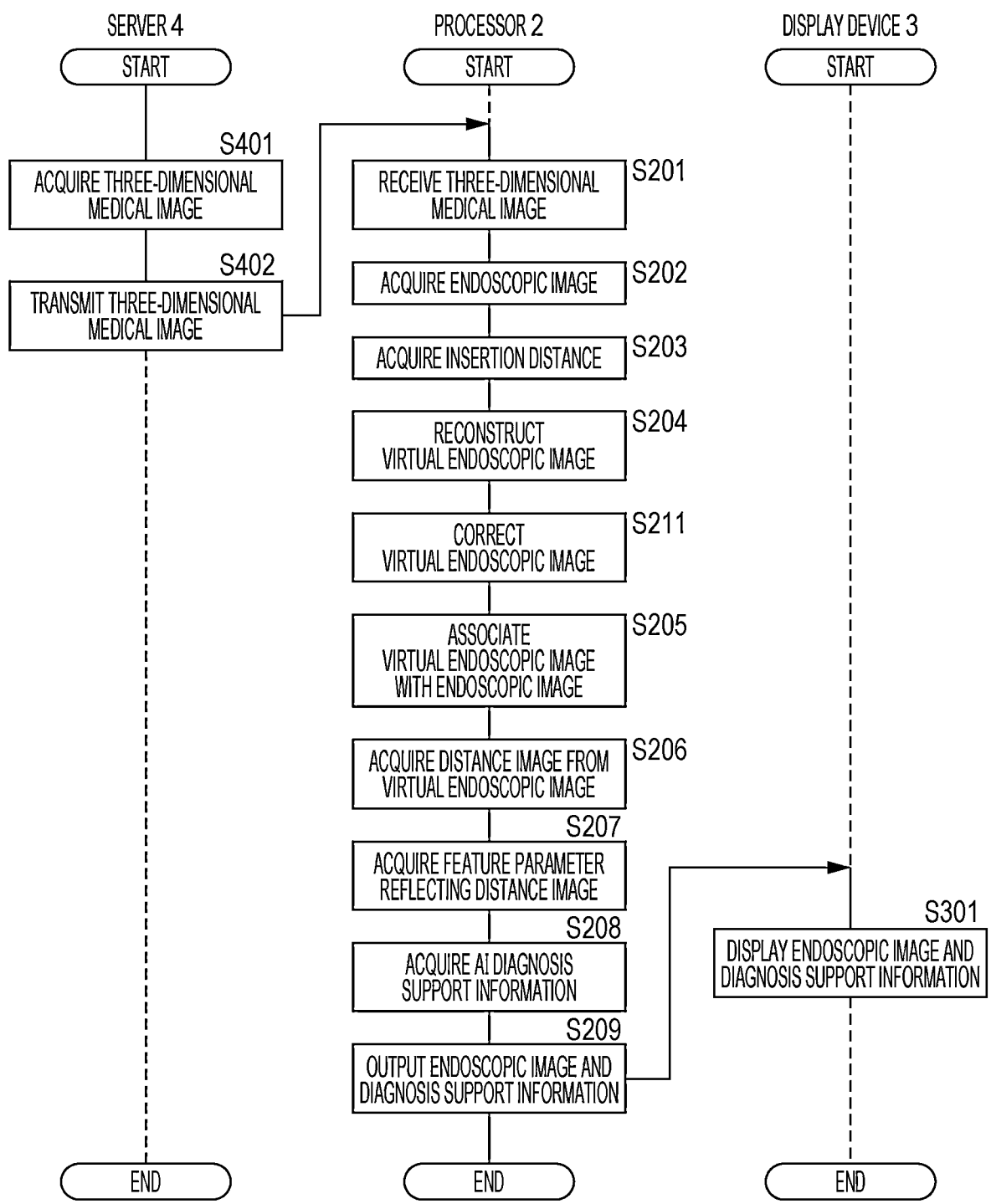
FIG. 10 is a flowchart illustrating a processing procedure when correcting a position and orientation of the virtual endoscopic image.

FIG. 10 is a flowchart illustrating a processing procedure when correcting the position and orientation of the virtual endoscopic image. Note that the contents overlapping with those of FIG. 9 are denoted by the same reference signs and a description thereof will be omitted. After performing Step S204, the control unit 21 of the processor 2 corrects the position and orientation of the virtual endoscopic image on the basis of the endoscopic image acquired from the endoscope 1 (Step S211). Thereafter, the control unit 21 performs Step S205.

Next, processing of correcting the Z coordinate, which is the distance by which the endoscope 1 is inserted into the body, according to bending history information of the endoscope 1 inserted into the body of the patient will be described. For example, in a case where the observation target in the body of the patient is the large intestine, the large intestine is an organ that has a shape and arrangement different for each patient and can be deformed according to the shape of the insertion portion. Therefore, there is a possibility that a detection error of the acquired insertion distance occurs depending on an insertion state of the insertion portion such as the position in the large intestine, the curved shape, and the like. The control unit 21 of the processor 2 acquires the bending history information of the endoscope 1 inserted into the body of the patient, and determines the insertion state of the endoscope 1 according to the acquired bending history information. The control unit 21 corrects the Z coordinate, which is the distance by which the endoscope 1 is inserted into the body, on the basis of the determined insertion state.

Figure 11:
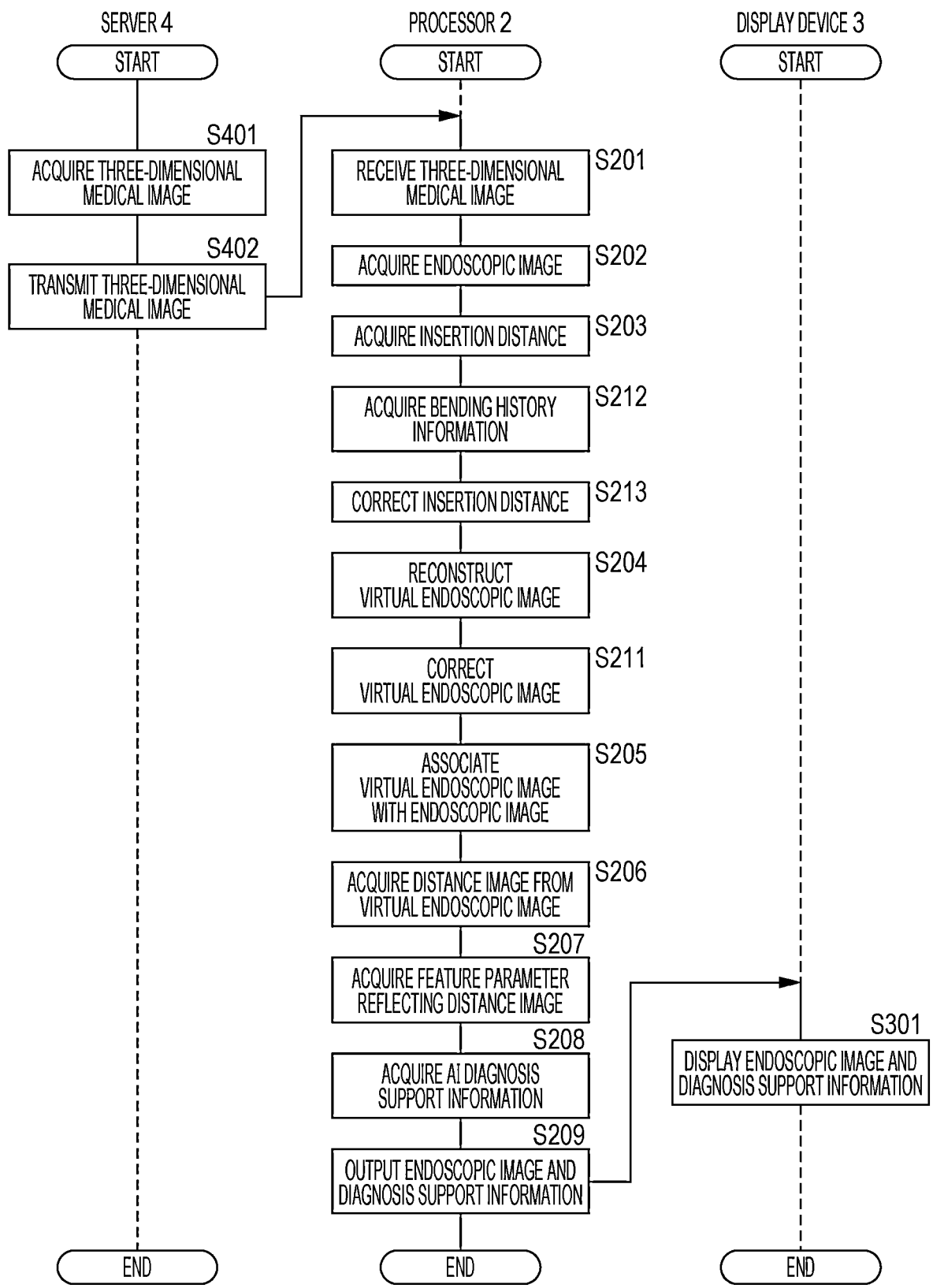
FIG. 11 is a flowchart illustrating a processing procedure when correcting an insertion distance according to bending history information.

FIG. 11 is a flowchart illustrating a processing procedure when correcting the insertion distance according to the bending history information. Note that the contents overlapping with those of FIG. 10 are denoted by the same reference signs and a description thereof will be omitted. After performing Step S203, the control unit 21 of the processor 2 acquires the bending history information (Step S212). For example, the bending history information may be detected by using an endoscope insertion shape detection device.

The endoscope insertion shape detection device is a device that displays an estimated insertion shape image of the endoscope 1 inserted into the body of the subject in combination with an insertion-shape-detection-only endoscope in which a magnetic coil is embedded. For example, as disclosed in JP 2019-37643 A, a plurality of magnetic coils are arranged inside the insertion portion of the endoscope 1 at predetermined intervals along a longitudinal direction of the insertion portion. A built-in antenna of a main body of the endoscope insertion shape detection device receives magnetism generated from the magnetic coil. By an AC magnetic field generated from the built-in antenna, an electromotive force is generated in each coil for position detection arranged in the insertion portion, and an induced current flows. The position of each coil is detected on the basis of the induced current flowing through the coil. The bending history information is detected according to the detected position of each coil.

Note that the bending history information may be detected by using a bending detection sensor in addition to the endoscope insertion shape detection device. The bending detection sensor includes a flexible member having a contact portion, and a flexible substrate that is in contact with the contact portion and outputs a signal corresponding to a contact position. Specifically, when a predetermined portion of the insertion portion of the endoscope 1 is bent (curved), a flexible support member and a substrate provided at a portion affected by the bending are both deformed and bent. In the bending detection sensor, the contact position between the contact portion and the substrate is shifted along a predetermined direction according to the bending of the insertion portion. Since the output signal is changed when the contact position is shifted, the bending detection sensor detects the bending history information (curving information) of the insertion portion.

The bending history information indicates a physical parameter or information regarding bending such as a bending angle and a bending direction. In accordance with the bending history information acquired from each magnetic coil arranged in the insertion portion of the endoscope 1, the control unit 21 corrects the Z coordinate, which is the insertion distance in the body cavity, by adjusting the bending shape so as to match the body cavity shape obtained from the three-dimensional image information of the body cavity (Step S213). Specifically, the control unit 21 detects the shape of the insertion portion (for example, being bent to the right at 30 degrees or the like) by arithmetic processing according to the bending angle and the bending direction. The control unit 21 recalculates the Z coordinate, which is the insertion distance, on the basis of the detected shape of the insertion portion. For example, in a case where the endoscope makes one rotation on the way, the circumferential length of the rotating portion may be subtracted from the insertion distance. In addition, for example, in a case of being bent a plurality of times in a predetermined section, the length of the bent portion is obtained by multiplying a distance per pixel by the number of pixels of the bent portion, and a difference between the length and the length of the predetermined section is obtained. Finally, the difference is subtracted from the insertion distance, and a difference between the insertion distance of the endoscope and the insertion distance in the body cavity may also be corrected. Thereafter, the control unit 21 performs Step S205.

According to the present embodiment, by outputting the endoscopic image acquired from the endoscope 1 and the virtual endoscopic image corresponding to the Z coordinate, which is the insertion distance of the endoscope 1, in association with each other, it is possible to associate the position in the endoscopic image with the position in the virtual endoscopic image reconstructed on the basis of the three-dimensional medical image.

According to the present embodiment, by correcting the position and orientation of the virtual endoscopic image on the basis of the endoscopic image acquired from the endoscope 1, it is possible to obtain the virtual endoscopic image having high similarity with the actual endoscopic image.

According to the present embodiment, by correcting the Z coordinate, which is the distance by which the endoscope 1 is inserted into the body, according to the bending history information of the endoscope 1, it is possible to acquire the Z coordinate which is the insertion distance with high accuracy.

According to the present embodiment, by matching the virtual endoscopic image reconstructed from three-dimensional data of an X-ray CT image with the actual endoscopic image, the distance image information can be added to the endoscopic image, the feature parameter obtained from the endoscopic image can be corrected using the distance information, and the image diagnosis support information with higher accuracy can be provided.

Second Embodiment

In a second embodiment, a distance image of a distance to each pixel of the lumen viewed from a viewpoint is reconstructed on the basis of a virtual endoscopic image, and a pixel value (data) of each pixel of an endoscopic image is corrected on the basis of the reconstructed distance image. Alternatively, a feature parameter obtained from each pixel is corrected. That is, a correct image measurement feature parameter can be obtained by multiplying the area of the pixel separated by a distance r by 1/r2. Furthermore, a control unit 21 of a processor 2 outputs diagnosis support information to a display device 3 on the basis of the feature parameter of the endoscopic image corrected using the distance image information. Note that a description of the contents overlapping with those of the first embodiment will be omitted.

Figures 12, 13:
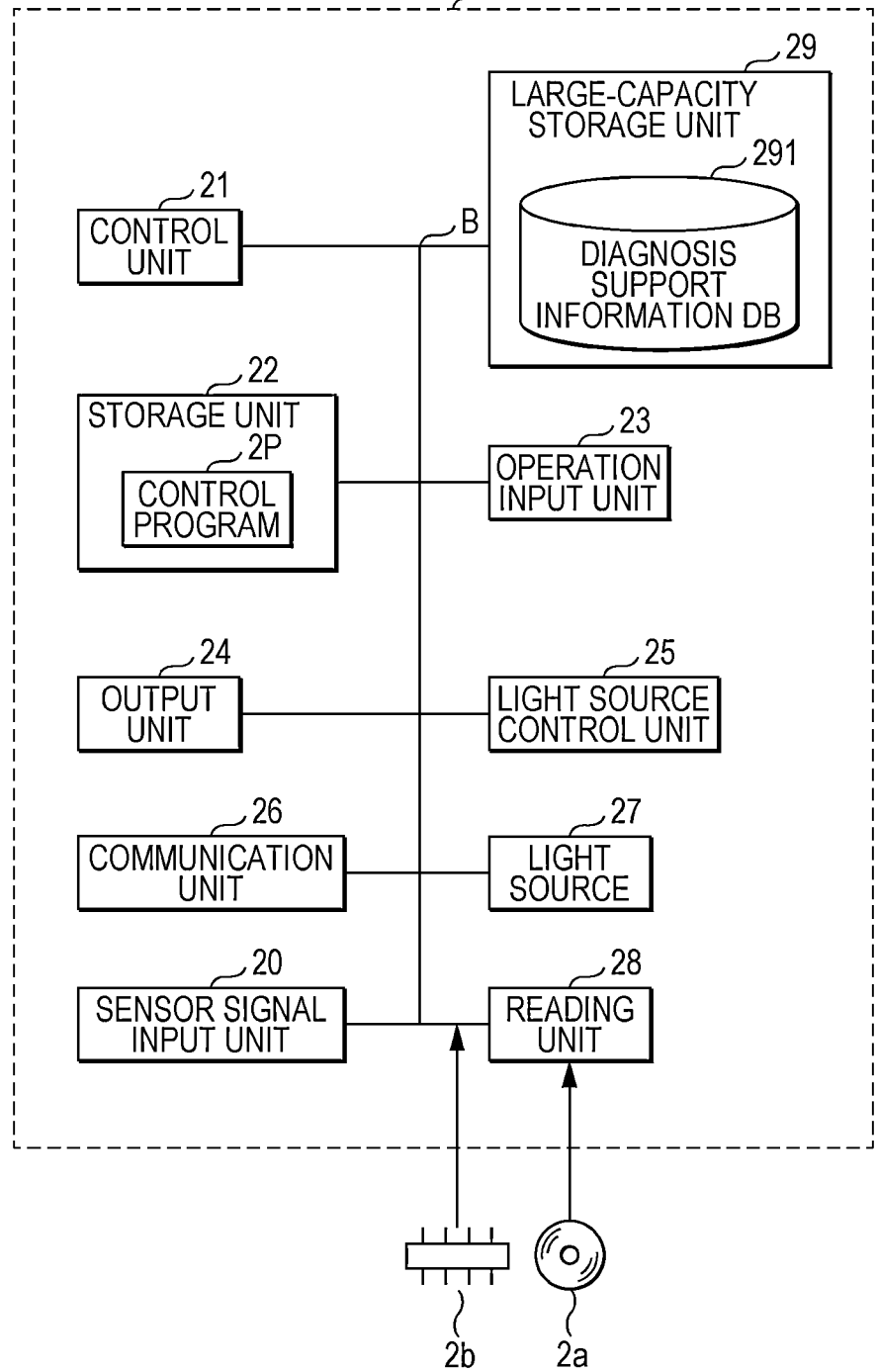
FIG. 12 is a block diagram illustrating a configuration example of a processor of a second embodiment.
FIG. 13 is an explanatory diagram illustrating an example of a record layout of a diagnosis support information DB.

FIG. 12 is a block diagram illustrating a configuration example of the processor 2 of the second embodiment. Note that the contents overlapping with those of FIG. 3 are denoted by the same reference signs and a description thereof will be omitted. A large-capacity storage unit 29 stores a diagnosis support information DB 291. The diagnosis support information DB 291 stores diagnosis support information for a patient.

FIG. 13 is an explanatory diagram illustrating an example of a record layout of the diagnosis support information DB 291. The diagnosis support information DB 291 includes a management ID column, a patient ID column, a diagnosis content column, and a diagnosis date and time column. The management ID column stores an ID of management data of the diagnosis support information uniquely specified in order to identify the management data of each piece of diagnosis support information. The patient ID column stores a patient ID that specifies the patient. The diagnosis content column stores contents of diagnosis for the patient. The diagnosis date and time column stores diagnosis date and time information for the patient. Note that the associated endoscopic image and diagnosis support information may be stored in the diagnosis support information DB 291.

The control unit 21 of the processor 2 acquires a virtual endoscopic image corresponding to a Z coordinate, which is a distance by which an endoscope 1 is inserted into the body, from a virtual endoscopic image reconstructed on the basis of a three-dimensional medical image obtained by capturing an image of the patient in advance. Note that processing of acquiring the virtual endoscopic image corresponding to the Z coordinate, which is the insertion distance, is similar to that in the first embodiment, and thus a description thereof will be omitted. The control unit 21 obtains a distance image from the virtual endoscopic image corresponding to the Z coordinate, which is the insertion distance, on the basis of a distance to each pixel appearing in the virtual endoscopic image according to a viewpoint position and a line-of-sight direction. Note that processing of obtaining the distance image will be described later.

The control unit 21 corrects a pixel value of each pixel of the endoscopic image on the basis of the reconstructed distance image. A difference in chromaticity occurs depending on a distance (long or short) to a pixel in each image region of the endoscopic image. In a case where the distance to the pixel is long, the corresponding image region appears dark, and conversely, in a case where the distance of the pixel is short, the corresponding image region appears bright. The control unit 21 of the processor 2 corrects the pixel value of each pixel in each image region of the corresponding endoscopic image on the basis of the distance to each pixel appearing in the distance image according to the viewpoint position and the line-of-sight direction.

The distance to each pixel of the endoscopic image is obtained from the distance image, and feature parameter values of each pixel and each region are corrected according to the distance. It is assumed that each pixel and each region are present at a reference distance Ra, and the feature parameters are corrected with a distance Rb to each pixel and each region. For example, in a case where the area Sb of a certain region is at the distance Rb, the feature parameters are corrected to Sb×(Rb/Ra)2.

Hereinafter, an example in which a pixel value of a pixel in an image region of a mucosal surface that is red due to rubefaction is corrected will be described. For example, in a case where the control unit 21 determines that a distance to a pixel (R1, G1, B1) in the image region of the mucosal surface is equal to or more than a reference distance (the distance to the pixel is long), since the red color of the mucosal surface looks dark, pixel value correction processing for making the red color look bright is performed on the pixel. For example, since a pixel size is changed according to a ratio of a square of the distance, the pixel value R1 is also increased by the ratio, such that the pixel (R2, G1, B1) after the correction looks red.

Conversely, in a case where the control unit 21 determines that the distance to the pixel (R1, G1, B1) in the image region of the mucosal surface is less than the reference distance (the distance to the pixel is short), since the pixel size is changed according to the ratio of the square of the distance, the pixel value R1 is also decreased by the ratio, thereby performing the pixel value correction processing for making the red color of the mucosal surface look dark.

Note that a proportion of R in the pixel may be used for the above-described pixel value correction processing for the image region of the red mucosal surface. For example, in a case where the control unit 21 determines that the distance to the pixel (R3, G3, B3) in the image region of the mucosal surface is twice the reference distance or more and three times or less, the proportion of R is calculated by a calculation formula R3/(R3+G3+B3). In a case where the control unit 21 determines that the distance to the pixel (R3, G3, B3) in the image region of the mucosal surface is three times or more the reference distance, the control unit 21 calculates the proportion of R by a calculation formula 2R3/(R3+G3+B3). On the basis of the calculated proportion of R, the control unit 21 performs the pixel value correction processing for making the red color of the mucosal surface look bright, and obtains the pixel (R4, G4, B4) after the correction.

The control unit 21 extracts the feature parameter of the image region on the basis of the image region of the endoscopic image after the pixel value correction. On the basis of the extracted feature parameter, the control unit 21 makes a determination based on AI, a decision tree, or the like, and outputs the obtained diagnosis support information to the display device 3. The feature parameter is an image geometry of each region on the endoscopic image, an image value, and a numerical value of a feature parameter calculated therefrom, and is obtained by applying an image processing method. For example, the control unit 21 may extract, as the feature parameter, specified chromaticity in the gastric mucosa, and may output diagnosis support information such as the nature of an ulcer in a case where it is determined that the extracted feature parameter is equal to or more than a threshold.

Note that the processing is not limited to the above. For example, the diagnosis support information may be output using a trained image recognition model that outputs a recognition result in a case where the endoscopic image after the pixel value correction is input. Note that the processing of outputting the diagnosis support information using the image recognition model will be described in a third embodiment to be described later.

The control unit 21 stores the output diagnosis support information in the diagnosis support information DB 291 of the large-capacity storage unit 29. Specifically, the control unit 21 assigns the management ID to associate the management ID with the patient ID and the three-dimensional position on the patient or the Z coordinate, and stores, in the diagnosis support information DB 291, a diagnosis content, a diagnosis date and time, a three-dimensional position on the patient, or the Z coordinate which is the insertion distance as one record.

Figure 14:
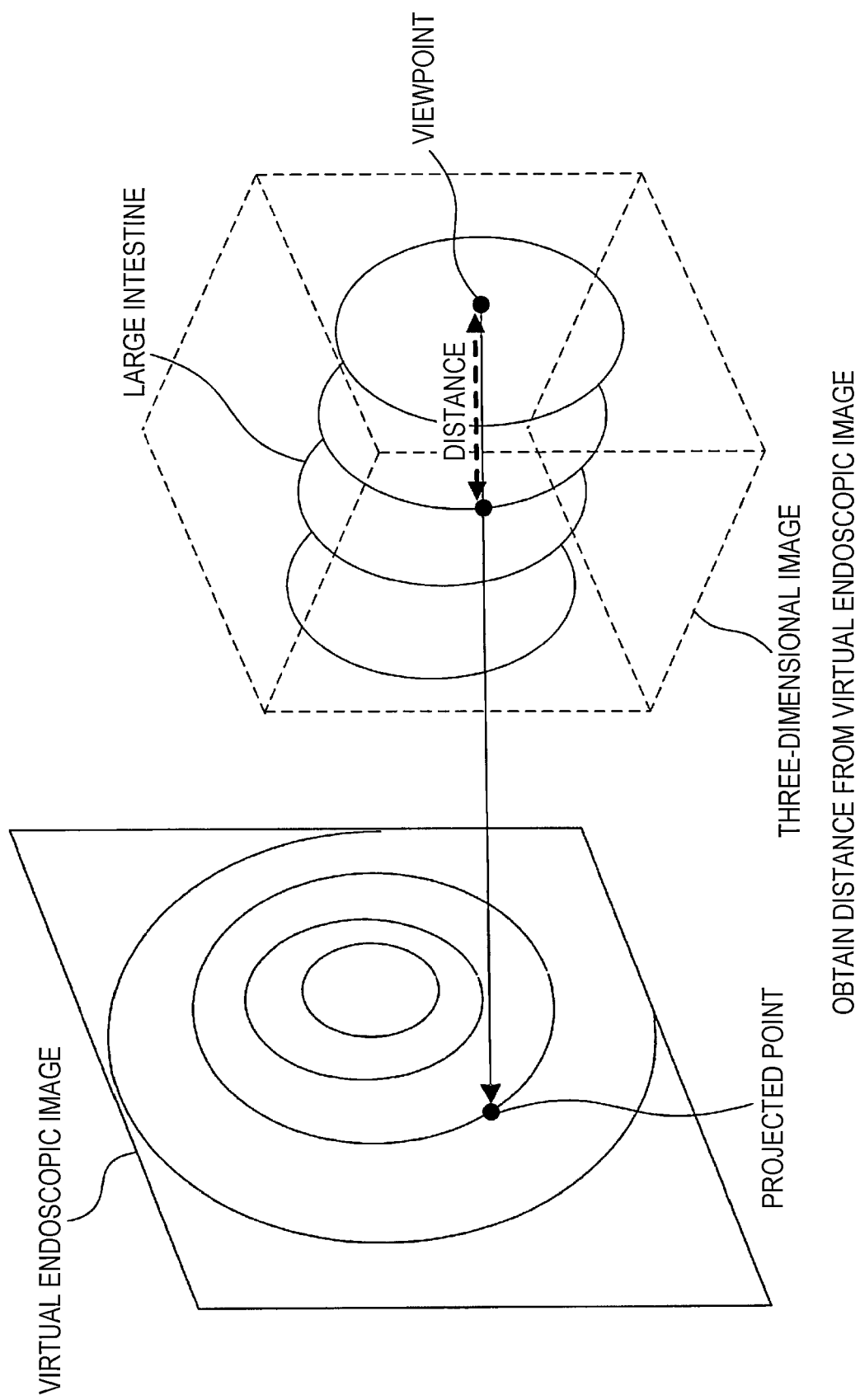
FIG. 14 is an explanatory diagram for describing processing of obtaining a distance image.

FIG. 14 is an explanatory diagram for describing processing of obtaining the distance image. The distance image is a two-dimensional image having a linear distance from a viewpoint to the observation target (for example, the inner wall of the large intestine region) as a pixel value. The control unit 21 of the processor 2 reconstructs the virtual endoscopic image on the basis of the three-dimensional medical image, and makes the reconstructed virtual endoscopic image and the endoscopic image match each other. The control unit 21 obtains (generates) the distance image on the basis of a distance from the viewpoint to a three-dimensional image corresponding to each pixel of the reconstructed virtual endoscopic image based on the viewpoint position and the line-of-sight direction at and in which the endoscopic image and the virtual endoscopic image match each other.

Figure 15:
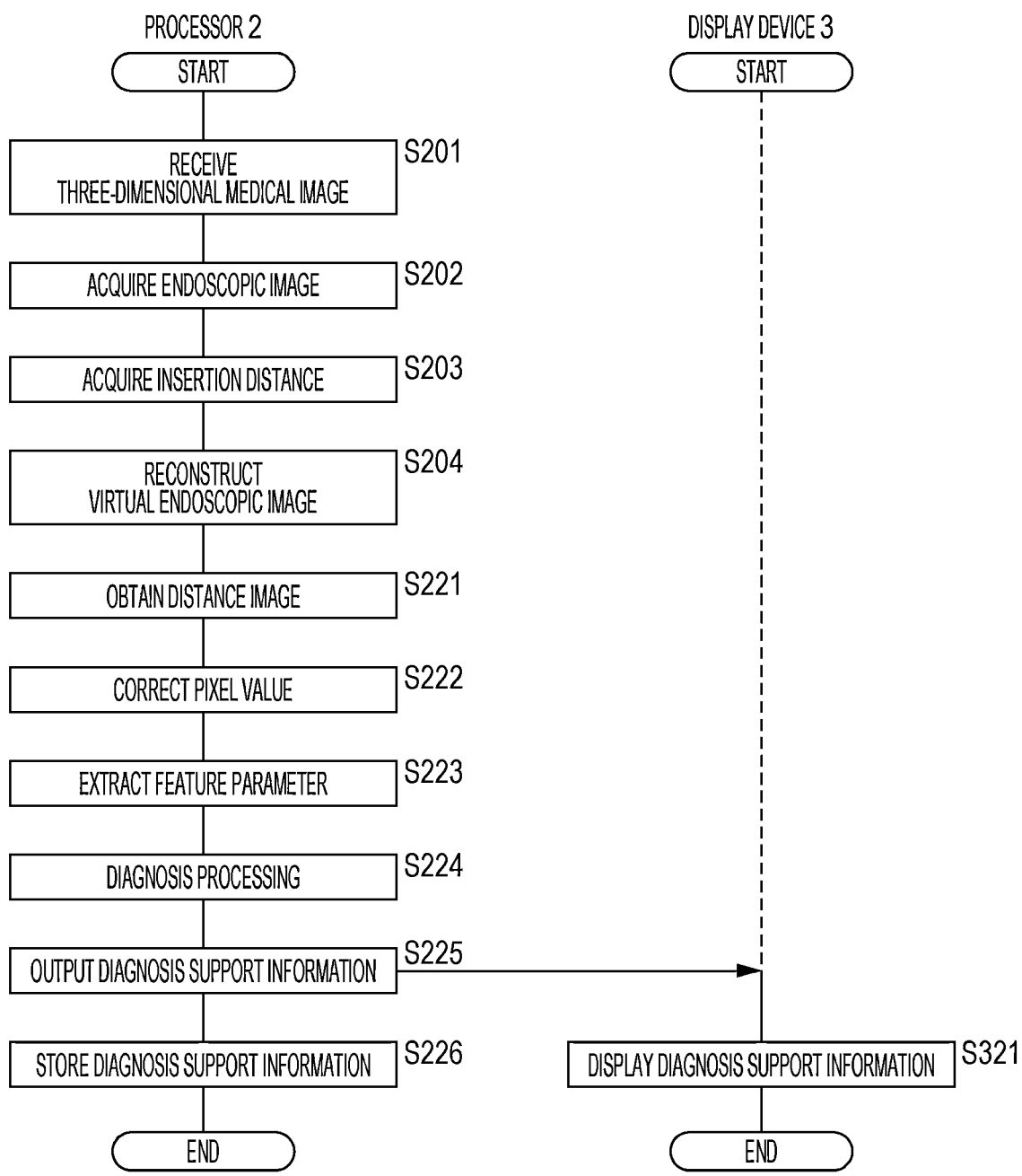
FIG. 15 is a flowchart illustrating a processing procedure when outputting diagnosis support information on the basis of an endoscopic image after pixel value correction.

FIG. 15 is a flowchart illustrating a processing procedure when outputting the diagnosis support information on the basis of the endoscopic image after the pixel value correction. Note that the contents overlapping with those of FIG. 9 are denoted by the same reference signs and a description thereof will be omitted. After acquiring the virtual endoscopic image corresponding to the Z coordinate, which is the insertion distance of the endoscope 1, in Step S204, the control unit 21 of the processor 2 obtains the distance image on the basis of the distance from the viewpoint to the three-dimensional image corresponding to each pixel of the acquired virtual endoscopic image as illustrated in FIG. 14 (Step S221).

The control unit 21 corrects the feature parameter of each image region or each pixel of the corresponding endoscopic image on the basis of the distance to each pixel appearing in the distance image according to the viewpoint position and the line-of-sight direction (Step S222). The control unit 21 extracts the feature parameter of the image region on the basis of the image region of the endoscopic image after the pixel value correction (Step S223). Note that, as for the feature parameter extraction processing, for example, in a case where a point of view on a color tone such as "the mucosal surface is red due to rubefaction" described above is feature-parameterized, a chromaticity feature parameter that is a proportion obtained by calculating R/(R+G+B) for each pixel may be extracted using each of RGB data constituting the endoscopic image. Alternatively, phase information based on a predetermined frequency component extracted by frequency component extraction means may be detected, and the feature parameter of the endoscopic image may be extracted on the basis of the detected phase information.

The control unit 21 performs diagnosis processing on the observation target on the basis of the extracted feature parameter (Step S224). For example, for the gastric mucosa, the control unit 21 may compare the extracted chromaticity of each pixel with a threshold of chromaticity, and in a case where it is determined that the chromaticity of each pixel or some pixels is equal to or greater than the threshold, the diagnosis processing may be performed according to a predetermined determination criterion. The predetermined determination criterion may be, for example, classification information of gastric ulcer according to the value of the chromaticity of the pixel.

The control unit 21 outputs the diagnosis support information obtained by the diagnosis processing to the display device 3 (Step S225). The display device 3 displays the diagnosis support information output from the processor 2 (Step S321). The control unit 21 of the processor 2 stores the output diagnosis support information in the diagnosis support information DB 291 of the large-capacity storage unit 29 (Step S226), and ends the processing.

According to the present embodiment, it is possible to obtain the distance image on the basis of the virtual endoscopic image and correct the feature parameter value of each pixel of the endoscopic image on the basis of the obtained distance image.

According to the present embodiment, it is possible to output the diagnosis support information on the basis of the endoscopic image after the pixel value correction.

Third Embodiment

The third embodiment is an embodiment in which feature parameter correction processing is performed on each image region of an endoscopic image on the basis of a distance image, and the endoscopic image after the feature parameter correction is input to an image recognition model to acquire a recognition result. Note that a description of the contents overlapping with those of the first and second embodiments will be omitted. Note that, in the present embodiment, an example of area correction processing will be described as the feature parameter correction processing.

Figure 16:
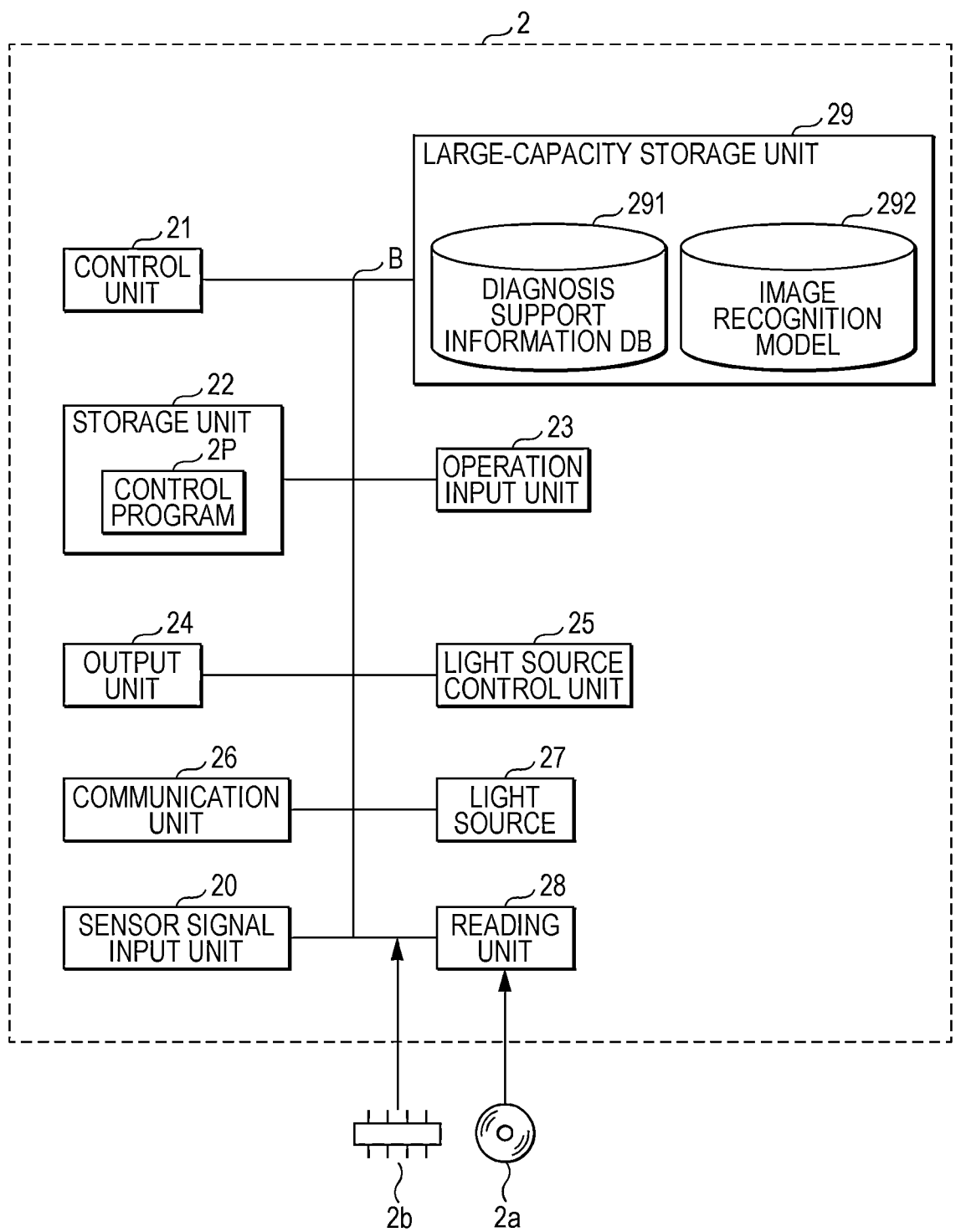
FIG. 16 is a block diagram illustrating a configuration example of a processor of a third embodiment.

FIG. 16 is a block diagram illustrating a configuration example of a processor 2 of the third embodiment. Note that the contents overlapping with those of FIG. 12 are denoted by the same reference signs and a description thereof will be omitted. An image recognition model 292 is stored in a large-capacity storage unit 29. The image recognition model 292 is an image recognizer that recognizes a lesion, a tissue, or the like in the body of a subject on the basis of a captured image, and is a trained model generated by machine learning. Note that the image recognition model 292 may be arranged and used in a cloud computing system connected via a network.

Figure 17:
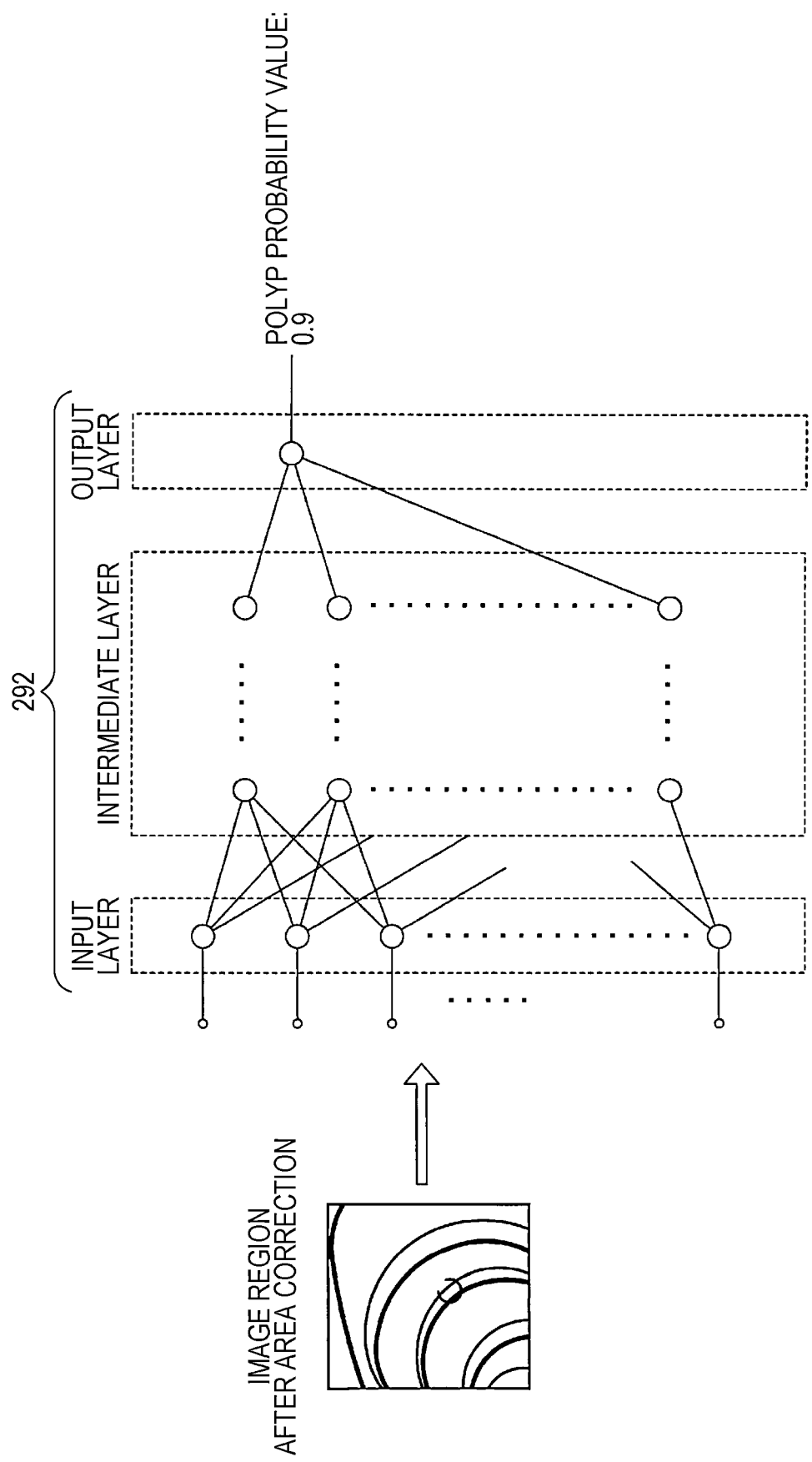
FIG. 17 is an explanatory diagram for describing processing of outputting diagnosis support information using an image recognition model.

FIG. 17 is an explanatory diagram for describing processing of outputting diagnosis support information using the image recognition model 292. The area of each image region varies depending on a distance to the image region. A control unit 21 of the processor 2 performs area correction processing on each image region of the endoscopic image by using the distance image obtained on the basis of a virtual endoscopic image. Note that the area correction processing will be described later.

The control unit 21 outputs the diagnosis support information in a case where the image region of the endoscopic image after the area correction is input to the image recognition model 292. Note that, in the following, an example of outputting a recognition result of recognizing a polyp in the large intestine by using the image recognition model 292 constructed by deep learning will be described. A polyp is a part of the mucosa of the large intestine that rises like a wart and protrudes into a space portion of the large intestine. Most of the polyps are benign diseases, and do not cause any harm to the body immediately, but if they grow gradually, they may cause bleeding or the like.

The image recognition model 292 is used as a program module that is a part of artificial intelligence software. The image recognition model 292 is an extractor that has constructed (generated) a neural network that receives the endoscopic image after the area correction and outputs a result of predicting the polyp in the large intestine. The neural network is, for example, a convolutional neural network (CNN), which includes an input layer that receives the endoscopic image after the area correction, an output layer that outputs a result of predicting a site in the large intestine, and an intermediate layer that has been trained by backpropagation.

The input layer has a plurality of neurons that receives a pixel value of each pixel included in the endoscopic image, and transfers the input pixel value to the intermediate layer. The intermediate layer has a plurality of neurons that extract an image feature parameter of the endoscopic image, and transfers the extracted image feature parameter to the output layer. For example, a case where the image recognition model 292 is a CNN will be described as an example. The intermediate layer has a configuration in which a convolutional layer that convolves the pixel value of each pixel input from the input layer and a pooling layer that maps the pixel value convolved in the convolutional layer are alternately connected. Therefore, the intermediate layer finally extracts the feature parameter of the image while compressing pixel information of the endoscopic image. Thereafter, the intermediate layer predicts a probability that the endoscopic image is a polyp in the large intestine by a fully-connected layer whose parameter is learned by backpropagation. The prediction result is output to the output layer having a plurality of neurons.

Note that the endoscopic image may be input to the input layer after passing through the convolutional layer and the pooling layer, which are alternately connected, to extract the feature parameter.

Note that an arbitrary object detection algorithm such as regions with convolutional neural network (RCNN), fast RCNN, faster RCNN, single shot multibook detector (SSD), or You Only Look Once (YOLO) may be used instead of the CNN.

Note that the present invention is not limited to the diagnosis processing of identifying a polyp by the machine learning described above. For example, the control unit 21 of the processor 2 may identify a polyp by using a local feature parameter extraction method such as accelerated KAZE (A-KAZE) or scale invariant feature transform (SIFT) on the basis of a change in hue or folds in the large intestine from the endoscopic image, and output the diagnosis support information.

Note that, although the example of the above-described area correction processing on the endoscopic image in the large intestine has been described, the present invention is not limited thereto, and the area correction processing may also be performed on other parts (for example, the stomach). Although the example of the area has been described as the above-described feature parameter, the present invention is not limited thereto, and the distance correction processing may be performed on other feature parameters.

Note that, in the present embodiment, an example of the image recognition model 292 for polyp extraction will be described, but other trained image recognition models may be used. For example, the image recognition model 292 is a trained model generated by machine learning, and may be an image recognizer that recognizes a lesion, a tissue, or the like in the body of the subject by extracting a chromaticity feature parameter of the endoscopic image. In this case, in a case where the endoscopic image after the pixel value correction in the second embodiment is input to the image recognition model 292, the diagnosis support information can be output.

Specifically, the control unit 21 of the processor 2 inputs the endoscopic image after the pixel value correction to the image recognition model 292 by using the trained image recognition model 292, and outputs a result of identifying a lesion, a tissue, or the like (for example, a polyp in the large intestine). The control unit 21 outputs the diagnosis support information on the basis of the identification result (for example, a probability value of a polyp in the large intestine)

output from the output layer of the image recognition model 292. For example, in a case where the probability value of the polyp of the large intestine is equal to or more than a predetermined threshold (for example, 0.90), the control unit 21 may determine that the lesion or tissue is a polyp.

Figure 18:
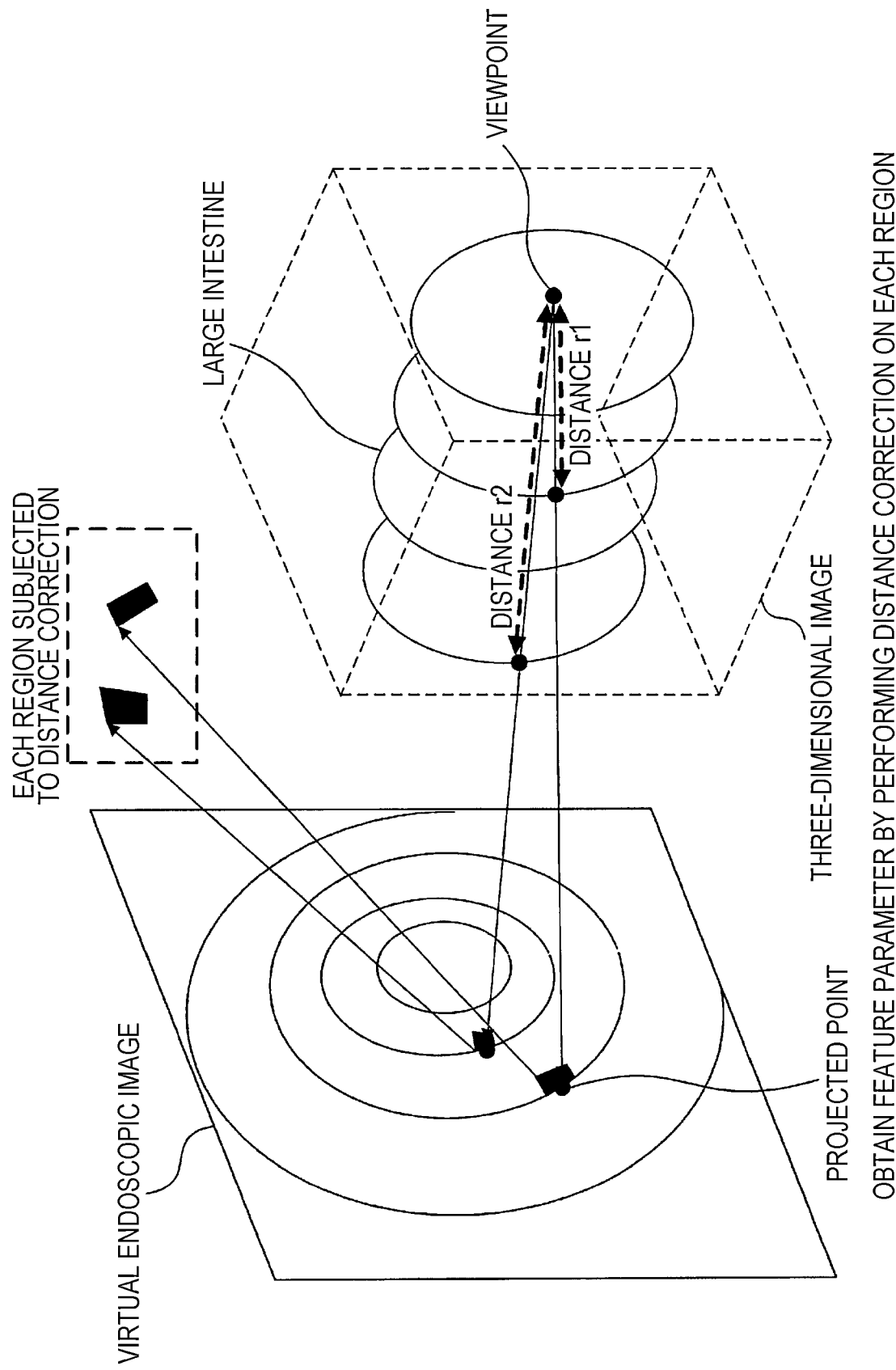
FIG. 18 is an explanatory diagram for describing an operation of obtaining a feature parameter by performing distance correction.
Figure 19:
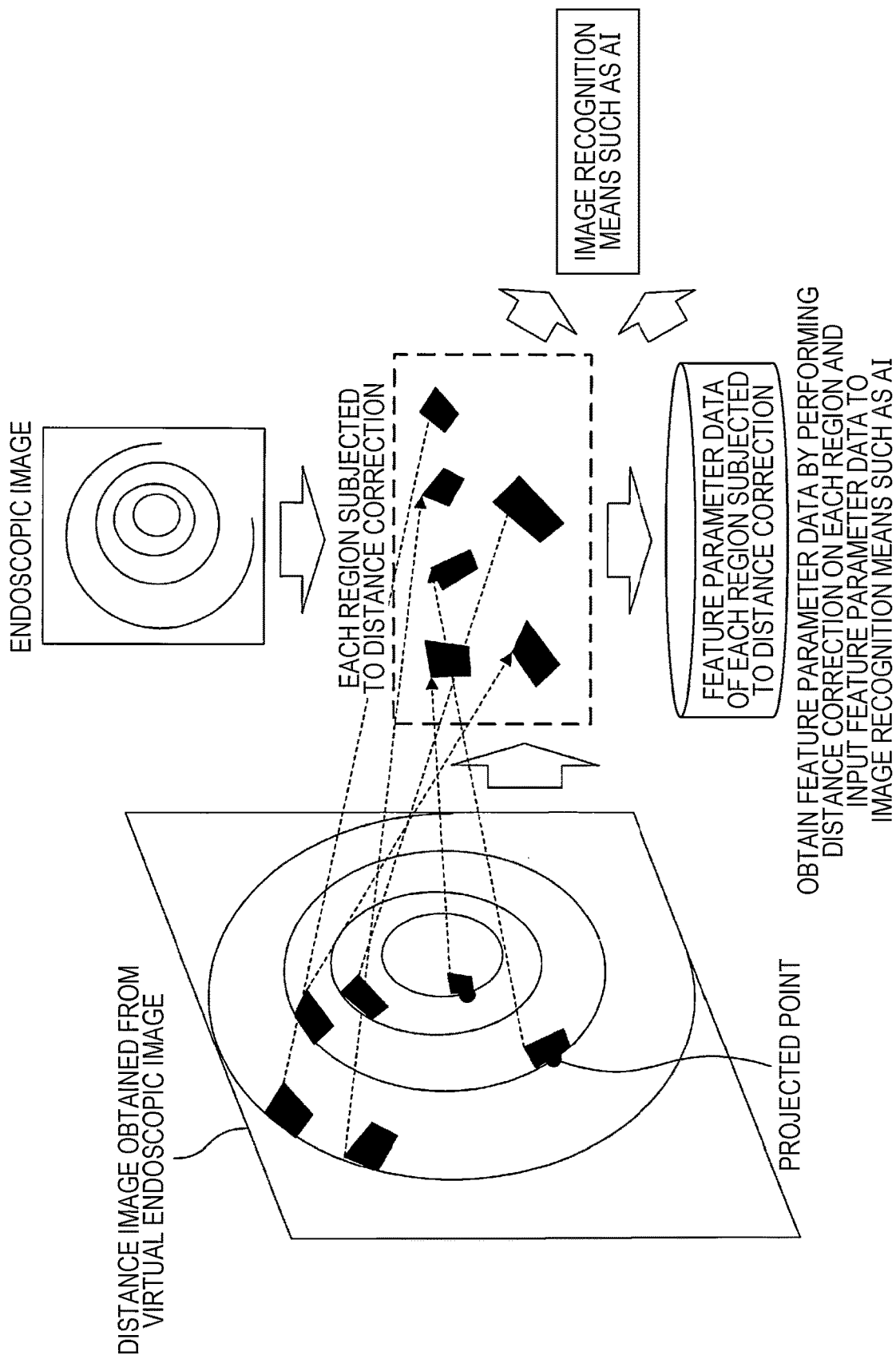
FIG. 19 is an explanatory diagram for describing an operation of performing area correction.

Hereinafter, the area correction processing will be described with reference to FIGS. 18 and 19. FIG. 18 is an explanatory diagram for describing an operation of obtaining the feature parameter by performing distance correction. FIG. 19 is an explanatory diagram for describing an operation of performing the area correction.

The control unit 21 of the processor 2 acquires a distance R (for example, r1 or r2) to each image region of the corresponding endoscopic image on the basis of the distance image obtained from the corresponding virtual endoscopic image as illustrated in FIG. 18. The control unit 21 compares the acquired distance to each image region with a reference distance (for example, 20 mm). The control unit 21 performs correction with an inverse square ratio (R/20)2 with respect to the compared distance R to each region.

In a case where it is determined that the distance to the image region of the endoscopic image is equal to or more than the reference distance (the distance to the pixel is long), the control unit 21 performs enlargement processing on the image region by correcting the number of pixels constituting the image region with the inverse square ratio (R/20)2 with respect to the distance R to each region. In a case where it is determined that the distance to the image region of the endoscopic image is less than the reference distance (the distance to the pixel is short), the control unit 21 performs contraction processing on the image region by correcting and reducing the number of pixels constituting the image region by the inverse square ratio (R/20)2 with respect to the distance R to each region. In addition, in a case where there is a difference in distance between the respective pixels in each image region, correction is performed assuming that each image region is placed at the reference distance.

As illustrated in FIG. 19, when the enlargement/contraction processing is performed on each region on the basis of the distance image information obtained from the virtual endoscopic image corresponding to the endoscopic image based on a distance ratio, for example, nearest-neighbor interpolation may be used. The nearest-neighbor interpolation is linear interpolation in which a pixel in coordinates obtained by dividing a pixel after the enlargement or contraction by an enlargement/contraction ratio and rounding the value is used as it is. Furthermore, bilinear interpolation, bicubic interpolation, Lanczos interpolation, and the like, which are technologies of image enlargement/contraction processing, may be used. Thereafter, by the above-described processing, the control unit 21 inputs the image region of the endoscopic image after the area correction to the image recognition model 292.

Figure 20:
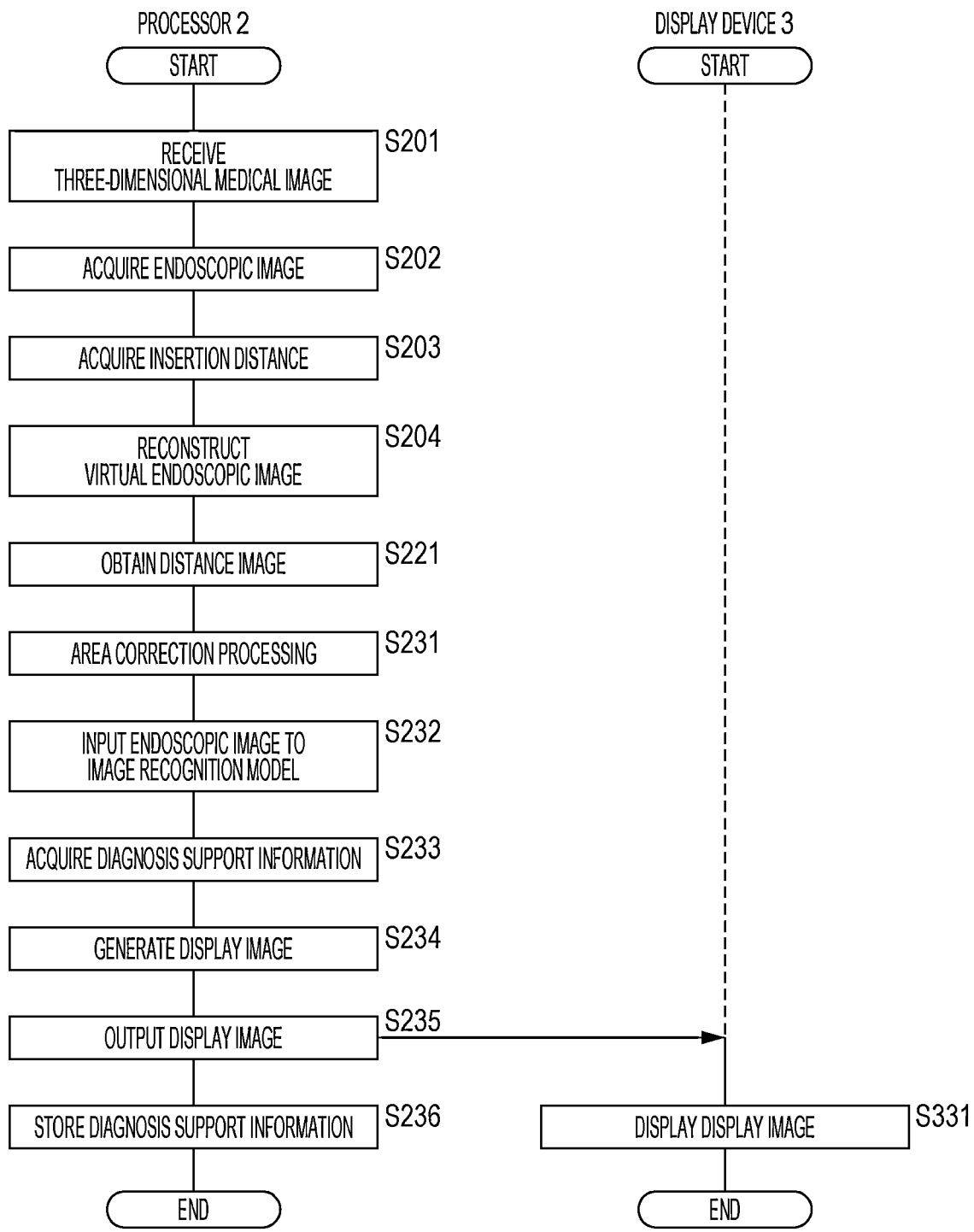
FIG. 20 is a flowchart illustrating a processing procedure when outputting the diagnosis support information by using the image recognition model.

FIG. 20 is a flowchart illustrating a processing procedure when outputting the diagnosis support information by using the image recognition model 292. Note that the contents overlapping with those of FIG. 15 are denoted by the same reference signs and a description thereof will be omitted. After obtaining the distance image in Step S221, the control unit 21 of the processor 2 performs the area correction processing on each image region of the endoscopic image by using the obtained distance image (Step S231). The control unit 21 inputs the endoscopic image subjected to the area correction processing to the image recognition model 292 (Step S232). Note that the control unit 21 may input, to the image recognition model 292, the endoscopic image obtained by performing the area correction processing on the endoscopic image after the luminance correction (pixel value correction) described in the second embodiment.

The control unit 21 extracts the image feature parameter for the endoscopic image after the area correction by using the image recognition model 292 to acquire a recognition result (diagnosis support information) of recognizing a lesion (for example, a polyp in the large intestine) or the like (Step S233). The control unit 21 generates a display image by superimposing the endoscopic image after the area correction and the diagnosis support information output from the trained image recognition model 292 by using the endoscopic image after the area correction (Step S234).

The control unit 21 outputs the generated display image to the display device 3 (Step S235). The display device 3 displays the display image output from the processor 2 (Step S331). The control unit 21 of the processor 2 stores the output diagnosis support information in the diagnosis support information DB 291 of the large-capacity storage unit 29 (Step S236), and ends the processing.

According to the present embodiment, it is possible to acquire a correct image feature parameter by performing the feature parameter correction processing on each image region of the endoscopic image.

According to the present embodiment, by inputting the endoscopic image subjected to the feature parameter correction processing to the trained image recognition model, an accurate recognition result is output, such that highly reliable diagnosis support information can be obtained.

According to the present embodiment, by correcting the feature parameter of each region of the endoscopic image on the basis of the distance image, it is possible to accurately recognize both a far lesion site (for example, a polyp) and a near lesion site by using the same image recognition model.

Fourth Embodiment

Figure 21:
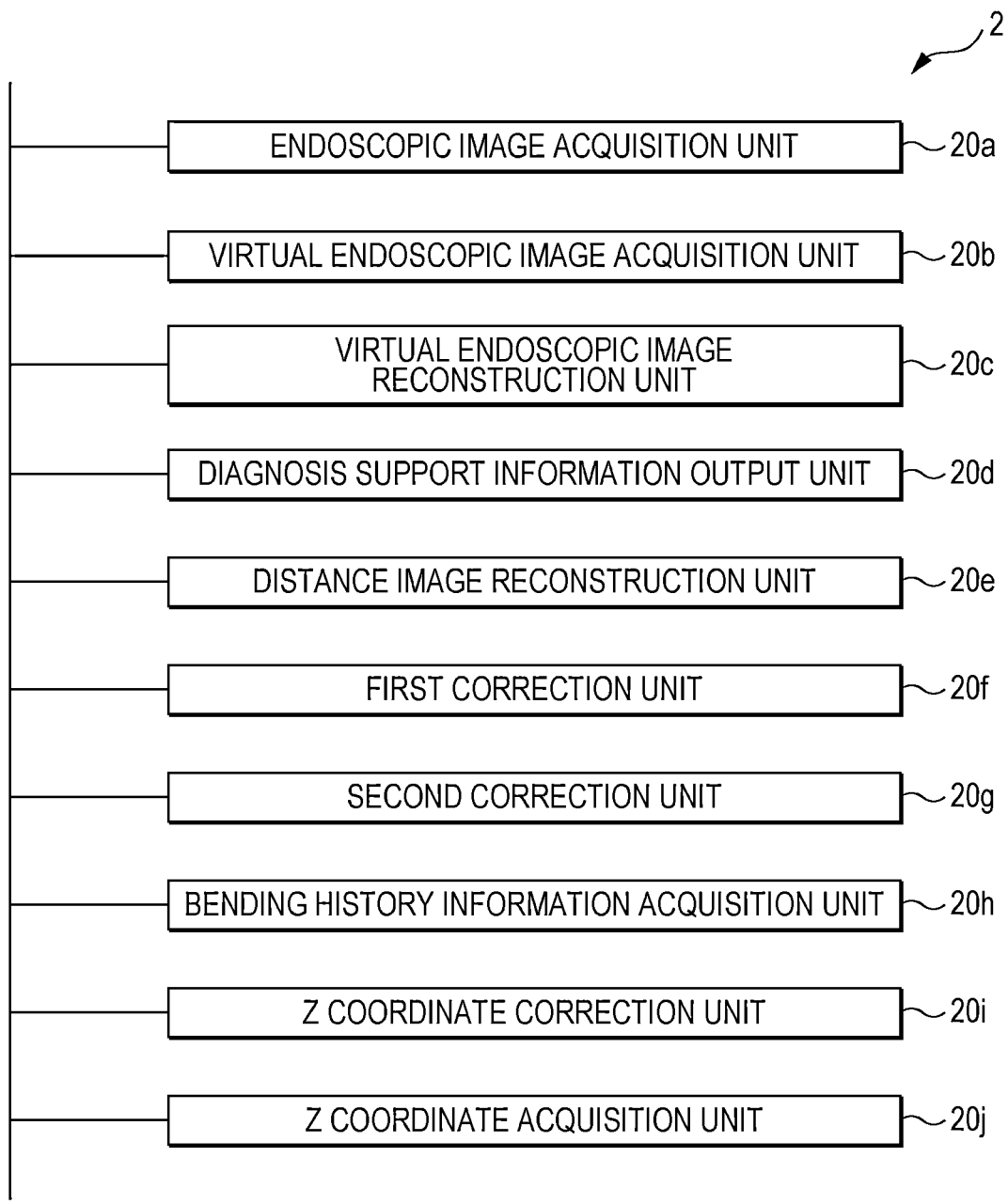
FIG. 21 is a functional block diagram illustrating an operation of the processor of the above-described embodiment.

FIG. 21 is a functional block diagram illustrating an operation of the processor 2 of the above-described embodiment. When the control unit 21 executes the control program 2P, the processor 2 is operated as follows.

An endoscopic image acquisition unit 20a acquires an endoscopic image of a patient from the endoscope 1. A virtual endoscopic image acquisition unit 20b acquires a virtual endoscopic image reconstructed (generated) on the basis of a three-dimensional medical image obtained by capturing an image of the patient in advance. A virtual endoscopic image reconstruction unit 20c reconstructs (generates) a corrected virtual endoscopic image that matches most with the endoscopic image on the basis of the degree of matching between the virtual endoscopic image acquired by the virtual endoscopic image acquisition unit 20b and the endoscopic image acquired by the endoscopic image acquisition unit 20a.

A diagnosis support information output unit 20d outputs diagnosis support information based on a feature parameter corrected according to a correspondence between each pixel of the endoscopic image acquired by the endoscopic image acquisition unit 20a and a distance image obtained from the corrected virtual endoscopic image reconstructed by the virtual endoscopic image reconstruction unit 20c. A distance image reconstruction unit 20e obtains the distance image on the basis of the virtual endoscopic image. A first correction unit 20f corrects a pixel value of each pixel of the corresponding endoscopic image according to a distance obtained from the distance image on the basis of the distance image obtained by the distance image reconstruction unit 20e.

A second correction unit 20g performs correction processing for the feature parameter of each image region of the endoscopic image acquired by the endoscopic image acquisition unit 20a on the basis of the distance image obtained by the distance image reconstruction unit 20e. A bending history information acquisition unit 20h acquires bending history information of the endoscope inserted into the body of the patient. A Z coordinate correction unit 20i corrects a Z coordinate, which is an insertion distance of the endoscope, a viewpoint direction and a viewpoint position of the virtual endoscope according to the bending history information acquired by the bending history information acquisition unit 20h. A Z coordinate acquisition unit 20j measures the Z coordinate which is the insertion distance of the endoscope inserted into the body of the patient.

In addition, the diagnosis support information output unit 20d outputs the diagnosis support information including a tumor candidate on the basis of the endoscopic image corrected by the first correction unit 20f or the second correction unit 20g. Furthermore, the diagnosis support information output unit 20d outputs a recognition result by using a trained image recognition model that outputs the recognition result in a case where the endoscopic image corrected by the first correction unit 20f or the second correction unit 20g is input.

The fourth embodiment is as described above. Since the other parts are similar to those of the first to third embodiments, the corresponding parts are denoted by the same reference signs and a detailed description thereof will be omitted.

Fifth Embodiment

Figure 22:
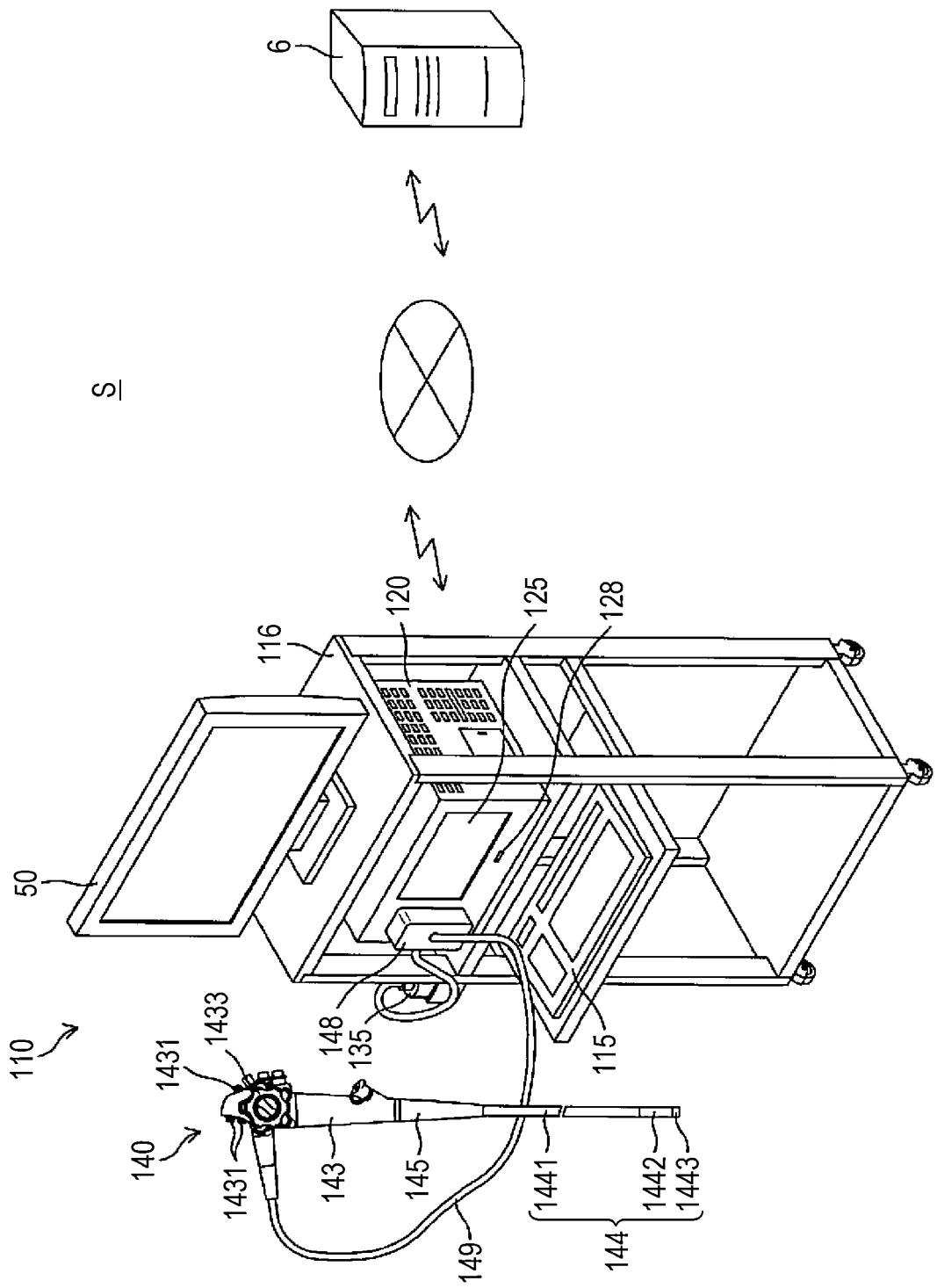
FIG. 22 is a schematic diagram illustrating an outline of a diagnosis support system according to a fifth embodiment.

Hereinafter, the present invention will be specifically described with reference to the drawings illustrating the embodiments of the present invention. FIG. 22 is a schematic diagram illustrating an outline of a diagnosis support system S according to a fifth embodiment. The diagnosis support system S includes an endoscope device 110 and an information processing device 6 communicably connected to the endoscope device 110.

The endoscope device 110 transmits an image (captured image) captured by an image sensor 1445 (see FIG. 32) of an endoscope 140 to a processor 120 for an endoscope, and the processor 120 for an endoscope performs various types of image processing such as gamma correction, white balance correction, and shading correction, thereby generating an endoscopic image that is set to be easily viewed by an operator. The endoscope device 110 outputs (transmits) the generated endoscopic image to the information processing device 6. The information processing device 6 that has acquired the endoscopic image transmitted from the endoscope device 110 performs various types of information processing on the basis of the endoscopic image, and outputs information regarding diagnosis support.

The endoscope device 110 includes the processor 120 for an endoscope, the endoscope 140, and a display device 50. The display device 50 is, for example, a liquid crystal display device or an organic electroluminescence (EL) display device.

The display device 50 is installed on the upper stage of a storage shelf 116 with casters. The processor 120 for an endoscope is housed in the middle stage of the storage shelf 116. The storage shelf 116 is arranged in the vicinity of an endoscopic examination bed (not illustrated). The storage shelf 116 includes a pull-out shelf on which a keyboard 115 connected to the processor 120 for an endoscope is mounted.

The processor 120 for an endoscope has a substantially rectangular parallelepiped shape and includes a touch panel 125 provided on one surface thereof. A reading unit 128 is arranged below the touch panel 125. The reading unit 128 is a connection interface for performing reading and writing on a portable recording medium such as a USB connector, a secure digital (SD) card slot, or a compact disc read only memory (CD-ROM) drive.

The endoscope 140 includes an insertion portion 144, an operation unit 143, a universal cord 149, and a scope connector 148. The operation unit 143 is provided with a control button 1431. The insertion portion 144 is long and has one end connected to the operation unit 143 via a bend preventing portion 145. The insertion portion 144 has a soft portion 1441, a bent portion 1442, and a distal tip portion 1443 in the order from the operation unit 143. The bent portion 1442 is bent according to an operation of a bending knob 1433. Physical detection devices such as a three-axis acceleration sensor, a gyro sensor, a geomagnetic sensor, a magnetic coil sensor and an endoscope position detection device (Colon Navigation) may be mounted on the insertion portion 144, and when the endoscope 140 is inserted into the body of a subject, detection results from these physical detection devices may be acquired.

The universal cord 149 is long, and has a first end connected to the operation unit 143 and a second end connected to the scope connector 148. The universal cord 149 is soft. The scope connector 148 has a substantially rectangular parallelepiped shape. The scope connector 148 is provided with an air/water supply port 136 (see FIG. 23) for connecting an air/water supply tube.

Figure 23:
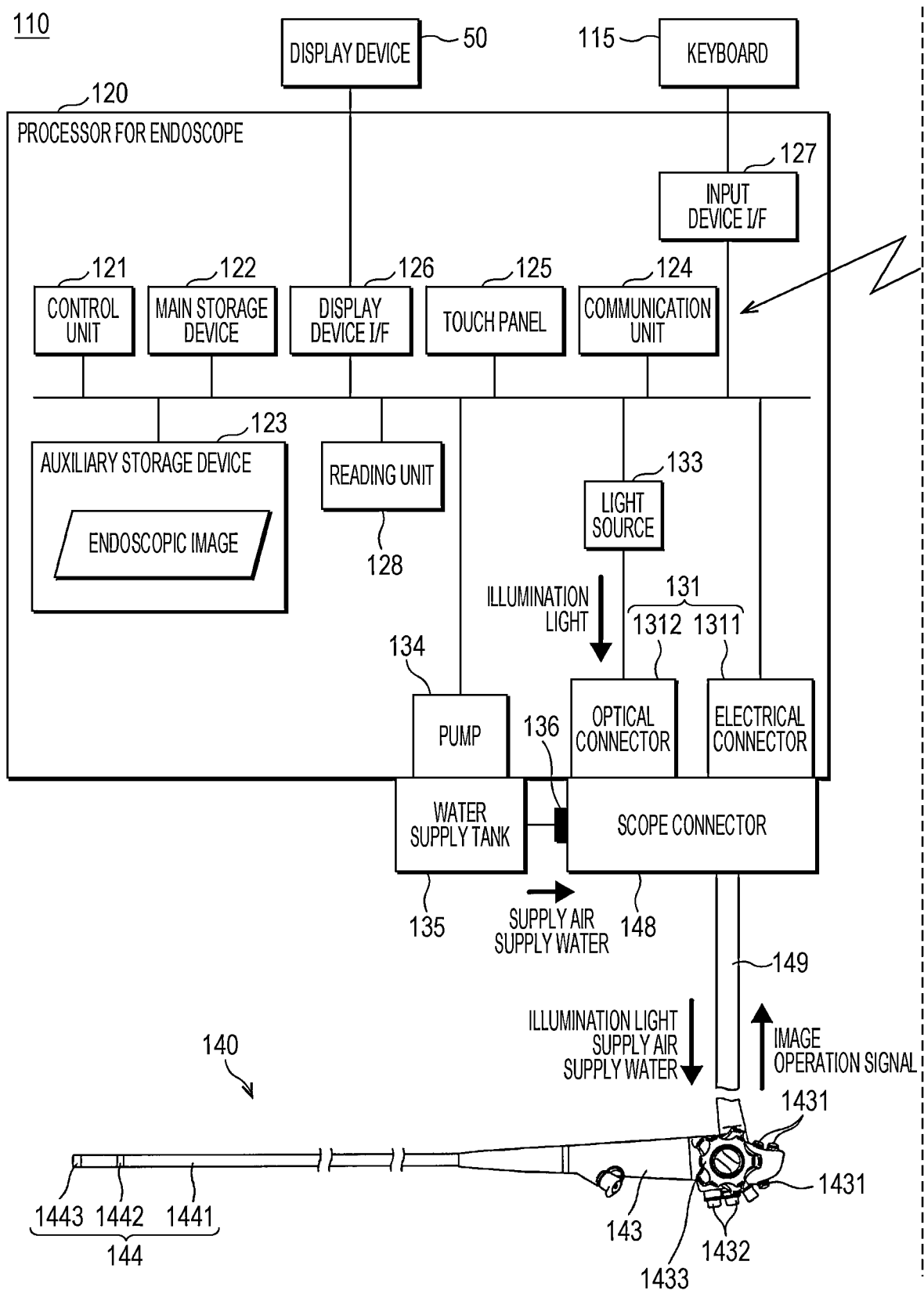
FIG. 23 is a block diagram illustrating a configuration example of an endoscope device included in the diagnosis support system.

FIG. 23 is a block diagram illustrating a configuration example of the endoscope device 110 included in the diagnosis support system S. A control unit 121 is an arithmetic control device that executes a program of the present embodiment. One or more central processing units (CPUs), graphics processing units (GPUs), or multi-core CPUs, and the like are used for the control unit 121. The control unit 121 is connected to each hardware unit constituting the processor 120 for an endoscope via a bus.

A main storage device 122 is, for example, a storage device such as a static random access memory (SRAM), a dynamic random access memory (DRAM), or a flash memory. The main storage device 122 temporarily stores information necessary during processing performed by the control unit 121 and a program being executed by the control unit 121. An auxiliary storage device 123 is, for example, a storage device such as an SRAM, a flash memory, or a hard disk, and is a storage device having a larger capacity than the main storage device 122. In the auxiliary storage device 123, for example, the acquired captured image and the generated endoscopic image may be stored as intermediate data.

A communication unit 124 is a communication module or a communication interface for performing communication with the information processing device 6 via a network in a wired or wireless manner, and is, for example, a narrow-area wireless communication module such as Wi-Fi (registered trademark) or Bluetooth (registered trademark) or a wide-area wireless communication module such as 4G or LTE. The touch panel 125 includes a display unit such as a liquid crystal display panel, and an input unit layered on the display unit. The communication unit 124 may communicate with a CT device, an MRI device (see FIG. 26), or a storage device (not illustrated) that stores data output from these devices.

A display device I/F 126 is an interface for connecting the processor 120 for an endoscope and the display device 50 to each other. An input device I/F 127 is an interface for connecting the processor 120 for an endoscope and an input device such as the keyboard 115 to each other.

A light source 133 is a high-intensity white light source such as a white LED or a xenon lamp. The light source 133 is connected to the bus via a driver (not illustrated). A change of on/off and brightness of the light source 133 is controlled by the control unit 121. Illumination light emitted from the light source 133 is incident on an optical connector 1312. The optical connector 1312 engages with the scope connector 148 to supply the illumination light to the endoscope 140.

A pump 134 generates a pressure for the air/water supply function of the endoscope 140. The pump 134 is connected to the bus via a driver (not illustrated). A change of on/off and pressure of the pump 134 is controlled by the control unit 121. The pump 134 is connected to the air/water supply port 136 provided in the scope connector 148 via a water supply tank 135.

An outline of the function of the endoscope 140 connected to the processor 120 for an endoscope will be described. A fiber bundle, a cable bundle, an air supply tube, a water supply tube, and the like are inserted inside the scope connector 148, the universal cord 149, the operation unit 143, and the insertion portion 144. The illumination light emitted from the light source 133 is radiated from an illumination window provided at the distal tip portion 1443 via the optical connector 1312 and the fiber bundle. An image of a range illuminated by the illumination light is captured by an image sensor provided at the distal tip portion 1443. The captured image is transmitted from the image sensor to the processor 120 for an endoscope via the cable bundle and an electric connector 1311. An endoscope connector 131 includes the electric connector 1311 and the optical connector 1312.

The control unit 121 of the processor 120 for an endoscope executes a program stored in the main storage device 122 to function as an image processing unit 1211. The image processing unit 1211 performs various types of image processing such as gamma correction, white balance correction, and shading correction on an image (captured image) output from the endoscope 140, and outputs the image as the endoscopic image.

Figure 24:
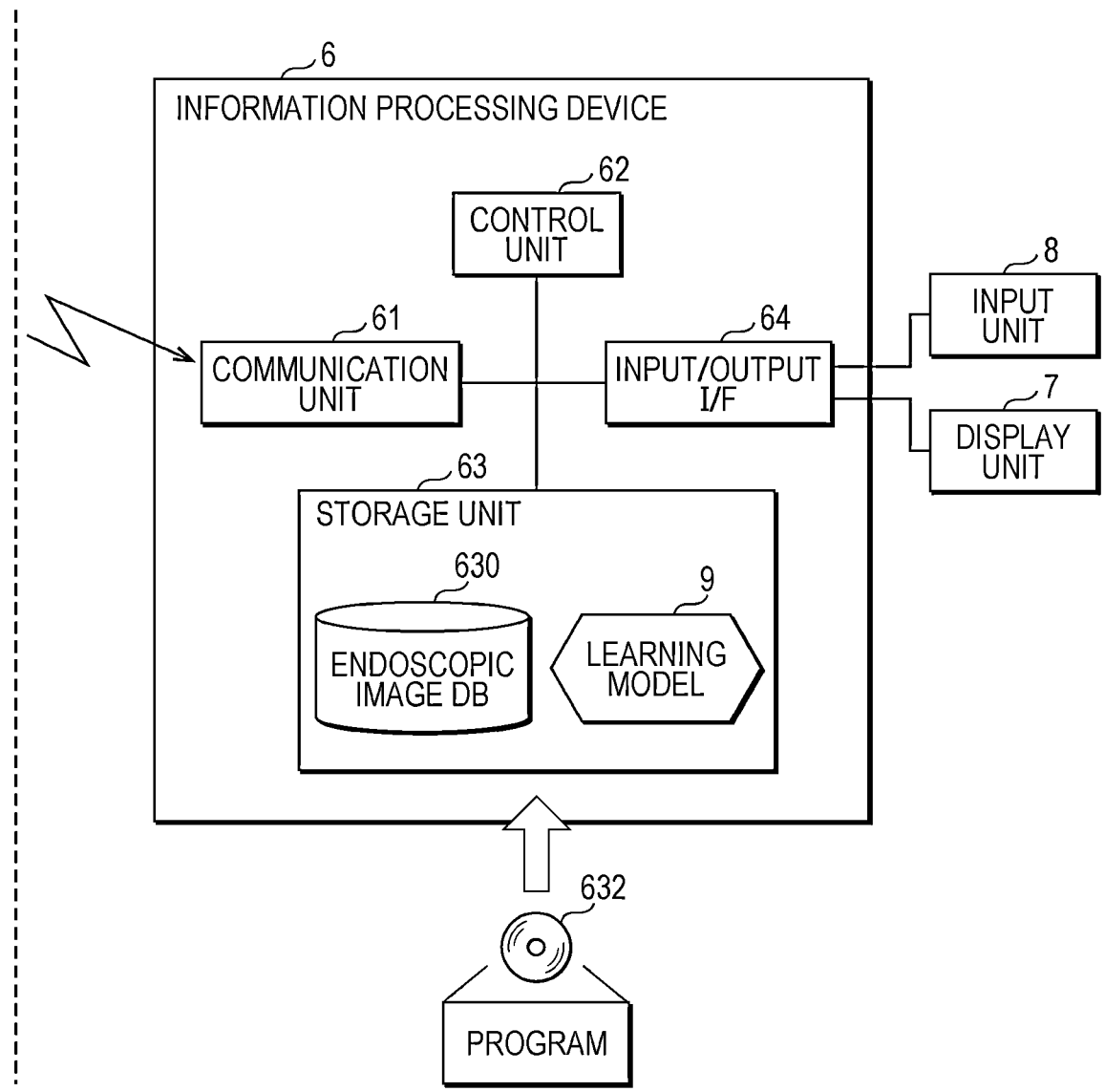
FIG. 24 is a block diagram illustrating a configuration example of an information processing device included in the diagnosis support system.

FIG. 24 is a block diagram illustrating a configuration example of the information processing device 6 included in the diagnosis support system S. The information processing device 6 includes a control unit 62, a communication unit 61, a storage unit 63, and an input/output I/F 64. The information processing device 6 is, for example, a server device, a personal computer, or the like. The server device includes not only a single server device but also a cloud server device implemented by a plurality of computers, or a virtual server device. The information processing device 6 may be provided as a cloud server located on an external network accessible from the processor 120 for an endoscope.

The control unit 62 includes one or more arithmetic processing devices having a time counting function, such as a central processing unit (CPU), a micro-processing unit (MPU), and a graphics processing unit (GPU), and reads and executes a program P stored in the storage unit 63, thereby performing various types of information processing, control processing, and the like related to the information processing device 6. Alternatively, the control unit 62 may include a quantum computer chip, and the information processing device 6 may be a quantum computer.

The storage unit 63 includes a volatile storage region such as a static random access memory (SRAM), a dynamic random access memory (DRAM), or a flash memory, and a nonvolatile storage region such as an EEPROM or a hard disk. The storage unit 63 stores in advance the program P and data to be referred to at the time of processing. The program P stored in the storage unit 63 may be a program P read from a recording medium 632 readable by the information processing device 6.

Alternatively, the program P may be downloaded from an external computer (not illustrated) connected to a communication network (not illustrated) and be stored in the storage unit 63. The storage unit 63 stores entity files (instance files of a neural network (NN)) constituting a learning model 9 to be described later. These entity files may be configured as a part of the program P. The storage unit 63 may store an endoscopic image data base (DB) 631 and the learning model 9 to be described later.

The communication unit 61 is a communication module or a communication interface for performing communication with the endoscope device 110 in a wired or wireless manner, and is, for example, a narrow-area wireless communication module such as Wi-Fi (registered trademark) or Bluetooth (registered trademark) or a wide-area wireless communication module such as 4G or LTE. The communication unit 61 may communicate with a CT device, an MRI device (see FIG. 26), or a storage device (not illustrated) that stores data output from these devices.

The input/output I/F 64 is compliant with a communication standard such as USB or DSUB, for example, and is a communication interface for performing serial communication with an external device connected to the input/output I/F 64. For example, a display unit 7 such as a display and an input unit 8 such as a keyboard are connected to the input/output I/F 64, and the control unit 62 outputs, to the display unit 7, a result of information processing performed on the basis of an execution command or an event input from the input unit 8.

Figure 25:
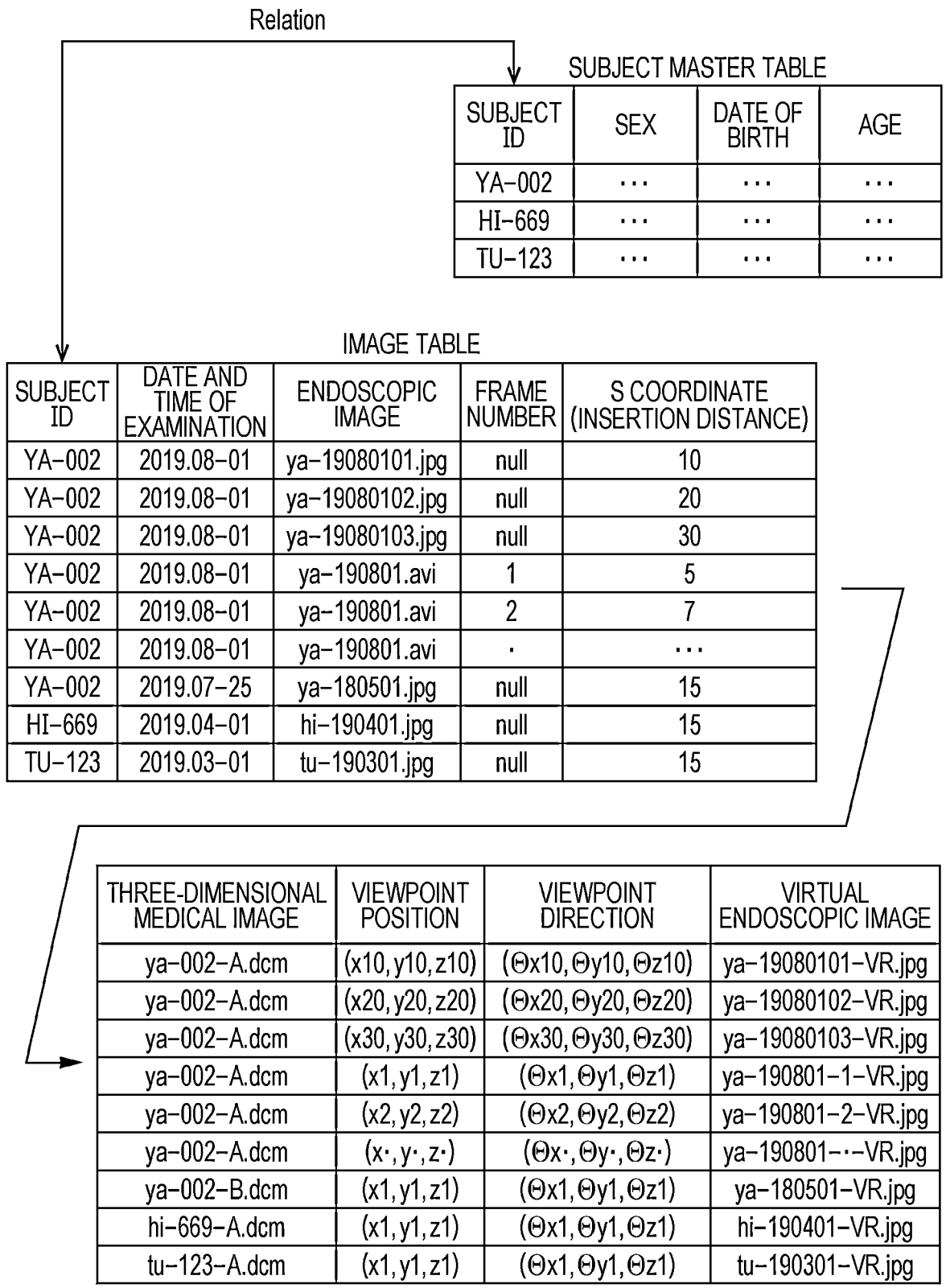
FIG. 25 is an explanatory diagram illustrating a data layout of an endoscopic image DB.

FIG. 25 is an explanatory diagram illustrating a data layout of the endoscopic image DB 631. The endoscopic image DB 631 is stored in the storage unit 63 of the information processing device 6, and is implemented by database management software such as a relational database management system (RDBMS) implemented in the information processing device 6. Alternatively, the endoscopic image DB 631 may be stored in a predetermined storage region accessible from the information processing device 6, such as a storage device communicably connected to the information processing device 6. Alternatively, the endoscopic image DB 631 may be stored in the main storage device 122 of the endoscope device 110. That is, the predetermined storage region includes the storage unit 63 of the information processing device 6, the main storage device 122 of the endoscope device 110, and a storage device accessible from the information processing device 6 or the endoscope device 110. The information processing device 6 may acquire the endoscopic image, a date of examination, and attribute information of the subject output by the processor 120 for an endoscope, and register them in the endoscopic image DB 631. Alternatively, the endoscopic image, the date of examination, and the attribute information of the subject directly output from the processor 120 for an endoscope may be directly registered in the endoscopic image DB 631.

The endoscopic image DB 631 includes, for example, a subject master table and an image table, and the subject master table and the image table are associated with each other by using a subject ID that is an item (metadata) included in both tables.

The subject master table includes, for example, a subject ID, sex, a date of birth, and age as management items (metadata). In the item (field) of the subject ID, ID information is stored in order to uniquely specify the subject who has undergone an endoscopic examination. In the items (fields) of the sex and the date of birth, biological attributes including the sex and the date of birth corresponding to the subject ID are stored, and in the item (field) of the age, the age at the current time point calculated based on the date of birth is stored. The sex and the age are managed as biological information of the subject in the subject master table.

The image table includes, for example, the subject ID, a date of examination, an endoscopic image, a frame number, an S coordinate (insertion distance), a three-dimensional medical image, a viewpoint position, a viewpoint direction, and a virtual endoscopic image as management items (metadata).

The item (field) of the subject ID is for association with the biological attributes of the subject managed in the subject master table, and stores the value of the ID of each subject. The item (field) of the date of examination stores the date when the subject corresponding to the subject ID has undergone the endoscopic examination. In the item (field) of the endoscopic image, the endoscopic image of the subject ID is stored as object data. The endoscopic image may be a still image of one frame in, for example, a jpeg format or a moving image of several frames in, for example, an avi format. Alternatively, in the item (field) of the endoscopic image, information indicating a storage location (file path) of the endoscopic image stored as a file may be stored.

In a case where the endoscopic image is a moving image, a frame number of the moving image is stored in the item (field) of the frame number. By storing the frame number of the moving image, even in a case where the endoscopic image is a moving image, the moving image can be handled in a similar manner to that for a still image, and can be associated with position information (coordinates in a coordinate system in the body) of the three-dimensional medical image or the virtual endoscopic image to be described later.

In the item (field) of the S coordinate (insertion distance), the insertion distance of the endoscope 140 at a time point when the endoscopic image stored in the same record is captured is stored as a value of the S coordinate. Derivation of the insertion distance (S coordinate) and the like will be described later.

In the item (field) of the three-dimensional medical image, for example, a three-dimensional medical image in a digital imaging and communications in medicine (DICOM) format generated on the basis of data output from a CT device (X-ray CT or X-ray cone beam CT) or an MRI device (MRI-CT) is stored as object data. Alternatively, information indicating a storage location (file path) of the three-dimensional medical image stored as a file may be stored.

In the item (field) of the viewpoint position, coordinates of the endoscope 140 in the body at the time point when the endoscopic image is captured, that is, coordinates of the three-dimensional medical image in the coordinate system are stored. Derivation of the viewpoint position and the like will be described later.

In the item (field) of the viewpoint direction, the orientation of the endoscope 140 at the time point when the endoscopic image is captured, that is, the rotation angle of the three-dimensional medical image in the coordinate system (coordinates in the coordinate system in the body) is stored. Derivation of the viewpoint direction and the like will be described later.

In the item (field) of the virtual endoscopic image, the virtual endoscopic image generated from the three-dimensional medical image is stored as object data. Information indicating a storage location (file path) of the virtual endoscopic image stored as a file may be stored. The virtual endoscopic image is generated from the three-dimensional medical image in order to perform matching processing with the endoscopic image, and for example, a virtual endoscopic image that matches most with the endoscopic image is registered in the same record as the endoscopic image. Generation of the virtual endoscopic image and the like will be described later.

Figure 26:
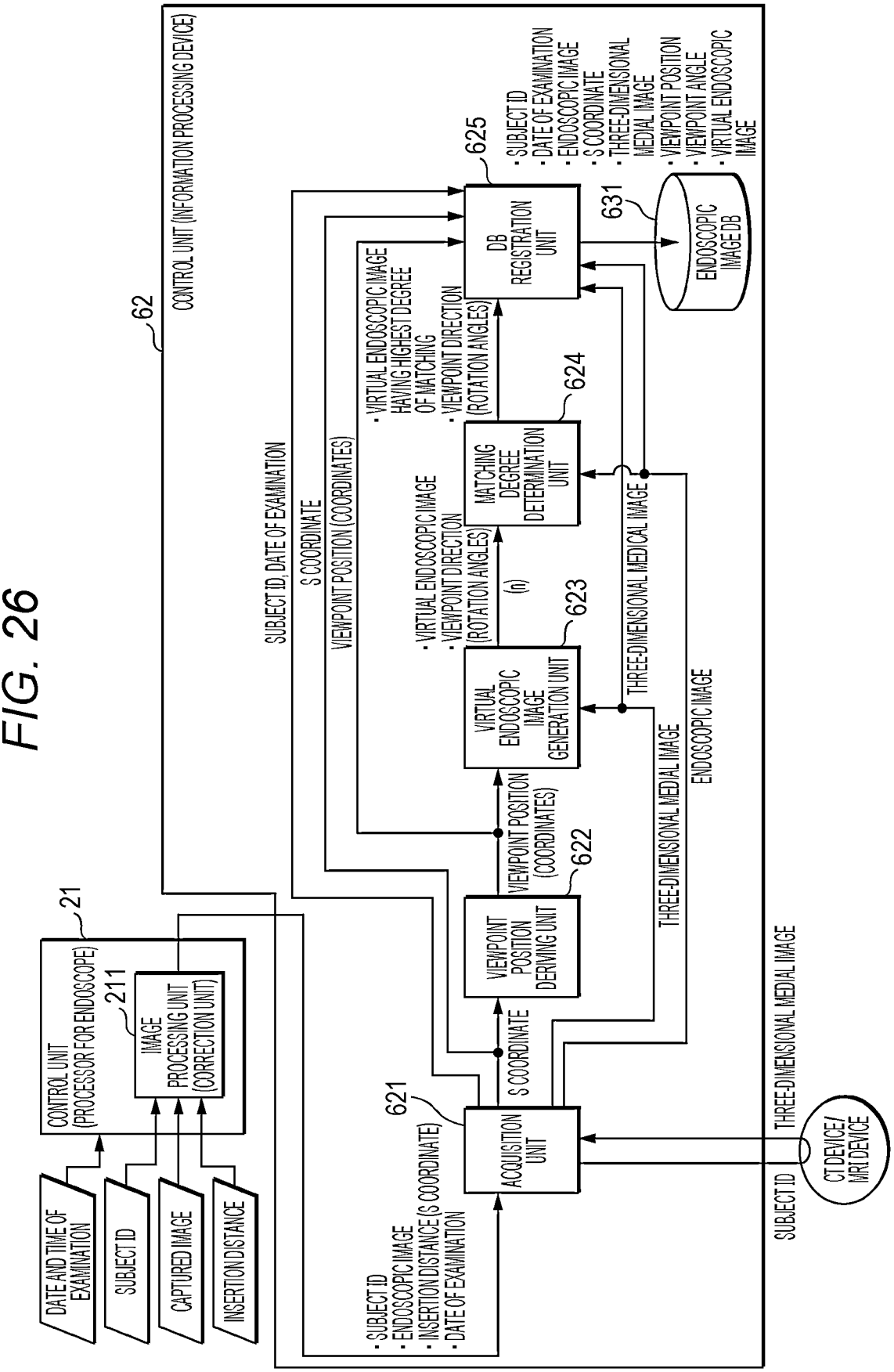
FIG. 26 is a functional block diagram illustrating functional parts included in a control unit of the information processing device.

FIG. 26 is a functional block diagram illustrating functional parts included in the control unit 62 of the information processing device 6. The control unit 121 of the processor 120 for an endoscope (endoscope device 110) executes a program stored in the main storage device 122 to function as the image processing unit 1211. The control unit 62 of the information processing device 6 executes the program P stored in the storage unit 63 to function as an acquisition unit 621, a viewpoint position deriving unit 622, a virtual endoscopic image generation unit 623, a matching degree determination unit 624, and a DB registration unit 625.

The image processing unit 1211 of the processor 120 for an endoscope performs various types of image processing such as gamma correction, white balance correction, and shading correction on an image (captured image) output from the endoscope, and outputs the image as the endoscopic image. The image processing unit 1211 outputs (transmits), to the information processing device 6, the generated endoscopic image and the date of examination based on a time point when the endoscopic image is captured. The image processing unit 1211 may further output the subject ID input from the keyboard 115 to the information processing device 6. The image processing unit 1211 may output, to the information processing device 6, information regarding the insertion distance (S coordinate) of the endoscope 140 output from a sensor disposed in the insertion portion 144 (flexible tube) of the endoscope 140 in order to measure a surrounding environment of the endoscope 140. The image processing unit 1211 may superimpose the information regarding the insertion distance of the endoscope 140 acquired from the sensor on the endoscopic image and display the information on the display device, for example.

Examples of the sensor for acquiring the S coordinate which is the distance by which the endoscope 140 is inserted into the body include a temperature sensor, an optical sensor, a pressure sensor, a wetting sensor (electrode), and a humidity sensor. For example, in a case where the sensor is an optical sensor, the optical sensor is disposed inside the insertion portion 144 (flexible tube). However, the optical sensor can receive light even when the insertion portion 144 (flexible tube) is inserted into the body. Therefore, it is possible to determine that a portion where the optical sensor receives more light is the outside of the body and a portion where the optical sensor receives less light is the inside of the body. Then, the control unit 121 of the processor 120 for an endoscope can derive the S coordinate, which is the distance (length) by which the insertion portion 144 (flexible tube) is inserted into the body by specifying the optical sensor that is positioned at a boundary position which is a body cavity insertion portion on the basis of a signal obtained by the optical sensor.

A roller encoder is attached to a mouthpiece (not illustrated) or the like that is in contact with the insertion portion 144 (flexible tube), and the roller encoder rotates by the distance by which the insertion portion 144 (flexible tube) is inserted into the body, whereby the S coordinate, which is the distance by which the endoscope 140 is inserted into the body, can be acquired. The roller encoder of the mouthpiece or the like rotates as the insertion portion 144 (flexible tube) moves forward and backward, and can measure a length between the distal tip portion 1443 of the endoscope 140 inserted into the body and an opening portion communicating with the lumen of the mouth, the nose, or the like, that is, the insertion distance of the insertion portion 144 (flexible tube). The roller encoder is electrically connected to the processor 120 for an endoscope and transmits the measured distance to the processor 120 for an endoscope. Further, an optical encoder may be used instead of the roller encoder.

In addition, in a case where an auxiliary device for measuring the insertion distance of the endoscope 140 is attached to the body cavity insertion portion which is an entrance of the subject, it is possible to acquire the S coordinate which is the distance by which the endoscope 140 is inserted into the body by measuring a passing distance of the endoscope 140. The auxiliary device may measure a distance by a scale of a magnetic field such as a linear scale attached to the insertion portion 144 (flexible tube) and a linear head attached to the mouthpiece, or may be a mouthpiece of the endoscope 140 to which a roller is attached. Note that, in a case where the endoscope is inserted into the nose, the anus, or the like, an auxiliary device that is provided with a roller and is similar to the mouthpiece may be used. Furthermore, chips in which the insertion distances are recorded may be embedded in the insertion portion 144 (flexible tube) of the endoscope 140 at regular intervals. The processor 120 for an endoscope can acquire the S coordinate which is the distance by which the endoscope 140 is inserted into the body from S coordinate information recorded in the chip obtained by the mouthpiece or the like.

The acquisition unit 621 acquires the subject ID, the date of examination, the endoscopic image, and the S coordinate (insertion distance) output by the processor 120 for an endoscope. Based on the acquired subject ID, the acquisition unit 621 acquires the three-dimensional medical image of the subject output from the communicably connected CT device or MRI device. In a case where the three-dimensional medical image output from another examination device such as the CT device or the MRI device has already been stored in, for example, an external server (not illustrated), the information processing device 6 may access the external server and acquire the three-dimensional medical image of the subject on the basis of the subject ID output from the processor 120 for an endoscope.

Examples of the three-dimensional medical image include an image represented by volume data constructed from slice data output from the CT device, the MRI device, or the like, and an image represented by volume data output from an X-ray cone beam CT device using a multi slice (MS) CT device and an X-ray flat panel. In a case where the X-ray CT device or the cone beam CT device is used, the three-dimensional medical image may be, for example, an image whose composition (body composition) of each pixel of the three-dimensional medical image is obtained on the basis of an effective mass number (effective-Z) by performing dual energy CT (DECT) scanning. In a case of using the MRI device, the three-dimensional medical image may be an image to which information regarding the composition (body composition) of each pixel of the three-dimensional medical image such as fat or lactic acid is added.

Figure 27:
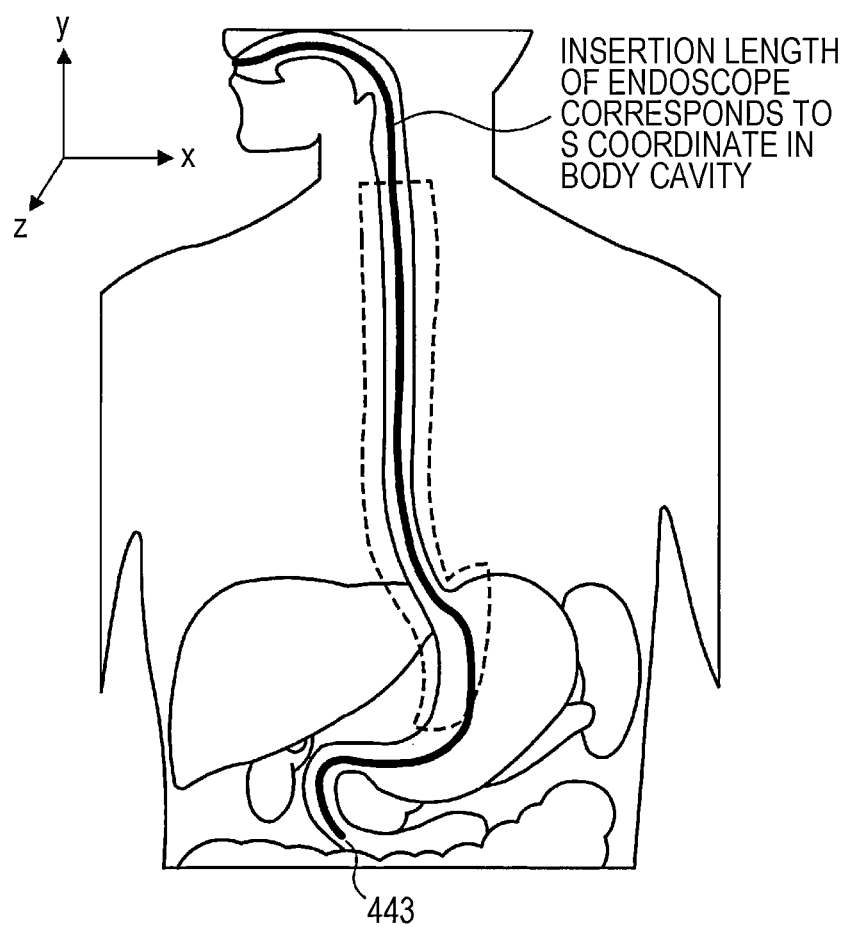
FIG. 27 is an explanatory diagram illustrating a distance (a value of an S coordinate) by which the endoscope is inserted.

The acquisition unit 621 outputs the acquired S coordinate to the viewpoint position deriving unit 622. On the basis of the acquired S coordinate, the viewpoint position deriving unit 622 derives coordinates (coordinates in the coordinate system in the body) of the three-dimensional medical image corresponding to the S coordinate, that is, a viewpoint position at which the distal tip portion 1443 of the endoscope 140 is positioned at the time point when the endoscopic image is captured. FIG. 27 is an explanatory diagram illustrating the distance (the value of the S coordinate) by which the endoscope is inserted. As illustrated in FIG. 27, an image of a digestive organ or the like captured by the endoscope 140 is expressed in a three-dimensional shape in the three-dimensional medical image. A space is formed inside the inner wall of the digestive organ or the like, and the space serves as an insertion path into which the endoscope is inserted. Since the S-coordinate, which is the insertion distance of the endoscope 140, is a place which is on the inner side of the insertion path (the inner side of the inner wall of the digestive organ or the like) and in which the length of the inserted path is substantially equal to the insertion distance, it is possible to derive the coordinates of the distal tip portion 1443 of the endoscope 140 positioned on the inner side of the inner wall of the digestive organ or the like on the basis of the S-coordinate. The viewpoint position deriving unit 622 outputs information regarding the derived viewpoint position to the virtual endoscopic image generation unit 623.

The acquisition unit 621 outputs the acquired three-dimensional medical image to the virtual endoscopic image generation unit 623. The virtual endoscopic image generation unit 623 generates a virtual endoscopic image on the basis of the acquired three-dimensional medical image and the viewpoint position acquired from the viewpoint position deriving unit 622. The virtual endoscopic image is a virtual endoscopic image of the inside of an organ (the inside of the body cavity) based on the three-dimensional medical image, which is generated (reconstructed) on the basis of the three-dimensional medical image obtained by the X-ray CT scan, the MRI scan, or the X-ray cone beam CT scan in which an image of the inside of trachea, the inside of the bronchus, or a tubular organ such as the intestinal tract is captured. For example, the virtual endoscopic image of the large intestine may be generated (reconstructed) by performing CT scanning in a state where air is introduced into the large intestine and performing volume rendering of a three-dimensional medical image obtained by the scanning from the inner side of the large intestine.

The virtual endoscopic image generation unit 623 extracts voxel data of an organ in the subject from the acquired three-dimensional medical image. The organ is, for example, the large intestine, the small intestine, the kidney, the bronchus, and a blood vessel. However, the organ is not limited thereto and may be other organs. Note that, in the present embodiment, the voxel data of the large intestine is extracted and acquired. For example, in a method of extracting a large intestine region, specifically, first, processing of reconstructing a plurality of axial images of cross sections perpendicular to a body axis on the basis of the three-dimensional medical image, and obtaining a boundary between a body surface and an intracorporeal region by using an X-ray CT value based on an X-ray absorption coefficient as a threshold to separate an extracorporeal region and the intracorporeal region from each other based on the body surface in each axial image by a known method is performed. For example, binarization processing using the X-ray CT value is performed on the reconstructed axial image, a contour is extracted by contour extraction processing, and the inside of the extracted contour is extracted as the intracorporeal (human body) region. Next, binarization processing using a threshold is performed on the axial image of the intracorporeal region, and a candidate for a region of the large intestine in each axial image is extracted. Specifically, since air is in the tract of the large intestine, a threshold (for example, −600 Hounsfield unit (HU) or less) corresponding to a CT value of air is set and binarization processing is performed, and an air region in the body in each axial image is extracted as the candidate for the region of the large intestine. The virtual endoscopic image generation unit 623 reconstructs, as the virtual endoscopic image, an image obtained by central projection in a manner of projecting voxel data on a plurality of ray directions radially extending around a line-of-sight vector based on a rotation angle set as a viewpoint position and a line-of-sight direction onto a predetermined projection plane. Note that, as a specific method of the central projection, for example, a known volume rendering method or the like can be used.

For example, the virtual endoscopic image generation unit 623 sequentially generates a plurality of candidate virtual endoscopic images by changing the viewpoint direction, that is, rotation angles ($\theta x$, $\theta y$, and $\theta z$) in a coordinate system of the three-dimensional medical image by a predetermined unit amount of 1°, for example, with the viewpoint position corresponding to the coordinates of the distal tip portion 1443 of the endoscope 140 as a starting point. That is, for example, the virtual endoscopic image generation unit 623 may project a three-dimensional shape formed by the inner wall of the digestive organ from the viewpoint position that is the inside of the digestive organ specified in the three-dimensional medical image on the basis of a plurality of rotation angles set as the viewpoint direction to generate a plurality of virtual endoscopic images. The virtual endoscopic image generation unit 623 associates the plurality of generated virtual endoscopic images with the viewpoint direction (rotation angles) used when the virtual endoscopic images are generated, and outputs the virtual endoscopic images to the matching degree determination unit 624.

The acquisition unit 621 outputs the acquired endoscopic image to the matching degree determination unit 624. On the basis of the acquired endoscopic image, the plurality of virtual endoscopic images acquired from the virtual endoscopic image generation unit 623, and the viewpoint direction (rotation angles) used when the virtual endoscopic images are generated, the matching degree determination unit 624 specifies a virtual endoscopic image that matches most with the acquired endoscopic image and a viewpoint direction (rotation angles) used when the virtual endoscopic image that matches most with the acquired endoscopic image is generated. The matching degree determination unit 624 compares the acquired endoscopic image with each of the plurality of virtual endoscopic images to derive the degree of matching between the endoscopic image and the virtual endoscopic image.

For example, the matching degree determination unit 624 may measure the degree of matching by using an index that correlates the shadow image of the endoscopic image and the shadow image of the virtual endoscopic image. In order to quantitatively determine the degree of matching between the virtual endoscopic image and the endoscopic image, the degree of matching may be determined on the basis of the degree of correlation of shadow image information obtained from luminance information. Alternatively, the degree of matching may be determined on the basis of similarity between the endoscopic image and the virtual endoscopic image. In order to measure the degree of matching between the endoscopic image and the virtual endoscopic image, for example, a method based on AI (matching degree learning model) such as a deep convolutional neural network (DCNN) implemented by a VGG 16 model (caffemodel: VGG_ILSVRC_16_layers) may be used. Alternatively, the matching degree determination unit 624 may compare the similarities between the plurality of constructed virtual endoscopic images and the endoscopic image. The similarity comparison between the two images is performed by known image processing, and either pixel data matching or matching of features extracted from the images may be used. The matching degree determination unit 624 outputs the virtual endoscopic image specified as having the highest degree of matching with the endoscopic image and the viewpoint direction (rotation angles) used to generate the virtual endoscopic image to the DB registration unit 625.

In the present embodiment, the matching degree determination unit 624 specifies a virtual endoscopic image that matches most with the acquired endoscopic image, but the present invention is not limited thereto. The matching degree determination unit 624 may specify a virtual endoscopic image whose degree of matching is equal to or more than a predetermined value as a virtual endoscopic image that can be regarded as being substantially identical to the acquired endoscopic image and output the virtual endoscopic image to the DB registration unit 625. By specifying the virtual endoscopic image whose degree of matching is equal to or more than the predetermined value, it is not necessary to perform comparison with all the virtual endoscopic images generated as candidates, and it is possible to reduce a calculation load and a processing time of the information processing device 6.

In a case where the degree of matching is not equal to or more than the predetermined value, the matching degree determination unit 624 may regenerate a plurality of virtual endoscopic images on the basis of a viewpoint position obtained by finely correcting the viewpoint position acquired from the viewpoint position deriving unit 622, derive the degree of matching between the plurality of regenerated virtual endoscopic images and the endoscopic image, and specify a virtual endoscopic image having the highest degree of matching. In this case, the matching degree determination unit 624 outputs, to the DB registration unit 625, the virtual endoscopic image having the highest degree of matching, and the viewpoint position and the viewpoint direction finely corrected and used to generate the virtual endoscopic image.

The acquisition unit 621 outputs the acquired subject ID, the date of examination, the endoscopic image, and the three-dimensional medical image to the DB registration unit 625. In a case where the endoscopic image is a moving image, the acquisition unit 621 outputs a frame number of the endoscopic image to the DB registration unit 625 in accordance with the endoscopic image. The DB registration unit 625 associates the acquired subject ID, the date of examination, the endoscopic image (assigned with the frame number in a case of a moving image), the S coordinate, the three-dimensional medical image, the viewpoint position acquired from the viewpoint position deriving unit 622, the virtual endoscopic image acquired from the matching degree determination unit 624, and the viewpoint direction (rotation angles) with each other, and registers them in the endoscopic image DB 631, thereby storing these pieces of data.

In the present embodiment, the respective functional parts in a series of processing have been described separately as a functional part of the control unit 121 of the processor 120 for an endoscope and a functional part of the control unit 62 of the information processing device 6, but the sharing of these functional parts is an example and is not limited thereto. The control unit 121 of the processor 120 for an endoscope may function as all functional parts of the control unit 62 of the information processing device 6. That is, the processor 120 for an endoscope may substantially include the information processing device 6. Alternatively, the control unit 121 of the processor 120 for an endoscope may only output a captured image captured by the image sensor 1445, and the control unit 62 of the information processing device 6 may function as all functional parts that perform the following processing. Alternatively, the control unit 121 of the processor 120 for an endoscope and the control unit 62 of the information processing device 6 may function as respective functional parts in a series of processing in cooperation by performing inter-process communication, for example.

Figure 28:
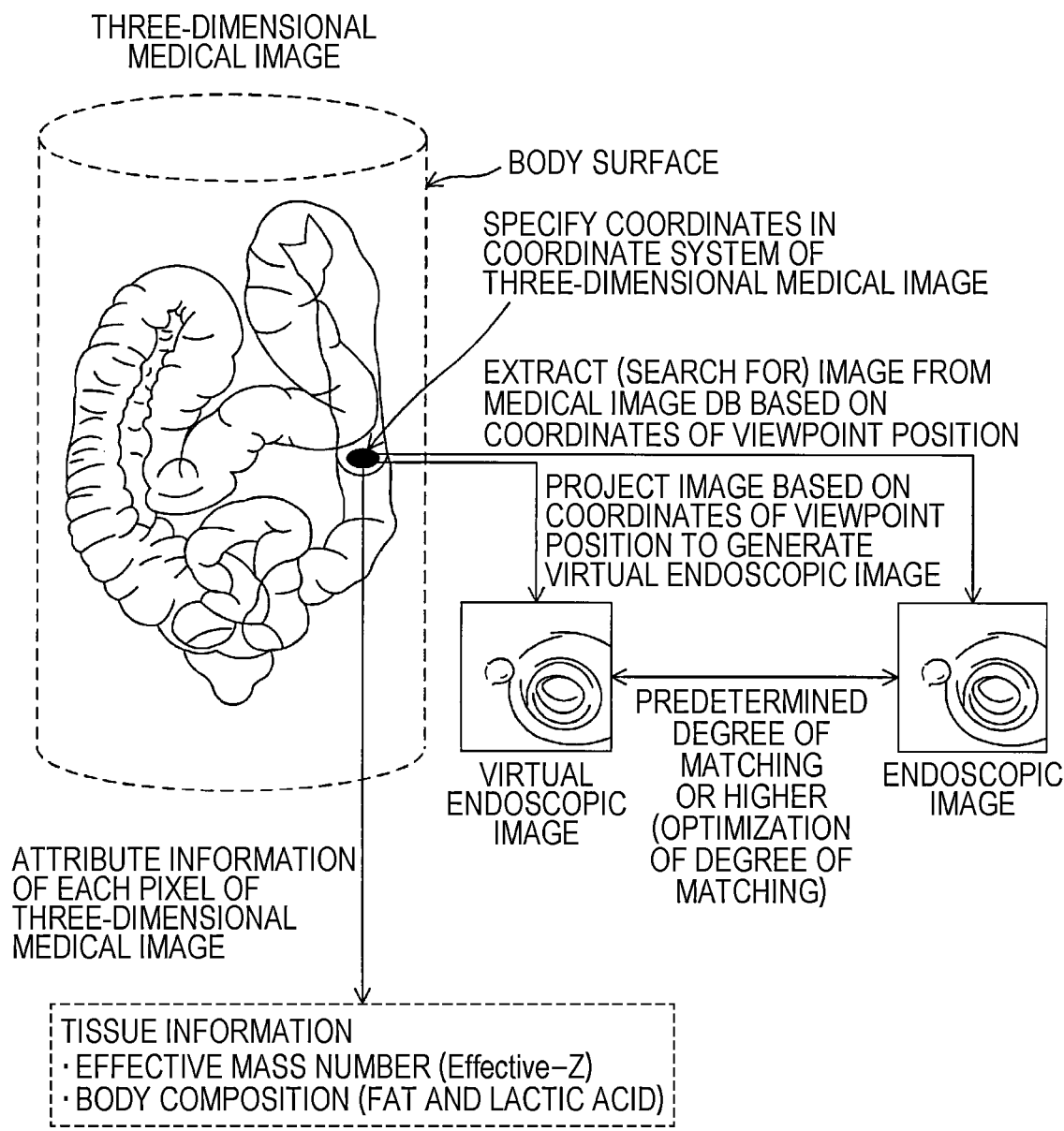
FIG. 28 is an explanatory diagram regarding a relationship between the endoscopic image and a three-dimensional medical image.

FIG. 28 is an explanatory diagram regarding a relationship between the endoscopic image and the three-dimensional medical image. In FIG. 28, a relationship between the three-dimensional medical image, the virtual endoscopic image, and the endoscopic image is represented in an object-oriented manner.

As described above, the three-dimensional medical image, the virtual endoscopic image, and the endoscopic image registered in the endoscopic image DB 631 are associated with each other on the basis of the viewpoint position and the viewpoint direction at the time point when the endoscopic image is captured. The viewpoint position corresponds to the coordinates (x, y, z) in the coordinate system (the coordinate system in the body) of the three-dimensional medical image. The viewpoint direction corresponds to rotation angles (θx, θy, and θz) in an x axis, a y axis, and a z axis in the coordinate system (the coordinate system in the body) of the three-dimensional medical image.

Each pixel of the endoscopic image corresponds to each pixel of the virtual endoscopic image (the virtual endoscopic image that matches most with the endoscopic image). The virtual endoscopic image is an image generated by performing projection by vector conversion using a viewpoint vector defined by the viewpoint direction (rotation angles) on the basis of the three-dimensional medical image with the viewpoint position as a starting point, and the coordinates in the coordinate system (the coordinate system in the body) of the three-dimensional medical image are determined by a pixel of the virtual endoscopic image.

As described above, since each pixel of the virtual endoscopic image corresponds to each pixel of the endoscopic image, the pixel of the endoscopic image, that is, the coordinates of an intracorporeal site included in the endoscopic image in the coordinate system (the coordinate system in the body) of the three-dimensional medical image can be determined on the basis of the pixel of the virtual endoscopic image. That is, with the virtual endoscopic image as an intermediate medium, it is possible to associate the pixel (intracorporeal site) of the endoscopic image with the coordinates in the coordinate system (the coordinate system in the body) of the three-dimensional medical image.

Color information and narrow band pixel information of the pixel of the endoscopic image may be added to the three-dimensional medical image, and the three-dimensional medical image may be registered in the endoscopic image DB 631. In a case where the pixel information of the endoscopic image such as the difference or the color information is added to the three-dimensional medical image, it is desirable to perform luminance correction by an image capturing light source 1446. As described above, a distance between the pixel of the endoscopic image and the view-point position (a point of the image capturing light source 1446) is derived on the coordinate system of the three-dimensional medical image. Therefore, luminosity included in the pixel information of the endoscopic image may be corrected on the basis of a reciprocal obtained by squaring the derived distance. In a case where there are a plurality of endoscopic images including pixels positioned at the same coordinates in the coordinate system of the three-dimensional medical image, an endoscopic image having the shortest distance may be given priority, and corresponding pixel information may be applied to the three-dimensional medical image to calculate a weighted average by applying a weight according to the distance or to calculate a simple average.

When capturing the three-dimensional medical image, in a case where the X-ray CT device or the cone beam CT device is used, the three-dimensional medical image may be, for example, an image whose composition (body composition) of each pixel of the three-dimensional medical image is obtained on the basis of an effective mass number (effective-Z) by performing dual energy CT (DECT) scanning. Further, in a case of using the MRI device, the three-dimensional medical image may be an image to which information regarding the composition (body composition) of each pixel of the three-dimensional medical image such as fat or lactic acid is added. As described above, by adding the effective mass number (effective-Z) and the information regarding the body composition such as fat or lactic acid to the composition of each pixel of the three-dimensional medical image, it is possible to provide diagnosis support information in which these pieces of added information and the endoscopic image associated with the coordinates specified by each pixel of the three-dimensional medical image are associated with each other to a doctor or the like.

By configuring the endoscopic image DB 631 in this manner and further adding the pixel information of the endoscopic image to the registered three-dimensional medical image, various medical data output from the CT device or the MRI device and the endoscope device 110 can be integrally managed, searched and extracted from various viewpoints, and the extracted three-dimensional medical image, endoscopic image, and the like can be associated with each other and provided to a doctor or the like as the diagnosis support information.

Figure 29:
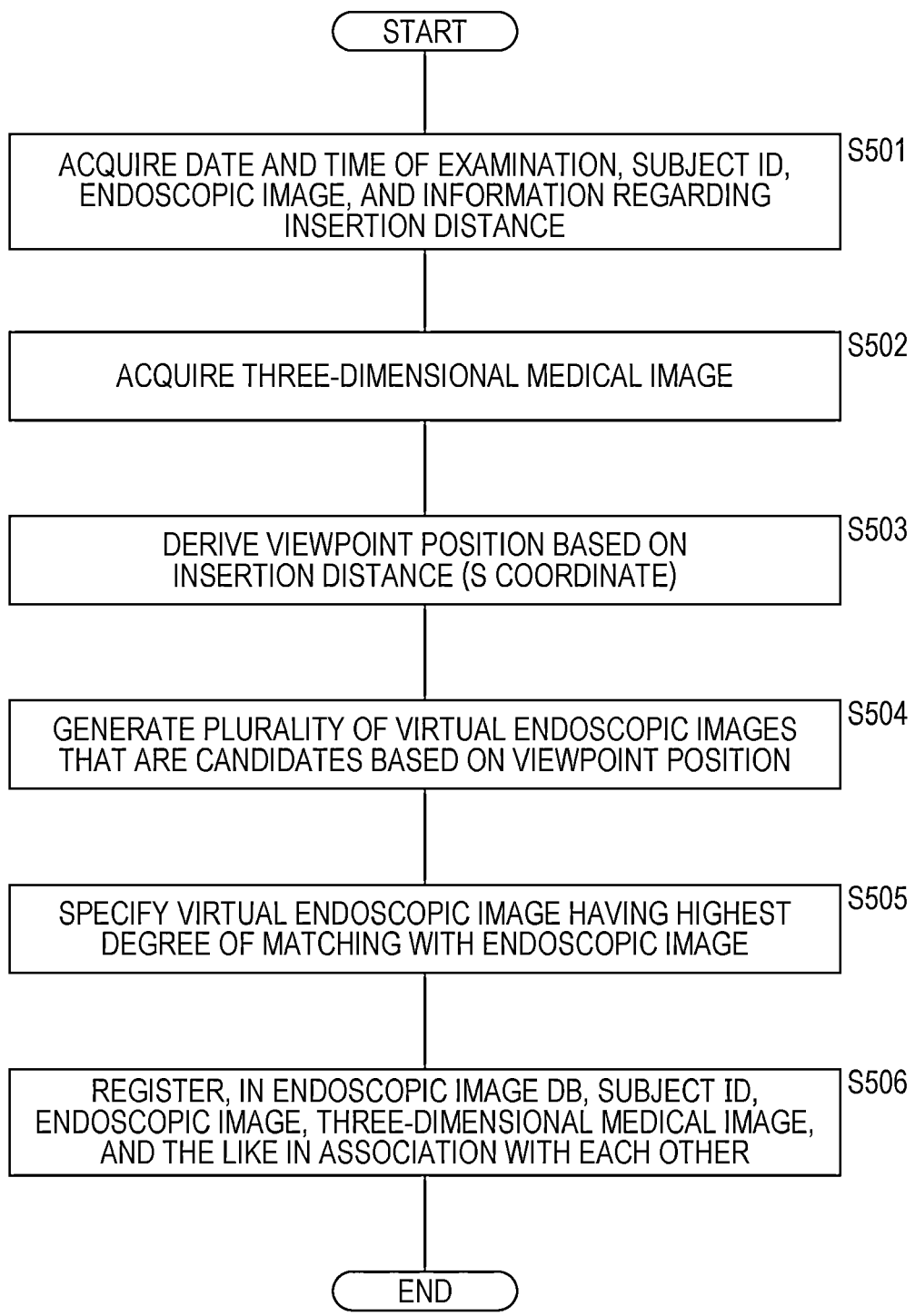
FIG. 29 is a flowchart illustrating an example of a processing procedure performed by the control unit of the information processing device.

FIG. 29 is a flowchart illustrating an example of a processing procedure performed by the control unit 62 of the information processing device 6. For example, the information processing device 6 starts the processing of the flowchart on the basis of a content input through the input unit 8 connected to the information processing device 6 itself.

The control unit 62 of the information processing device 6 acquires the date of examination, the subject ID, the endoscopic image, and the information regarding the insertion distance output from the processor 120 for an endoscope (S501). The endoscopic image acquired by the control unit 62 from the processor 120 for an endoscope may be a still image or a moving image. In addition to the endoscopic image, the control unit 62 acquires the information regarding the insertion distance of the endoscope 140 output from the optical sensor or the like, and attribute information of the subject such as the date of examination (a date on which the endoscopic image is captured) and the subject ID.

The control unit 62 of the information processing device 6 acquires the three-dimensional medical image output from another examination device such as the CT device or the MRI device (S502). The acquisition of the three-dimensional medical image may be performed by the information processing device 6 being communicably connected to another examination device such as the CT device or the MRI device. Alternatively, in a case where the three-dimensional medical image output from another examination device such as the CT device or the MRI device has already been stored in, for example, an external server (not illustrated), the information processing device 6 may access the external server and acquire the three-dimensional medical image of the subject on the basis of the subject ID output from the processor 120 for an endoscope. Alternatively, the processor 120 for an endoscope may be communicably connected to another examination device such as the CT device or the MRI device, and the control unit 62 of the information processing device 6 may acquire the three-dimensional medical image from the CT device, the MRI device, or the like via the processor 120 for an endoscope.

The control unit 62 of the information processing device 6 derives the viewpoint position on the basis of the insertion distance (S coordinate) (S503). For example, the control unit 62 acquires the information regarding the insertion distance (S coordinate) from the optical sensor or the like arranged inside the insertion portion 144 (flexible tube) of the endoscope 140 via the processor 120 for an endoscope, and derives the coordinates of the distal tip portion 1443 of the endoscope 140 positioned inside the inner wall of the digestive organ or the like into which the endoscope is inserted on the basis of the acquired insertion distance (S coordinate) and the three-dimensional medical image. The coordinates are coordinates in the coordinate system (the coordinate system in the body) of the three-dimensional medical image set with a predetermined point as the origin.

The control unit 62 of the information processing device 6 generates a plurality of candidate virtual endoscopic images on the basis of the viewpoint position (S504). The control unit 62 sequentially generates the plurality of candidate virtual endoscopic images by changing the viewpoint direction, that is, the rotation angles (θx, θy, and θz) in the coordinate system of the three-dimensional medical image by a predetermined unit amount with the viewpoint position corresponding to the coordinates of the distal tip portion 1443 of the endoscope 140 as a starting point. For example, in a case where the predetermined unit amount is 10°, the control unit 62 may have 36 resolutions with respect to the rotation angle of each axis, that is, may generate $36^3$ (46656) candidate virtual endoscopic images.

The control unit 62 of the information processing device 6 specifies a virtual endoscopic image having the highest degree of matching with the endoscopic image among the plurality of generated virtual endoscopic images (S505). For example, the control unit 62 may measure the degree of matching by using an index that correlates the shadow image of the endoscopic image and the shadow image of the virtual endoscopic image. The control unit 62 specifies the virtual endoscopic image having the highest degree of matching and a viewpoint direction (rotation angle) at the time of generating the virtual endoscopic image.

The control unit 62 of the information processing device 6 registers, in the endoscopic image DB 631, the date of examination, the subject ID, the endoscopic image, the insertion distance (S coordinate), the three-dimensional medical image, the viewpoint position, the viewpoint direction, and the virtual endoscopic image having the highest degree of matching in association with each other (S506). The control unit 62 registers, in the endoscopic image DB 631, the date of examination, the subject ID, the endoscopic image, and the insertion distance (S coordinate) acquired from the processor 120 for an endoscope, the three-dimensional medical image acquired from the CT device or the like, the viewpoint position, the virtual endoscopic image having the highest degree of matching, and the viewpoint direction (rotation angles) at the time of generating the virtual endoscopic image in association with each other. By registering each data in the endoscopic image DB 631 in this manner, the virtual endoscopic image and the endoscopic image can be registered in association with each other on the basis of the coordinates in the coordinate system of the virtual endoscopic image.

Sixth Embodiment

Figure 30:
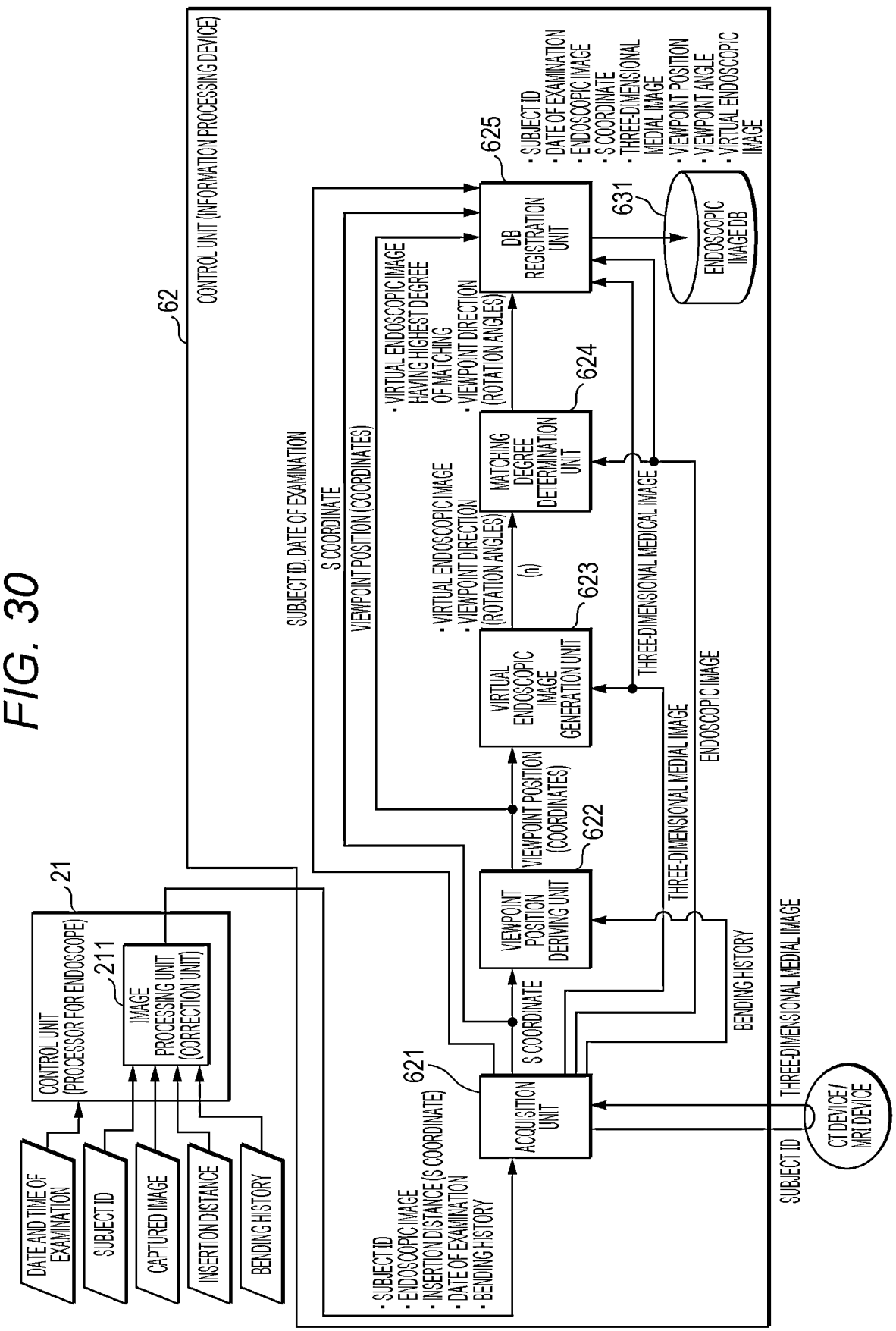
FIG. 30 is a functional block diagram illustrating functional parts included in a control unit of an information processing device according to a sixth embodiment.

An information processing device 6 of a sixth embodiment is different from that of the fifth embodiment in that a viewpoint position is corrected based on a bending history acquired from a processor 120 for an endoscope. FIG. 30 is a functional block diagram illustrating functional parts included in a control unit 62 of the information processing device 6 according to the sixth embodiment.

A control unit 121 of the processor 120 for an endoscope acquires bending history information of an endoscope 140 inserted into the body, and determines an insertion state of the endoscope 140 according to the acquired bending history information. The control unit 121 of the processor 120 for an endoscope may detect the bending history information by using, for example, an endoscope insertion shape detection device (not illustrated) connected to the processor 120 for an endoscope. For example, as disclosed in JP 2019-37643 A, the endoscope insertion shape detection device may be a device in which a plurality of magnetic coils are arranged inside an insertion portion 144 of the endoscope 140 at predetermined intervals along a longitudinal direction of the insertion portion 144. The bending history information indicates a physical parameter or information regarding bending such as a bending angle and a bending direction.

An acquisition unit 621 of the information processing device 6 acquires an endoscopic image and the like from the processor 120 for an endoscope and further acquires the bending history information, similarly to the fifth embodiment. The acquisition unit 621 outputs the acquired bending history information to a viewpoint position deriving unit 622.

The viewpoint position deriving unit 622 corrects an insertion distance (S coordinate) on the basis of the acquired bending history information, and derives the viewpoint position on the basis of the corrected insertion distance (S coordinate), similarly to the fifth embodiment. The viewpoint position deriving unit 622 detects the shape of the insertion portion 144 (for example, being bent to the right at 30 degrees or the like) by arithmetic processing according to a bending angle and a bending direction. The control unit 121 recalculates the S coordinate, which is the insertion distance, on the basis of the detected shape of the insertion portion 144. Thereafter, each functional part such as a virtual endoscopic image generation unit 623 performs processing similarly to the fifth embodiment, and a DB registration unit 625 registers each data in an endoscopic image DB 631 similarly to the fifth embodiment.

The viewpoint position deriving unit 622 of the information processing device 6 corrects the viewpoint position on the basis of the bending history acquired from the processor 120 for an endoscope. However, the present invention is not limited thereto. The control unit 121 of the processor 120 for an endoscope may correct the insertion distance on the basis of the acquired bending history information and output the corrected insertion distance to the information processing device 6. The acquisition unit 621 of the information processing device 6 may acquire the viewpoint position corrected on the basis of the bending history information by the control unit 121 of the processor 120 for an endoscope, and the subsequent processing may be performed in a similar manner to that in the fifth embodiment.

Position information for associating the endoscopic image with a three-dimensional medical image is derived on the basis of information regarding the bending history, information regarding the insertion distance, and the length of an insertion path of the endoscope 140 specified in the three-dimensional medical image. Accuracy of the insertion distance (S coordinate) can be improved by correcting the information regarding the insertion distance on the basis of the information regarding the bending history. Therefore, it is possible to accurately specify the viewpoint position (coordinates) and a viewpoint direction (rotation angles) of the endoscope 140 in a coordinate system of the three-dimensional medical image at the time point when the endoscopic image is captured, to efficiently generate a suitable virtual endoscopic image, and to further improve accuracy in association between the endoscopic image and the three-dimensional medical image.

The control unit 121 of the processor 120 for an endoscope acquires, by using, for example, an endoscope position detection device (Colon Navigation), three-dimensional information regarding the insertion shape of the endoscope 140 output from the endoscope position detection device. Then, the control unit 62 (viewpoint position deriving unit 622) of the information processing device 6 may derive the position (viewpoint position) of the endoscope 140 in the body by applying the acquired three-dimensional information regarding the insertion shape of the endoscope 140 to the three-dimensional medical image. The position information for associating the endoscopic image with the three-dimensional medical image is derived on the basis of the information regarding the shape of the endoscope 140, the information regarding the bending history, the information regarding the insertion distance, and the three-dimensional medical image. Therefore, the position (viewpoint position) and the rotation angles (viewpoint direction) of the endoscope 140 in the coordinate system of the three-dimensional medical image at the time point when the endoscopic image is captured can be specified on the basis of the shape of the endoscope 140, and the accuracy in association between the endoscopic image and the three-dimensional medical image can be further improved.

Figure 31:
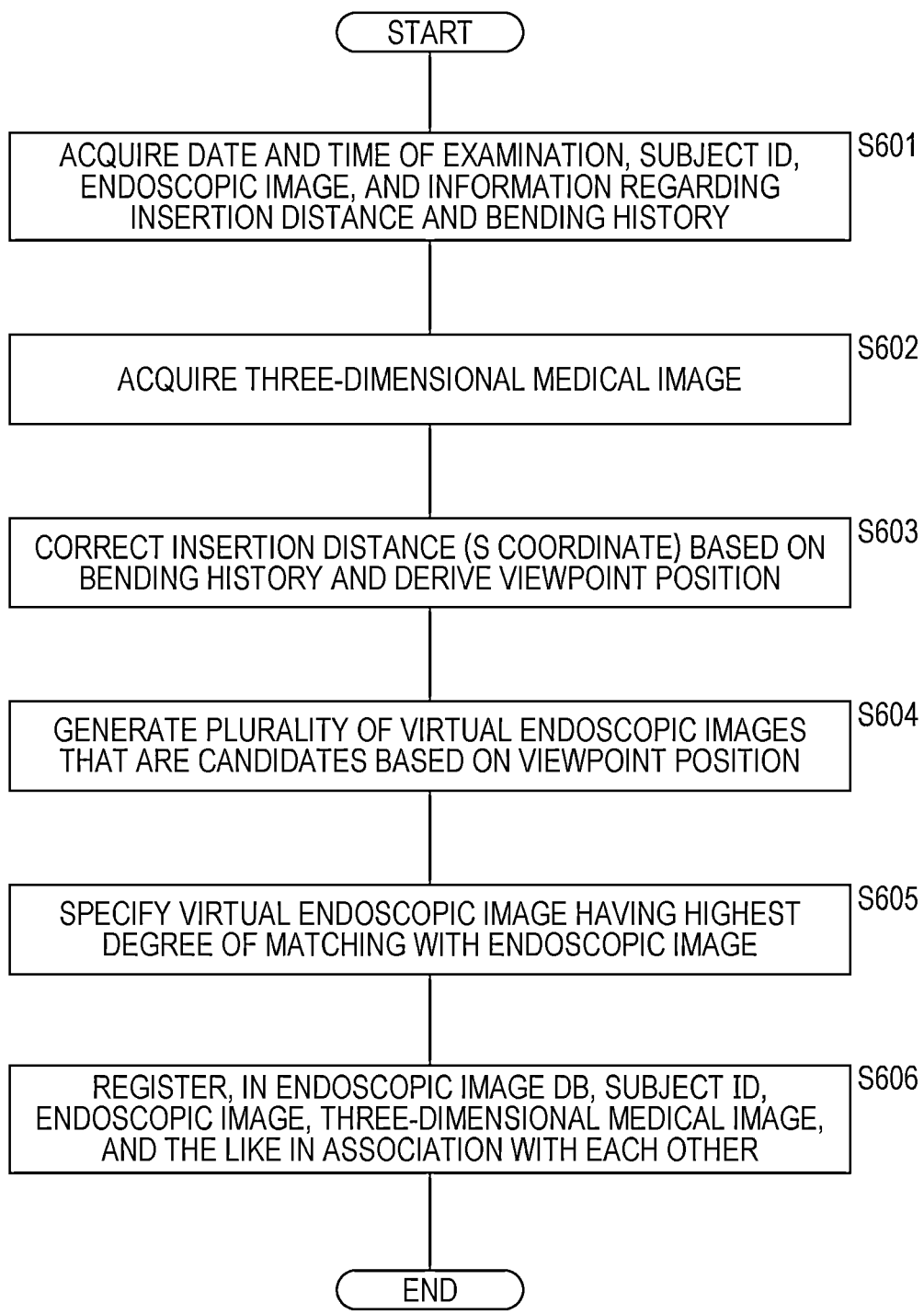
FIG. 31 is a flowchart illustrating an example of a processing procedure performed by the control unit of the information processing device.

FIG. 31 is a flowchart illustrating an example of a processing procedure performed by the control unit 62 of the information processing device 6. For example, the information processing device 6 starts the processing of the flowchart on the basis of a content input through the input unit 8 connected to the information processing device 6 itself.

The control unit 62 of the information processing device 6 acquires a date of examination, a subject ID, the endoscopic image, and the information regarding the insertion distance and the bending history output from the processor 120 for an endoscope (S601). Similarly to the fifth embodiment, the control unit 62 of the information processing device 6 acquires the endoscopic image and the like from the processor 120 for an endoscope, and further acquires, for example, the information regarding the bending history detected by the endoscope position detection device via the processor 120 for an endoscope. Alternatively, the control unit 62 of the information processing device 6 may directly acquire the information regarding the bending history from the endoscope position detection device.

The control unit 62 of the information processing device 6 acquires the three-dimensional medical image output from another examination device such as a CT device or an MRI device (S602). The control unit 62 of the information processing device 6 performs the processing of S602 similarly to the processing of S502 of the fifth embodiment.

The control unit 62 of the information processing device 6 corrects the insertion distance (S coordinate) on the basis of the bending history output from the processor 120 for an endoscope and derives the viewpoint position (S603). The control unit 62 derives the shape of the insertion portion 144 (for example, being bent to the right at 30 degrees or the like) by arithmetic processing according to the bending angle and the bending direction included in the bending history, and recalculates (corrects) the S coordinate, which is the insertion distance, on the basis of the derived shape of the insertion portion 144. The control unit 62 derives the viewpoint position on the basis of the corrected insertion distance (S coordinate) similarly to the fifth embodiment.

The control unit 62 of the information processing device 6 generates a plurality of candidate virtual endoscopic images on the basis of the viewpoint position (S604). The control unit 62 of the information processing device 6 specifies a virtual endoscopic image having the highest degree of matching with the endoscopic image among the plurality of generated virtual endoscopic images (S605). The control unit 62 of the information processing device 6 registers, in the endoscopic image DB 631, the date of examination, the subject ID, the endoscopic image, the insertion distance (S coordinate), the three-dimensional medical image, the viewpoint position, the viewpoint direction, and the virtual endoscopic image having the highest degree of matching in association with each other (S606). The control unit 62 of the information processing device 6 performs the processing of S604, S605, and S606 similarly to the processing of S504, S505, and S506 of the fifth embodiment.

Seventh Embodiment

Figure 32:
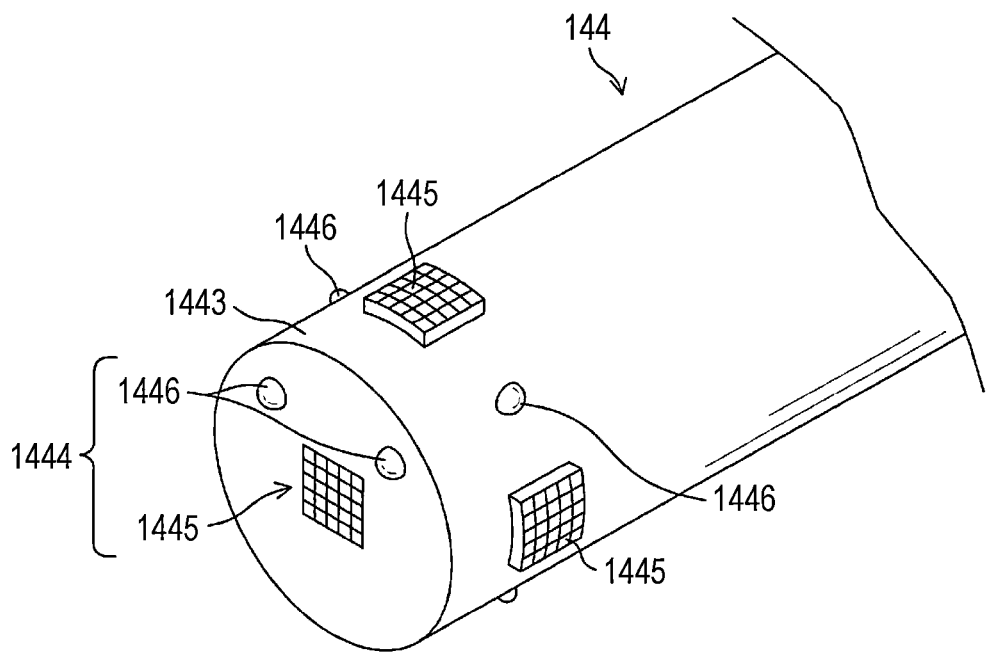
FIG. 32 is a perspective view schematically illustrating a distal tip of an insertion portion according to a seventh embodiment.
Figure 33:
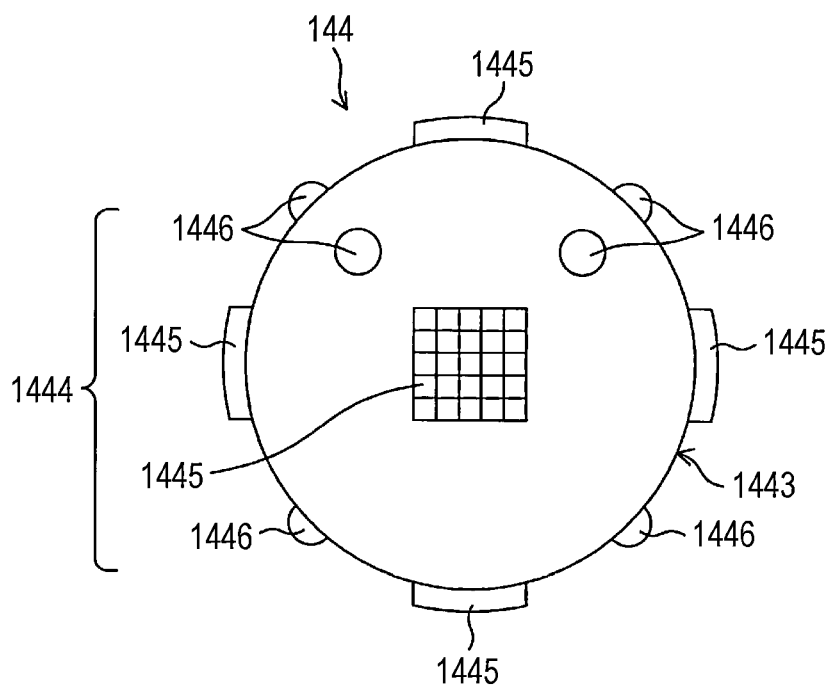
FIG. 33 is a front view schematically illustrating the distal tip of the insertion portion.

An information processing device 6 of the seventh embodiment is different from that of the fifth embodiment in that a plurality of endoscopic images captured by an endoscope including a plurality of image sensors 1445 are acquired from a processor 120 for an endoscope. FIG. 32 is a perspective view schematically illustrating a distal tip of an insertion portion 144 according to the seventh embodiment. FIG. 33 is a front view schematically illustrating the distal tip of the insertion portion 144 according to the seventh embodiment. The plurality of image sensors 1445 and a plurality of image capturing light sources 1446 are provided at a distal tip portion 1443 of the endoscope 140, and configure an image capturing unit 1444.

The plurality of image sensors 1445 includes image sensors 1445 (four image sensors in the drawings) arranged at equal intervals along a circumferential direction on an outer circumferential surface of a cylindrical body at the distal tip portion 1443, and an image sensor 1445 (one image sensor in the drawings) provided on an end surface of the cylindrical body at the distal tip portion 1443. The image sensor 1445 provided on the end surface of the cylindrical body at the distal tip portion 1443 captures an image of a front area in an insertion direction of the endoscope 140. Each of the plurality of image sensors 1445 provided on the outer circumferential surface of the cylindrical body at the distal tip portion 1443 captures an image of a side area in the insertion direction of the endoscope 140. That is, each of the plurality of image sensors 1445 provided on the outer circumferential surface of the cylindrical body at the distal tip portion 1443 can capture an image of an intracorporeal site positioned behind an intracorporeal site whose image is captured by the image sensor 1445 provided on the end surface of the cylindrical body at the distal tip portion 1443 in the insertion direction of the endoscope 140.

The plurality of image capturing light sources 1446 include an image capturing light source 1446 (four image capturing light sources in the drawings) arranged at equal intervals along the circumferential direction on the outer circumferential surface of the cylindrical body at the distal tip portion 1443, and an image capturing light source 1446 (two image capturing light sources in the drawings) provided on the end surface of the cylindrical body at the distal tip portion 1443. That is, since the plurality of image capturing light sources 1446 are provided corresponding to the image sensor 1445 provided on the end surface of the cylindrical body at the distal tip portion 1443 and the plurality of image sensors 1445 provided on the outer circumferential surface of the cylindrical body at the distal tip portion 1443, respectively, it is possible to supply a sufficient quantity of light when the plurality of image sensors 1445 captures an image of an intracorporeal site.

By providing the plurality of image sensors 1445 on the outer circumferential surface of the cylindrical body and the end surface of the cylindrical body at the distal tip portion 1443 in this manner, it is possible to acquire a plurality of endoscopic images obtained in a plurality of different viewpoint directions at a single viewpoint position.

Figure 34:
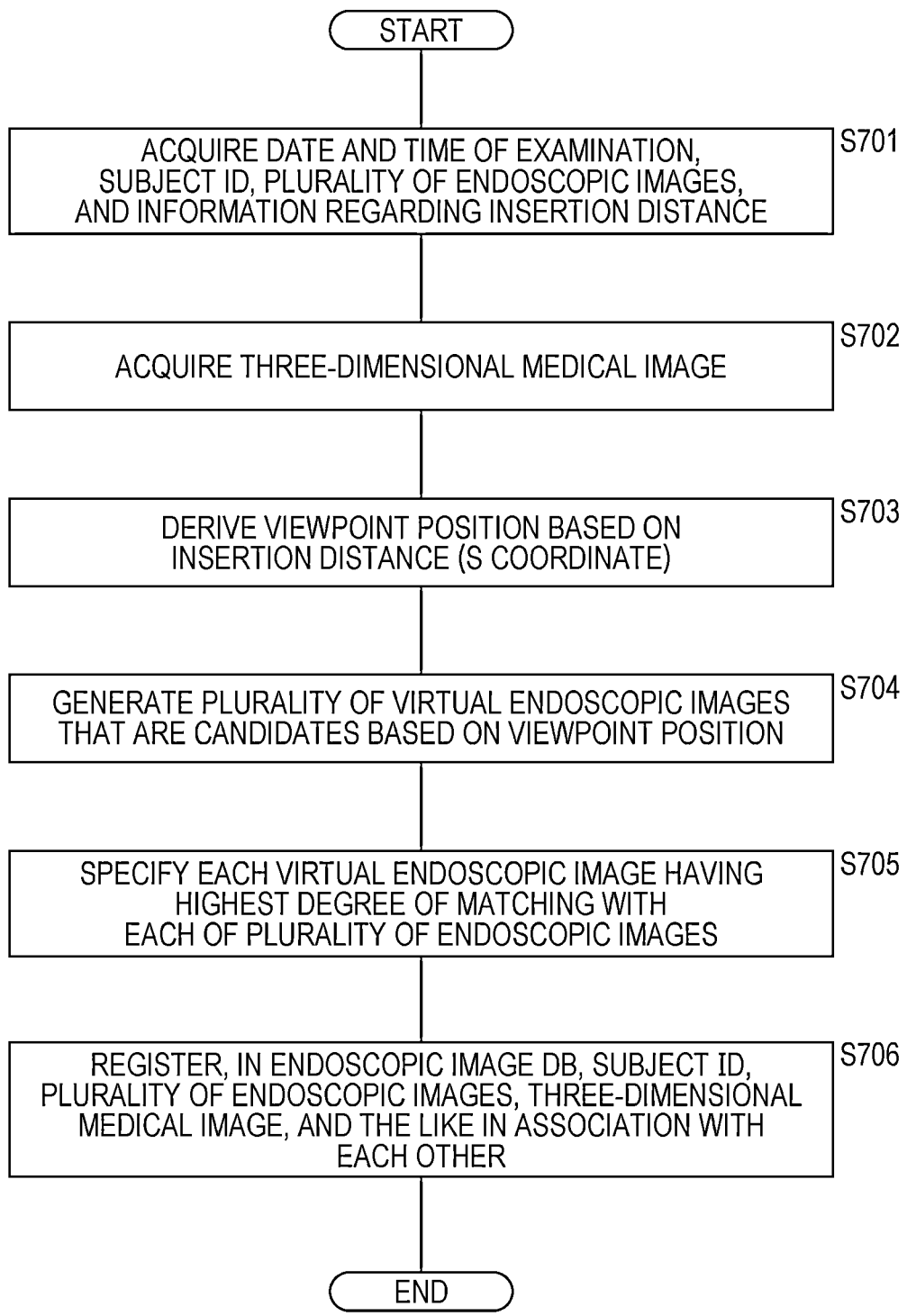
FIG. 34 is a flowchart illustrating an example of a processing procedure performed by a control unit of an information processing device.

FIG. 34 is a flowchart illustrating an example of a processing procedure performed by a control unit 62 of the information processing device 6. For example, the information processing device 6 starts the processing of the flowchart on the basis of a content input through the input unit 8 connected to the information processing device 6 itself.

The control unit 62 of the information processing device 6 acquires a date of examination, a subject ID, the plurality of endoscopic images, and information regarding an insertion distance output from the processor 120 for an endoscope (S701). The control unit 62 acquires the date of examination, the subject ID, the plurality of endoscopic images, and the information regarding the insertion distance as in the fifth embodiment. In the present embodiment, since the plurality of image sensors 1445 are provided at the distal tip portion 1443 of the insertion portion 144 in the endoscope 140, the processor 120 for an endoscope outputs the plurality of endoscopic images obtained in different viewpoint directions at the same viewpoint position (the position of the endoscope 140 in the body). Therefore, the control unit 62 of the information processing device 6 acquires the plurality of endoscopic images obtained at the same viewpoint position in different viewpoint directions from the processor 120 for an endoscope.

By acquiring the plurality of endoscopic images obtained at the same viewpoint position in different viewpoint directions, it is possible to capture an endoscopic image including an intracorporeal site positioned behind the distal tip portion 1443 of the insertion portion 144 in the endoscope 140 in the insertion direction of the insertion portion 144. Therefore, the control unit 62 of the information processing device 6 can acquire a plurality of endoscopic images each including intracorporeal sites positioned on the front side or back side in the insertion direction of the insertion portion 144.

The control unit 62 of the information processing device 6 acquires a three-dimensional medical image output from another examination device such as a CT device or an MRI device (S702). The control unit 62 of the information processing device 6 derives the viewpoint position on the basis of the insertion distance (S coordinate) (S703). The control unit 62 of the information processing device 6 performs the processing of S702 and S703 similarly to the processing of S502 and S503 of the fifth embodiment.

The control unit 62 of the information processing device 6 generates a plurality of candidate virtual endoscopic images on the basis of the viewpoint position (S704). The control unit 62 of the information processing device 6 specifies a virtual endoscopic image having the highest degree of matching with each of the plurality of endoscopic images among the plurality of generated virtual endoscopic images (S705). The control unit 62 of the information processing device 6 performs the processing of S704 and S705 similarly to the processing of S504 and S505 of the fifth embodiment. In the present embodiment, the control unit 62 of the information processing device 6 acquires a plurality of endoscopic images obtained at the same viewpoint position in different viewpoint directions from the processor 120 for an endoscope. Therefore, the control unit 62 compares each of the acquired plurality of endoscopic images with a plurality of virtual endoscopic images generated by changing the viewpoint direction (rotation angles) by a predetermined angle on the basis of the viewpoint position, and specifies each virtual endoscopic image that matches most with (that has the highest degree of matching with) each of the plurality of endoscopic images, that is, each virtual endoscopic image having the smallest difference amount. The control unit 62 specifies the virtual endoscopic image having the highest degree of matching and a viewpoint direction (rotation angles) at the time of generating the virtual endoscopic image for each of the plurality of acquired endoscopic images.

The control unit 62 of the information processing device 6 registers, in the endoscopic image DB 631, the date of examination, the subject ID, the plurality of endoscopic images, the insertion distance (S coordinate), the three-dimensional medical image, the viewpoint position, the viewpoint direction corresponding to each of the plurality of endoscopic images, and the virtual endoscopic images in association with each other (S706). The control unit 62 of the information processing device 6 performs the processing of S706 similarly to the processing of S506 of the fifth embodiment.

In the present embodiment, a plurality of endoscopic images obtained at the same viewpoint position in different viewpoint directions are registered in the endoscopic image DB 631. The control unit 62 of the information processing device 6 registers, in the endoscopic image DB 631, each of the plurality of endoscopic images, each virtual endoscopic image that matches most with each endoscopic image, and each viewpoint direction used to generate the virtual endoscopic image in association with each other. Since the endoscopic images include a plurality of endoscopic images captured by the plurality of image sensors 1445, a plurality of endoscopic images obtained at different image capturing angles (viewpoint directions) and the same image capturing point (viewpoint position) can be acquired. Since the plurality of endoscopic images obtained at different image capturing angles (viewpoint directions) and the three-dimensional medical image are stored in association with each other on the basis of the same image capturing point (viewpoint position), it is possible to provide the group of images to an operator of the endoscope 140 such as a doctor and to more efficiently support diagnosis for the doctor or the like.

Eighth Embodiment

Figure 35:
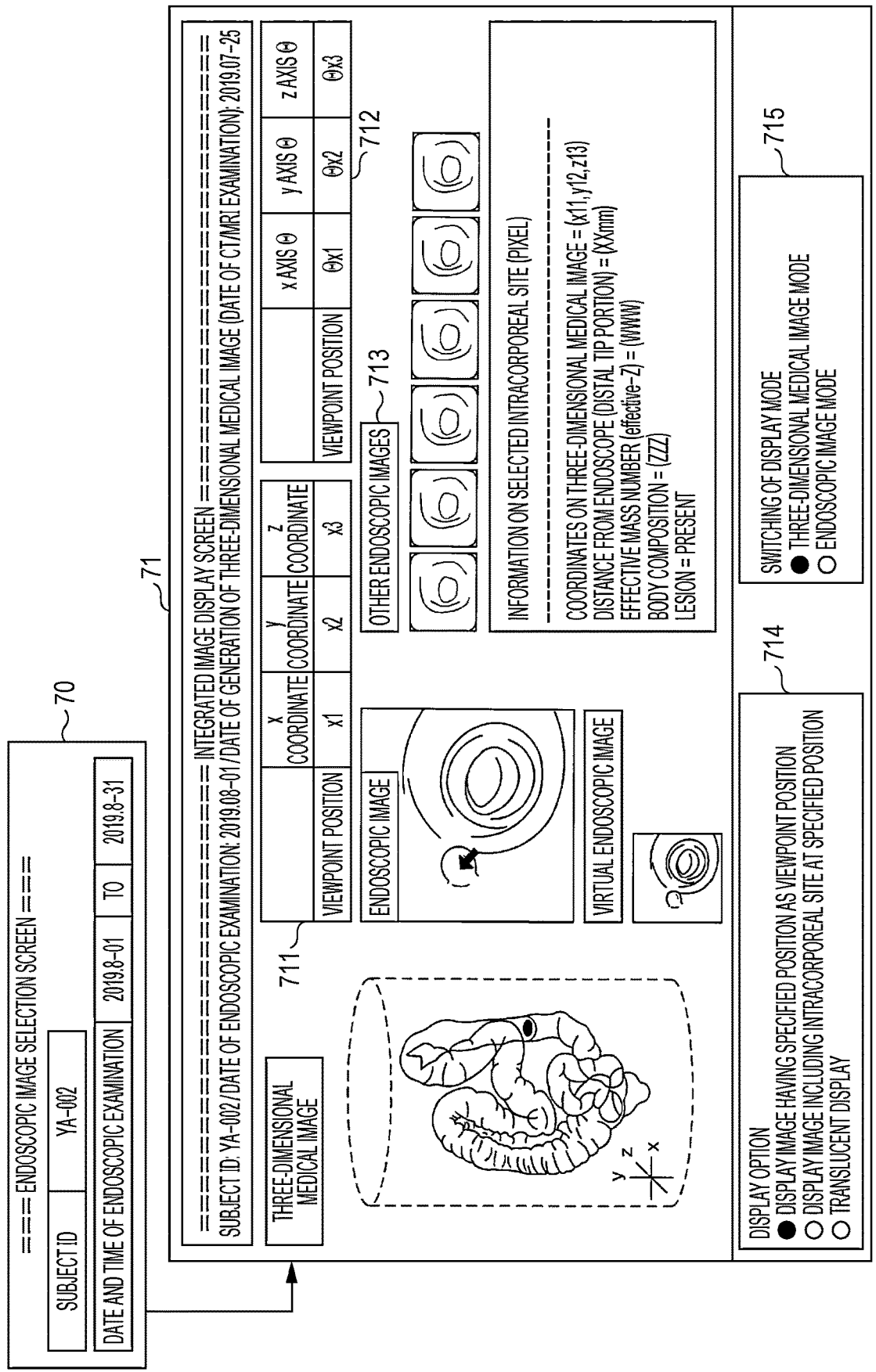
FIG. 35 is an explanatory view illustrating one mode (three-dimensional medical image mode) of an integrated image display screen according to an eighth embodiment.
Figure 36:
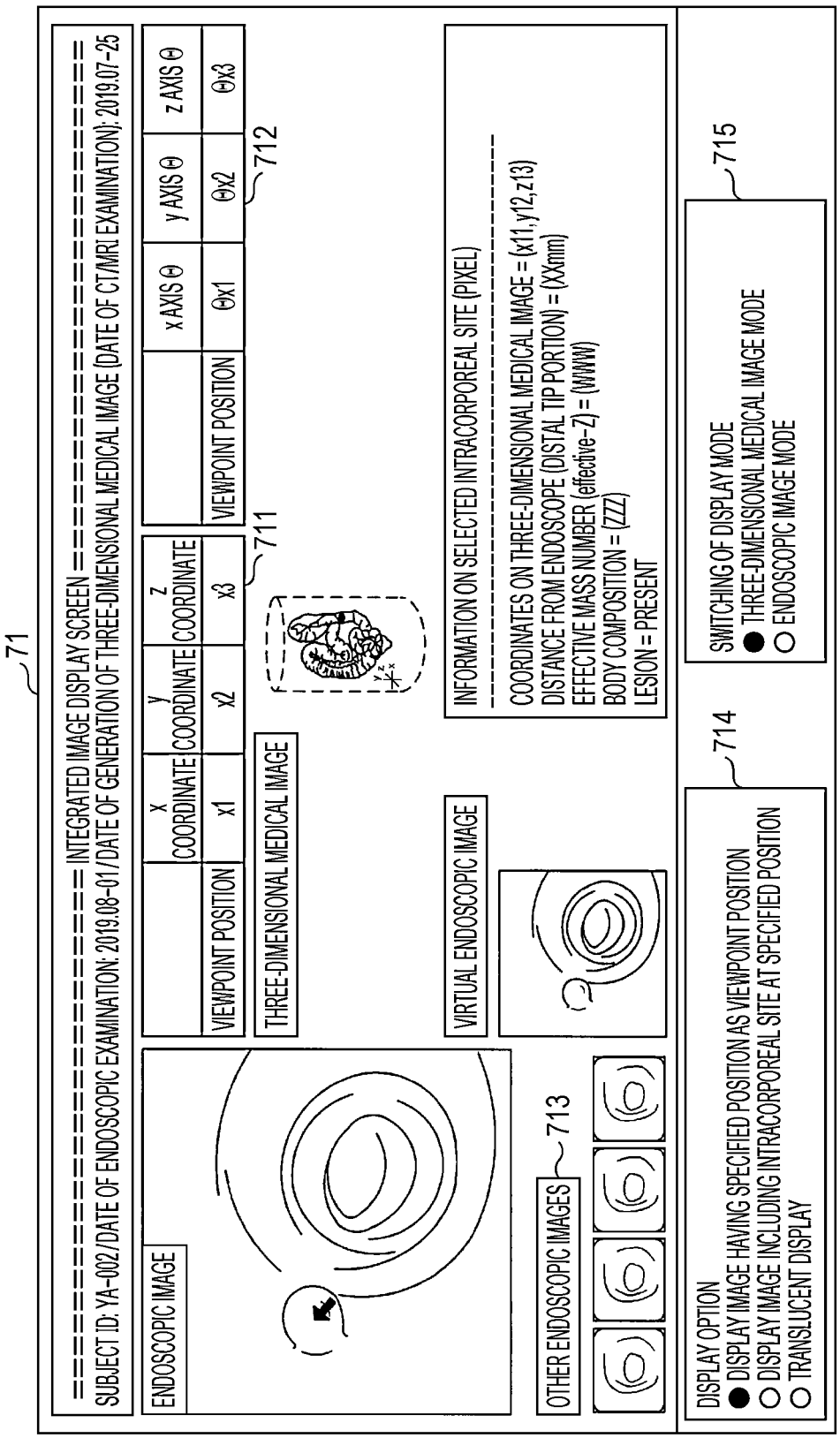
FIG. 36 is an explanatory view illustrating one mode (endoscopic image mode) of the integrated image display screen.

An information processing device 6 of the eighth embodiment uses various data registered in an endoscopic image DB 631 to display a screen (integrated image display screen 71) in which an endoscopic image and a three-dimensional medical image are associated with each other, thereby providing diagnosis support information to a doctor or the like. FIG. 35 is an explanatory view illustrating one mode (three-dimensional medical image mode) of the integrated image display screen 71 according to the eighth embodiment. FIG. 36 is an explanatory view illustrating one mode (endoscopic image mode) of the integrated image display screen 71.

A control unit 62 of the information processing device 6 searches the endoscopic image DB 631 stored in the storage unit 63, generates screen data for configuring the display screen (integrated image display screen 71), outputs the screen data to a display unit 7, and displays the display screen (integrated image display screen 71) on the display unit 7.

In displaying the integrated image display screen 71, the information processing device 6 displays an endoscopic image selection screen 70 as illustrated in FIG. 35, for example, and receives information serving as a search key such as a subject ID for searching the endoscopic image DB 631. On the endoscopic image selection screen 70, for example, an input field for receiving a subject ID and a date of endoscopic examination of a subject is arranged. The information processing device 6 searches the endoscopic image DB 631 on the basis of the subject ID and the like input through the endoscopic image selection screen 70, and displays the integrated image display screen 71 including data of the search result on the display unit 7.

The integrated image display screen 71 includes, for example, a region for displaying a bibliographic item such as the subject ID, a region for displaying the three-dimensional medical image, a region for displaying the endoscopic image, a region for displaying a virtual endoscopic image, a region for displaying a viewpoint position at which the endoscopic image is captured, or the like, and a region for displaying information on an intracorporeal site (pixel) selected in the endoscopic image.

In the region for displaying the bibliographic item such as the subject ID, the bibliographic item in data management such as the subject ID, the date of endoscopic examination, a date of generation of the three-dimensional medical image, and the like used to search the endoscopic image DB 631 are displayed.

In the region for displaying the three-dimensional medical image, an intracorporeal site such as a digestive organ appearing in the three-dimensional medical image is displayed as a three-dimensional object, and the three-dimensional object can be rotated by dragging any part of the three-dimensional object. The three-dimensional medical image may be displayed in a state where the position of a lesion specified in the endoscopic image is highlighted, for example.

In the region for displaying the endoscopic image, for example, an endoscopic image corresponding to a position selected by a mouse or the like on the three-dimensional medical image is displayed. That is, the position selected by the mouse or the like on the three-dimensional medical image corresponds to coordinates in a coordinate system of the three-dimensional medical image. Therefore, the information processing device 6 searches the endoscopic image DB 631 for an endoscopic image obtained at a viewpoint position corresponding to the coordinates or an endoscopic image including the intracorporeal site corresponding to the coordinates, and displays the endoscopic image in the region for displaying the endoscopic image. In a case where a plurality of endoscopic images are searched (extracted) in the endoscopic image DB 631 on the basis of the coordinates, one of the endoscopic images may be selected and displayed on the basis of the presence or absence of a lesion included in the endoscopic image or a feature amount, and other endoscopic images may be displayed as thumbnails. That is, a thumbnail display field 713 is arranged in the region for displaying the endoscopic image, and other endoscopic images are displayed as thumbnails in the thumbnail display field 713.

In the region for displaying the virtual endoscopic image, a virtual endoscopic image having the highest degree of matching with the endoscopic image displayed in the region for displaying the endoscopic image is displayed. As described above, since the endoscopic image and the virtual endoscopic image having the highest degree of matching with the endoscopic image are stored in the same record, it is possible to efficiently extract the virtual endoscopic image by using the endoscopic image DB 631.

The position (viewpoint position) and the viewpoint direction (rotation angles) of the endoscope 140 in the body at the time point when the endoscopic image displayed in the region for displaying the endoscopic image is captured are displayed in the region for displaying the viewpoint position at which the endoscopic image is captured or the like. That is, a viewpoint position field 711 and a viewpoint direction field 712 are arranged in the region for displaying the viewpoint position at which the endoscopic image is captured or the like, and the viewpoint position is displayed in the viewpoint position field 711 and the viewpoint direction is displayed in the viewpoint direction field 712.

The region for displaying the viewpoint position at which the endoscopic image is captured or the like may function as an input field (the viewpoint position field 711 and the viewpoint direction field 712) to which an arbitrary viewpoint position and an arbitrary viewpoint direction are input. The endoscopic image DB 631 may be searched using the viewpoint position input in the viewpoint position field 711 and the viewpoint direction input in the viewpoint direction field 712, an endoscopic image corresponding to the viewpoint position and the viewpoint direction may be extracted, and the endoscopic image may be displayed in the region for displaying the endoscopic image.

In the region for displaying the information on the intracorporeal site (pixel) selected in the endoscopic image, coordinates of the intracorporeal site (pixel) selected by the mouse or the like in the endoscopic image on the three-dimensional medical image and a distance between the intracorporeal site (pixel) and a distal tip portion 1443 of the endoscope 140 are displayed. The endoscopic image and the virtual endoscopic image having the highest degree of matching with the endoscopic image show a region of the same intracorporeal body, and each pixel of the endoscopic image and each pixel of the virtual endoscopic image substantially match each other or can be regarded as being the same in the coordinate system in both images, and thus each pixel of the endoscopic image and each pixel of the virtual endoscopic image correspond to each other. Since the virtual endoscopic image is generated by projecting the three-dimensional medical image or the like, each pixel of the virtual endoscopic image corresponds to the coordinates on the three-dimensional medical image. Therefore, it is possible to specify the coordinates of the intracorporeal site (pixel) in the coordinate system of the three-dimensional medical image on the basis of the intracorporeal site (pixel) included in the selected endoscopic image. As described above, since the viewpoint position, which is the position of the distal tip portion 1443 of the endoscope 140, is already registered in the DB registration unit 625, the distance between the distal tip portion 1443 of the endoscope 140 and the intracorporeal site (pixel) included in the selected endoscopic image can be derived on the basis of the coordinates of the intracorporeal site (pixel) in the coordinate system of the three-dimensional medical image and the viewpoint position.

In the region for displaying the information on the intracorporeal site (pixel) selected in the endoscopic image, an effective mass number (effective-Z) of the intracorporeal site (pixel) selected in the endoscopic image or information regarding a body composition such as fat or lactic acid may be displayed. Since the effective mass number and the like are attribute information added to each pixel of the three-dimensional medical image, the pixel of the three-dimensional medical image can be specified on the basis of the coordinates in the coordinate system of the three-dimensional medical image specified as described above, and the effective mass number and the like added to the pixel can be extracted and displayed.

In the integrated image display screen 71, for example, a display mode switching field 715 for switching a display mode and a display option field 714 for setting a display option are arranged in an input region including an input region for receiving an input related to a display mode.

The display mode switching field 715 includes a radio button or the like for switching between a three-dimensional medical image mode in which the three-dimensional medical image is mainly displayed and an endoscopic image mode in which the endoscopic image is displayed. The integrated image display screen 71 is configured to be switch between a plurality of display modes including the three-dimensional medical image mode (FIG. 35) in which the three-dimensional medical image is mainly displayed and the endoscopic image mode (FIG. 36) in which the endoscopic image is mainly displayed according to an input content in the display mode switching field 715. By making it possible to easily switch an image to be mainly displayed in this manner, it is possible to efficiently provide diagnosis support information to a doctor or the like.

The display option field 714 includes a radio button for switching between a setting for displaying an image having a specified position as the viewpoint position or a setting for displaying an image including an intracorporeal site at a specified position. According to the input content in the display mode switching field 715, a search condition for searching for an endoscopic image to be displayed in the region for displaying the endoscopic image is set, and the endoscopic image that satisfies the condition is displayed on the integrated image display screen 71. As described above, since the viewpoint position and the intracorporeal site (pixel) included in the endoscopic image are specified on the basis of the coordinates in the coordinate system of the three-dimensional medical image, the information processing device 6 can set the search condition set in the display option field 714 and search the endoscopic image DB 631.

The display option field 714 may include an option setting made by a radio button or the like for translucently displaying the three-dimensional medical image. When the three-dimensional medical image is configured as, for example, volume data from slice data output from a CT device, an MRI device, or the like, the three-dimensional medical image can be translucently displayed by being generated (translucent processing) in a transparent mode. In a case where the translucent display is set as the display option, the information processing device 6 displays the three-dimensional medical image processed to be translucent.

Figure 37:
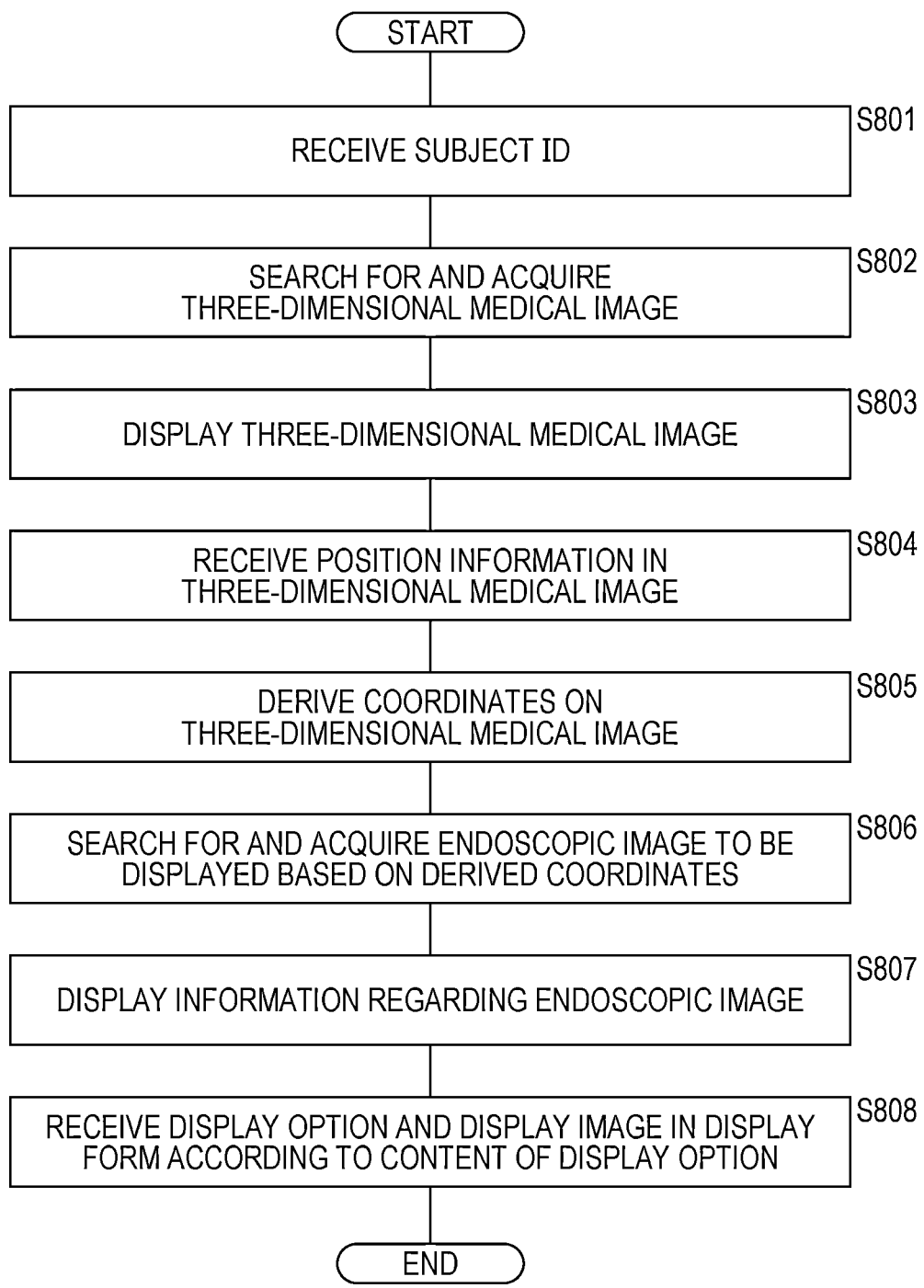
FIG. 37 is a flowchart illustrating an example of a processing procedure performed by a control unit of an information processing device.

FIG. 37 is a flowchart illustrating an example of a processing procedure performed by the control unit 62 of the information processing device 6. For example, the information processing device 6 starts the processing of the flowchart on the basis of a content input through the input unit 8 connected to the information processing device 6 itself.

The control unit 62 of the information processing device 6 receives the subject ID (S801). The control unit 62 acquires the subject ID by receiving the subject ID input on the endoscopic image selection screen by a doctor or the like. In a case where there is an input field in which the date of endoscopic examination is selected on the endoscopic image selection screen, the control unit 62 may receive information regarding the selected date of endoscopic examination and acquire information regarding the date such as a period.

The control unit 62 of the information processing device 6 searches for and acquires the three-dimensional medical image on the basis of the acquired subject ID (S802). The control unit 62 searches the endoscopic image DB 631 by using the acquired subject ID as a search key, and extracts and acquires the three-dimensional medical image corresponding to the subject ID.

The control unit 62 of the information processing device 6 displays the acquired three-dimensional medical image (S803). The control unit 62 displays the acquired three-dimensional medical image on the integrated image display screen 71.

The control unit 62 of the information processing device 6 receives position information in the three-dimensional medical image (S804). The control unit 62 receives the position information on the three-dimensional medical image selected by a click operation of a mouse performed by a doctor or the like on the integrated image display screen 71, for example.

The control unit 62 of the information processing device 6 derives coordinates on the three-dimensional medical image on the basis of the received position information on the three-dimensional medical image (S805).

The control unit 62 of the information processing device 6 searches for and acquires the endoscopic image to be displayed on the basis of the derived coordinates (S806). The control unit 62 searches the endoscopic image DB 631 by using the derived coordinates as the viewpoint position and using the viewpoint position as a search key, and extracts and acquires the corresponding endoscopic image. When searching for the endoscopic image by using the viewpoint position as a search key, the control unit 62 may search a predetermined range including the coordinates (derived coordinates) of the viewpoint position. By searching the predetermined range including the coordinates (derived coordinates) of the viewpoint position, it is possible to search for the endoscopic images corresponding to the predetermined range from the coordinates, and it is thus possible to efficiently search for one or more endoscopic image groups captured in the vicinity of the selected position on the three-dimensional medical image. The control unit 62 displays the extracted endoscopic image on the integrated image display screen 71. In a case where a plurality of endoscopic images are extracted, the control unit 62 may display, in the maximum size or on the foremost side, an endoscopic image having a high priority determined on the basis of the presence or absence of a lesion or the like among the plurality of extracted endoscopic images, and display other endoscopic images in the minimum size or on the back side.

The control unit 62 of the information processing device 6 displays information regarding the displayed endoscopic image (S807). The control unit 62 displays, for example, a virtual endoscopic image that matches most with the endoscopic image or information regarding an intracorporeal site (pixel) selected in the displayed endoscopic image as the information regarding the displayed endoscopic image. The information regarding the intracorporeal site (pixel) selected in the endoscopic image may include, for example, coordinates of the intracorporeal site (pixel) on the three-dimensional medical image and a distance from the distal tip portion 1443 of the endoscope 140 to the intracorporeal site (pixel). The information regarding the intracorporeal site (pixel) selected in the endoscopic image may include information regarding the effective mass number (effective-Z) or body composition which is information added to each pixel (intracorporeal site) of the three-dimensional medical image.

The control unit 62 of the information processing device 6 receives the display option selected on the integrated image display screen 71, and performs display in a display form corresponding to a content of the display option (S808). As described above, the input field for receiving the selection of the display option is arranged on the integrated image display screen 71, and the display mode of the integrated image display screen 71 is changed according to a content of the input display option.

According to the present embodiment, the endoscopic image, the three-dimensional medical image, and the virtual endoscopic image registered in the endoscopic image DB 631 in association with each other are listed and displayed on the integrated image display screen 71, whereby diagnosis support information obtained by integrating a group of medical data related to the subject can be provided to a doctor or the like.

In the present embodiment, the information processing device 6 displays the integrated image display screen 71 on the display unit 7, but the present invention is not limited thereto. The information processing device 6 may display the integrated image display screen 71 on a display device 50 of an endoscope device 110 via a processor 120 for an endoscope. Alternatively, a series of processing or an operation as a functional part related to the display of the integrated image display screen 71 or the like may be performed by the processor 120 for an endoscope as in the fifth embodiment. Alternatively, similarly to the fifth embodiment, the information processing device 6 and the processor 120 for an endoscope may perform a series of processing related to the display of the integrated image display screen 71 or the like in cooperation or may be operated as a functional part related to the display of the integrated image display screen 71 or the like in cooperation.

Ninth Embodiment

An information processing device 6 according to a ninth embodiment uses various data registered in an endoscopic image DB 631 to output diagnosis support information such as the presence or absence of a lesion related to an intracorporeal site included in an endoscopic image registered in the endoscopic image DB 631.

Figure 38:
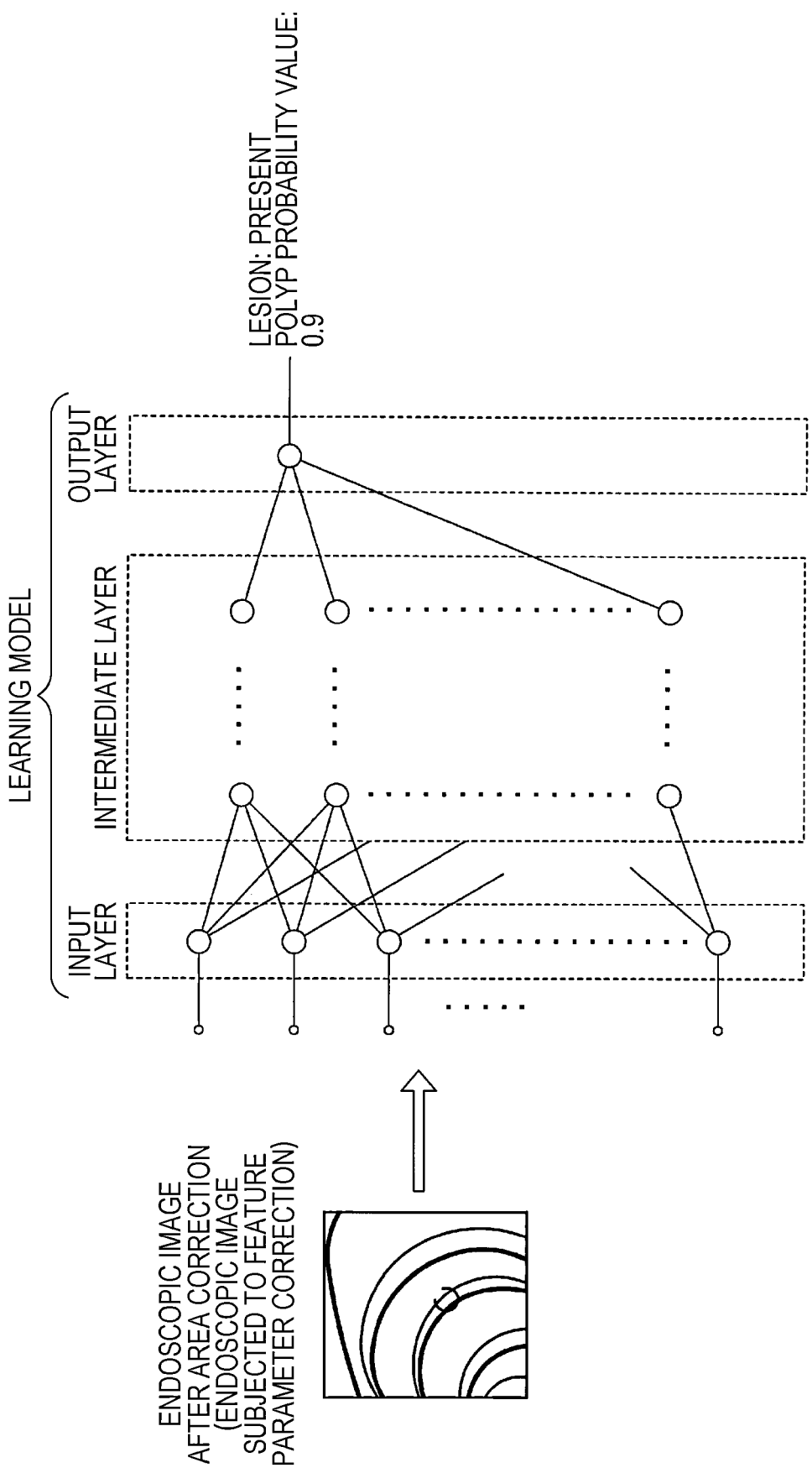
FIG. 38 is an explanatory diagram for describing processing of outputting diagnosis support information by using a learning model according to a ninth embodiment.

FIG. 38 is an explanatory diagram for describing processing of outputting the diagnosis support information by using a learning model 9 according to the ninth embodiment. The information processing device 6 constructs (generates) a neural network that receives the endoscopic image and outputs the diagnosis support information including the presence or absence of a lesion and the like by training the neural network on the basis of training data in which the endoscopic image is problem data and the diagnosis support information including at least one of the presence or absence of a lesion, the type of a symptom of the lesion, the stage of the symptom of the lesion, the location of the lesion, or the like is answer data. The endoscopic image includes, for example, an intracorporeal site suspected of being a lesion. The presence or absence of a lesion, the type of the symptom, the stage of the symptom, and the location of the lesion are information regarding the presence or absence or probability value of a lesion related to the intracorporeal site included in the endoscopic image, the type of the symptom, the stage of the symptom, and the location of the lesion.

The endoscopic image input to the learning model 9 may be an endoscopic image whose feature parameter has been corrected on the basis of distance image information derived from a virtual endoscopic image corresponding to the endoscopic image (a virtual endoscopic image that matches most with the endoscopic image). The correction of the feature parameter based on the distance image information will be described later.

The neural network (learning model 9) trained by using the training data is assumed to be used as a program module that is a part of artificial intelligence software. The learning model 9 is used in the information processing device 6 including a control unit 62 (a CPU or the like) and a storage unit 63 as described above, and is executed by the information processing device 6 having arithmetic processing capability, thereby configuring a neural network system. That is, the control unit 62 of the information processing device 6 is operated to perform an arithmetic operation of extracting the feature amount of the endoscopic image input to an input layer according to a command from the learning model 9 stored in the storage unit 63, and output the diagnosis support information including the presence or absence of a lesion from an output layer.

The input layer has a plurality of neurons that receive a pixel value of the endoscopic image, and transmits the input pixel value and distance information to an intermediate layer. The intermediate layer has a plurality of neurons that extract the image feature amount of the endoscopic image, and transfers the extracted image feature amount to the output layer. The output layer has one or more neurons that output information regarding the presence or absence of a lesion and the stage of a symptom, and outputs information regarding the presence or absence of a lesion and the stage of a symptom on the basis of the image feature amount output from the intermediate layer. For example, in a case where the learning model 9 is a convolutional neutral network (CNN), the intermediate layer has a configuration in which a convolutional layer that convolves the pixel value of each pixel input from the input layer and a pooling layer that maps (compresses) the pixel value convolved by the convolutional layer are alternately connected, and finally extracts the feature amount of the endoscopic image while compressing pixel information of the endoscopic image. The output layer has one or more neurons that output information regarding the presence or absence of a lesion related to the intracorporeal site included in the endoscopic image, and outputs information regarding the presence or absence of a lesion or the like on the basis of the image feature amount and the like output from the intermediate layer. The output information regarding the presence or absence of a lesion or the like is information used as the diagnosis support information by a doctor or the like operating the endoscope.

In the present embodiment, data input to the learning model 9 is described as the endoscopic image, but the present invention is not limited thereto. The data input to the learning model 9 may be a captured image (raw image) captured by an image sensor 1445 of the endoscope 140. That is, the learning model 9 may output the information regarding the presence or absence of a lesion or the like by receiving the captured image.

In the present embodiment, a case where the learning model 9 is a neural network (NN) such as a CNN is described, but the learning model 9 is not limited to the NN, and may be a learning model 9 constructed by another learning algorithm such as a support vector machine (SVM), a Bayesian network, or a regression tree. Alternatively, instead of the CNN, the learning model 9 may be a learning model that is generated using an arbitrary object detection algorithm such as regions with convolutional neural network (RCNN), fast RCNN, faster RCNN, single shot multibook detector (SSD), or You Only Look Once (YOLO).

The information processing device 6 compares the value output from the output layer with information (the presence or absence of a lesion and the stage of a symptom) labeled for the problem data (the endoscopic image), that is, a correct answer value (answer data), and optimizes a parameter used for the arithmetic processing in the intermediate layer so that the output value from the output layer approaches the correct answer value. The parameter is, for example, a weight (coupling coefficient) between neurons, a coefficient of an activation function used in each neuron, or the like. The parameter optimization method is not particularly limited, but for example, the information processing device 6 optimizes various parameters using backpropagation. The information processing device 6 performs the above-described processing on the endoscopic image included in the training data, generates the learning model 9, and stores the generated learning model 9 in the storage unit 63.

The endoscopic image (problem data) used as the training data and the information (answer data) regarding the presence or absence of a lesion or the like correlated with this information are stored in a large amount as the result data of the endoscopic examination performed in each medical institution, and it is possible to generate a large amount of training data for training the learning model 9 by using the result data.

Figure 39:
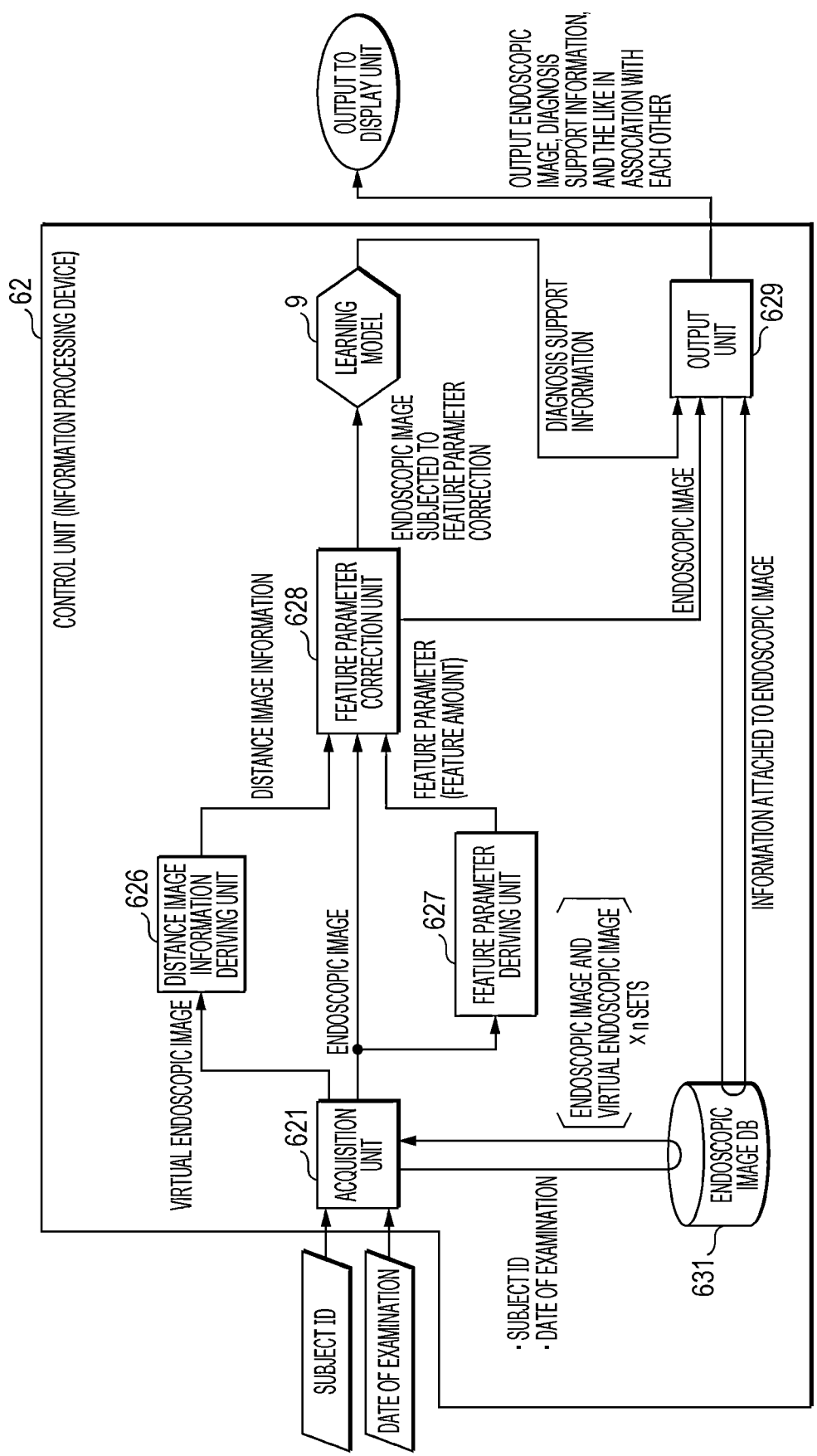
FIG. 39 is a functional block diagram illustrating functional parts included in a control unit of an information processing device.

FIG. 39 is a functional block diagram illustrating functional parts included in the control unit 62 of the information processing device 6. The control unit 62 of the information processing device 6 executes a program P stored in the storage unit 63 to function as an acquisition unit 621, a distance image information deriving unit 626, a feature parameter deriving unit 627, a feature parameter correction unit 628, and an output unit 629. The control unit 62 executes the program P stored in the storage unit 63 or reads an entity file constituting the learning model 9 to function as the learning model 9.

The acquisition unit 621 receives a subject ID and a date of examination input through an endoscopic image selection screen 70 or the like, and acquires the subject ID and the like. The acquisition unit 621 searches the endoscopic image DB 631 by using the acquired subject ID or the subject ID and the date of examination as a search key, and acquires a plurality of data sets including the endoscopic image and the virtual endoscopic image that matches most with the endoscopic image.

The acquisition unit 621 outputs the virtual endoscopic image to the distance image information deriving unit 626. The distance image information deriving unit 626 derives the distance image information on the basis of the acquired virtual endoscopic image. The distance image information is information regarding a distance between pixels in the virtual endoscopic image. The distance between the pixels means a distance in a coordinate system (a coordinate system in the body) of a three-dimensional medical image, and is, for example, a distance considering a depth in two intracorporeal sites included in the virtual endoscopic image. The virtual endoscopic image is an image obtained by projecting the three-dimensional medical image and converting the three-dimensional medical image into a two-dimensional image, an arbitrary point in the virtual endoscopic image corresponds to a point in the three-dimensional medical image, and these points indicate the same position in the intracorporeal site. The arbitrary point in the virtual endoscopic image may be a pixel number (pixel coordinates) that is a minimum unit in the image, or may be, for example, a central portion of a local region (a region including a plurality of pixels) that specifies a predetermined intracorporeal site. By determining two arbitrary points in this manner, a distance between the two points in the coordinate system of the three-dimensional medical image can be derived. That is, the distance in the distance image information corresponds to the distance between two points in the coordinate system of the three-dimensional medical image corresponding to two points in the virtual endoscopic image.

Two points in the three-dimensional medical image are specified from two points in the virtual endoscopic image. The distance between two points and vectors of two points can be derived on the basis of the coordinate values of the specified two points in the three-dimensional medical image. By applying the derived distance between two points and the derived vectors of two points in the three-dimensional medical image to the virtual endoscopic image as the distance between two points and vectors of two points of the virtual endoscopic image corresponding to the two points, it is possible to generate a distance image, that is, a virtual endoscopic image (distance image) to which distance information in the coordinate system of the three-dimensional medical image is added in the virtual endoscopic image. The distance image information deriving unit 626 may output the virtual endoscopic image (distance image) to which the information regarding the distance between the respective pixels is added as the distance image information.

The endoscopic image corresponds to the virtual endoscopic image constructed from the three-dimensional medical image on the basis of a position (viewpoint position) and an image capturing direction (viewpoint direction) of the endoscope 140 that has captured the endoscopic image. Therefore, the distance image information based on the virtual endoscopic image corresponding to the endoscopic image can also be applied to the endoscopic image. That is, a distance between two points in the endoscopic image corresponds to the distance (the distance in the distance image, and the distance in the coordinate system of the three-dimensional medical image) between two points in the virtual endoscopic image corresponding to the endoscopic image. Therefore, by applying the distance image information included in the distance image to the endoscopic image, the distance information such as a distance between intracorporeal sites included in the endoscopic image and the size of the intracorporeal site can be determined.

The acquisition unit 621 outputs the endoscopic image to the feature parameter deriving unit 627. The feature parameter deriving unit 627 derives a region of a predetermined intracorporeal site included in the endoscopic image as a feature parameter. For example, the feature parameter deriving unit 627 may derive a region of a predetermined intracorporeal site included in the endoscopic image as the feature parameter by using pattern recognition, edge detection, or the like. Alternatively, the feature parameter deriving unit 627 may derive, as the feature parameter, a region of a predetermined intracorporeal site included in the endoscopic image by using a local feature parameter extraction method such as accelerated KAZE (A-KAZE) or scale invariant feature transform (SIFT) on the basis of a change in hue or folds of the intracorporeal site in the endoscopic image.

The feature parameter correction unit 628 acquires the distance image information output from the distance image information deriving unit 626, the feature parameter output from the feature parameter deriving unit 627, and the endoscopic image output from the acquisition unit 621. The feature parameter correction unit 628 generates an endoscopic image whose feature parameter has been corrected by the distance image information on the basis of the acquired distance image information, feature parameter, and endoscopic image, and outputs the endoscopic image to the learning model 9.

In the correction performed by the feature parameter correction unit 628, for example, the area of the region of the predetermined intracorporeal site specified as the feature parameter is corrected (area correction processing). In performing the area correction processing, the feature parameter correction unit 628 acquires a distance R (for example, r1 or r2) to each image region of the corresponding endoscopic image on the basis of the distance image information obtained from the virtual endoscopic image. The feature parameter correction unit 628 compares the acquired distance to each image region with a reference distance (for example, 20 mm). The feature parameter correction unit 628 performs correction with an inverse square ratio $(R/20)^2$ "^: a power" to the compared distance R to each region. In a case where it is determined that the distance to the image region of the endoscopic image is equal to or more than the reference distance (the distance to the pixel is long), the feature parameter correction unit 628 performs enlargement processing on the image region by correcting the number of pixels constituting the image region with the inverse square ratio $(R/20)^2$ with respect to the distance R to each region. In a case where it is determined that the distance to the image region of the endoscopic image is less than the reference distance (the distance to the pixel is short), the feature parameter correction unit 628 performs contraction processing on the image region by correcting and reducing the number of pixels constituting the image region by the inverse square ratio $(R/20)^2$ with respect to the distance R to each region. In addition, in a case where there is a difference in distance between the respective pixels in each image region, correction is performed assuming that each image region is placed at the reference distance. Alternatively, the feature parameter correction unit 628 may perform the area correction processing by using nearest-neighbor interpolation, bilinear interpolation, bicubic interpolation, Lanczos interpolation, or the like. The feature parameter correction unit 628 performs the area correction processing on the endoscopic image by using these various methods, and outputs the corrected endoscopic image to the learning model 9.

The learning model 9 acquires the corrected endoscopic image and outputs diagnosis support information including the presence or absence of a lesion in the intracorporeal site included in the endoscopic image to the output unit 629. The output unit 629 acquires the diagnosis support information including the presence or absence of a lesion and the like from the learning model 9, and acquires the endoscopic image, the subject ID, and the like from the feature parameter correction unit 628 or the acquisition unit 621. The output unit 629 may acquire the endoscopic image whose feature parameter has been corrected from the feature parameter correction unit 628. The output unit 629 may search the endoscopic image DB 631 on the basis of the endoscopic image and acquire relevant information such as the viewpoint position of the endoscopic image.

The output unit 629 outputs the diagnosis support information including the presence or absence of a lesion and the like acquired from the learning model 9 to a display unit 7 in association with the endoscopic image that is a target of the diagnosis support information. The output unit 629 may output both the corrected endoscopic image input to the learning model 9 and the endoscopic image before the correction to the display unit 7. The output unit 629 may output the diagnosis support information and the three-dimensional medical image associated with the endoscopic image that is the target of the diagnosis support information to the display unit 7 in association with each other. When the diagnosis support information and the three-dimensional medical image are output to the display unit 7 in association with each other, the output unit 629 may output the diagnosis support information and the three-dimensional medical image so as to be displayed on the display unit 7 in a state where the position of the lesion in the three-dimensional medical image is highlighted, for example.

The output unit 629 may register, in the endoscopic image DB 631, the diagnosis support information including the presence or absence of a lesion and the like acquired from the learning model 9 and the endoscopic image that is the target of the diagnosis support information in association with each other. The output unit 629 may register, in the endoscopic image DB 631, both the corrected endoscopic image input to the learning model 9 and the endoscopic image before the correction. The output unit 629 may acquire the distance image information (distance image) from the distance image information deriving unit 626, and register, in the endoscopic image DB 631, the distance image information in association with the endoscopic image.

Figure 40:
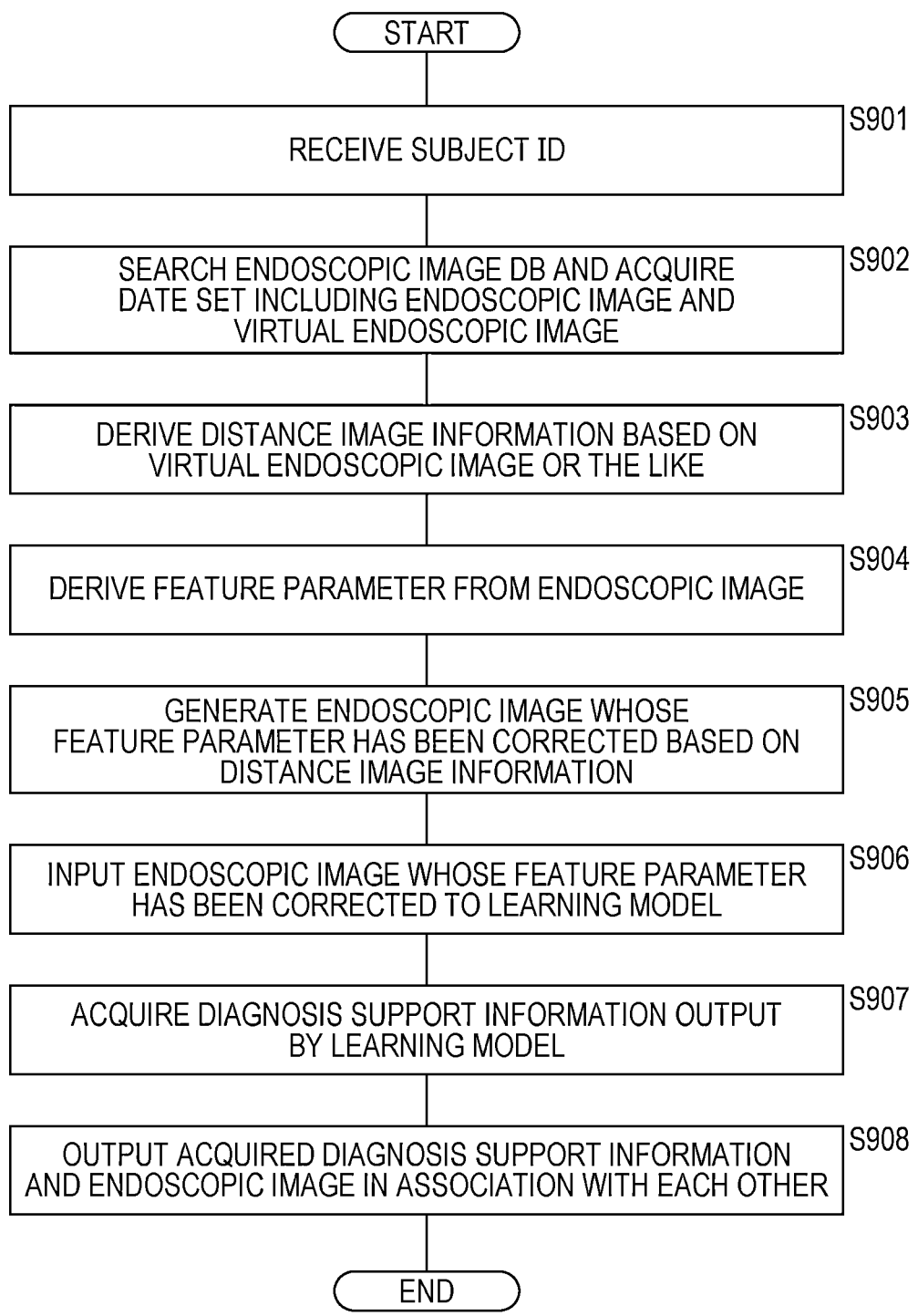
FIG. 40 is a flowchart illustrating an example of a processing procedure performed by the control unit of the information processing device.

FIG. 40 is a flowchart illustrating an example of a processing procedure performed by the control unit 62 of the information processing device 6. For example, the information processing device 6 starts the processing of the flowchart on the basis of a content input through the input unit 8 connected to the information processing device 6 itself.

The control unit 62 of the information processing device 6 acquires the subject ID (S901). The control unit 62 may acquire examination date information such as a period for specifying the date of endoscopic examination in addition to the subject ID.

The control unit 62 of the information processing device 6 searches the endoscopic image DB 631 on the basis of the subject ID, and acquires a data set including an endoscopic image and a virtual endoscopic image (S902). The control unit 62 searches the endoscopic image DB 631 on the basis of the acquired subject ID or the subject ID and the examination date information, and acquires the endoscopic image and the virtual endoscopic image extracted using the subject ID or the like.

In a case where there are a plurality of endoscopic images extracted using the subject ID or the like, there are also a plurality of virtual endoscopic images (virtual endoscopic images registered in the same record as the endoscopic images) corresponding to the endoscopic images, respectively. The control unit 62 may acquire the plurality of endoscopic images and virtual endoscopic images as a plurality of data sets (endoscopic images and virtual endoscopic images). One data set includes one endoscopic image and one virtual endoscopic image, and the control unit 62 may perform the following processing according to the number of acquired data sets.

The control unit 62 of the information processing device 6 derives distance image information on the basis of the acquired virtual endoscopic image or the like (S903). The control unit 62 derives the distance image information which is information regarding a distance between pixels in the virtual endoscopic image.

The control unit 62 of the information processing device 6 derives a feature parameter from the endoscopic image (S904). The control unit 62 of the information processing device 6 derives the feature parameter such as a region of the endoscopic image that is the target of the area correction processing, for example.

The control unit 62 of the information processing device 6 generates an endoscopic image whose feature parameter has been corrected on the basis of the distance image information (S905). The control unit 62 of the information processing device 6 corrects, for example, the area of the region corresponding to the feature parameter on the basis of the distance image information, and generates the endoscopic image whose feature parameter has been corrected.

The control unit 62 of the information processing device 6 inputs the endoscopic image whose feature parameter has been corrected to the learning model 9 (S906). Information input to the learning model 9 may include an effective mass number (effective-Z) and a body composition attached to a pixel of a three-dimensional medical image corresponding to the feature parameter in addition to the endoscopic image whose feature parameter has been corrected. The feature parameter corresponds to a region of the endoscopic image, that is, an intracorporeal site or pixel included in the endoscopic image, and the intracorporeal site or pixel corresponds to coordinates on and a pixel of the three-dimensional medical image by the distance image information generated from the virtual endoscopic image. As described above, since the effective mass number (effective-Z), the body composition, or both of them are attached to the pixel of the three-dimensional medical image, the control unit 62 acquires the effective mass number (effective-Z) and the body composition attached to the three-dimensional medical image on the basis of the endoscopic image whose feature parameter has been corrected.

The learning model 9 is trained to output diagnosis support information regarding a lesion included in the endoscopic image by inputting the endoscopic image whose feature parameter has been corrected, the effective mass number (effective-Z), and the body composition. By inputting the endoscopic image whose feature parameter has been corrected, the effective mass number (effective-Z), and the body composition to the learning model 9 trained in this manner, more accurate diagnosis support information can be acquired.

The control unit 62 of the information processing device 6 acquires the diagnosis support information output by the learning model 9 (S907). The control unit 62 of the information processing device 6 outputs the acquired diagnosis support information and the endoscopic image in association with each other (S908). The control unit 62 may output the acquired diagnosis support information, the endoscopic image, the three-dimensional medical image, the virtual endoscopic image, and information related to the endoscopic image such as the viewpoint position to the display unit 7 and may cause the display unit 7 to display them. Furthermore, the control unit 62 may register, in the endoscopic image DB 631, the acquired diagnosis support information and the endoscopic image in association with each other.

In the present embodiment, the respective functional parts in a series of processing including the learning model 9 have been described separately as a functional part of a control unit 121 of a processor 120 for an endoscope and a functional part of the control unit 62 of the information processing device 6, but the sharing of these functional parts is an example and is not limited thereto. Similarly to the fifth embodiment, the control unit 121 of the processor 120 for an endoscope may function as all functional parts of the control unit 62 of the information processing device 6. Alternatively, the control unit 121 of the processor 120 for an endoscope and the control unit 62 of the information processing device 6 may function as respective functional parts in a series of processing in cooperation by performing inter-process communication, for example.

According to the present embodiment, since a series of processing of performing endoscopic image correction by using the endoscopic image and the virtual endoscopic image already registered in the endoscopic image DB 631 and inputting the corrected endoscopic image to the learning model 9 is continuously performed, the diagnosis support information including the presence or absence of a lesion and the like output by the learning model 9 can be efficiently acquired. Since the diagnosis support information including the presence or absence of a lesion and the like output by the learning model 9 is registered in the endoscopic image DB 631 as a target of the diagnosis support information, the diagnosis support information output by the learning model 9 can be efficiently reused.

According to the present disclosure, the diagnosis support information with remarkably high accuracy can be obtained by using the endoscopic image and the virtual endoscopic image in combination. According to the present disclosure, the diagnosis support information obtained from the image feature parameter (feature amount) can be effectively used for diagnosis, the image feature parameter being obtained by combining the distance image obtained from the virtual endoscopic image that matches the endoscopic image, and the endoscopic image. According to the present disclosure, it is possible to provide a program or the like that efficiently associates the endoscopic image with the three-dimensional medical image.

The embodiments disclosed this time should be considered to be exemplary in all respects without being limited. The technical features described in the respective embodiments can be combined with each other, and the scope of the present invention is intended to include all modifications within the scope of the claims and the scope equivalent to the claims.

REFERENCE SIGNS LIST

1 Endoscope
11 Image sensor
12 Treatment tool insertion channel
13 Operation unit
14 Connector
15 Flexible tube
15a Arrow
151 Outer surface of endoscope 152 Inner surface of endoscope
153 Flexible body
16 Optical sensor
17 Optical sensor cable
2 Processor for endoscope (processor)
20 Sensor signal input unit
21 Control unit
22 Storage unit
23 Operation input unit
24 Output unit
25 Light source control unit
26 Communication unit
27 Light source
28 Reading unit
29 Large-capacity storage unit
291 Diagnosis support information DB
292 Image recognition model
2a Portable storage medium
2b Semiconductor memory
2P Control program
3 Display device
4 Information processing device (server)
41 Control unit
42 Storage unit
43 Communication unit
44 Input unit
45 Display unit
46 Reading unit
47 Large-capacity storage unit
471 Medical image DB
4a Portable storage medium
4b Semiconductor memory
4P Control program
20a Endoscopic image acquisition unit
20b Virtual endoscopic image acquisition unit
20c Virtual endoscopic image reconstruction unit
20d Diagnosis support information output unit
20e Distance image reconstruction unit
20f First correction unit
20g Second correction unit
20h Bending history information acquisition unit
20i Z coordinate correction unit
20j Z coordinate acquisition unit
S Diagnosis support system
110 Endoscope device
115 Keyboard
116 Storage shelf
120 Processor for endoscope
121 Control unit
1211 Image processing unit
122 Main storage device
123 Auxiliary storage device
124 Communication unit
125 Touch panel
126 Display device I/F
127 Input device I/F
128 Reading unit
131 Endoscope connector
1311 Electric connector
1312 Optical connector
133 Light source
134 Pump
135 Water supply tank
136 Air/water supply port
140 Endoscope
143 Operation unit
1431 Control button
1433 Bending knob
144 Insertion portion (flexible tube)
1441 Soft portion
1442 Bent portion
1443 Distal tip portion
1444 Image capturing unit
1445 Image sensor
1446 Image capturing light source
145 Bend preventing portion
148 Scope connector
149 Universal cord
50 Display device
6 Information processing device
61 Communication unit
62 Control unit
621 Acquisition unit
622 Viewpoint position deriving unit
623 Virtual endoscopic image generation unit
624 Matching degree determination unit
625 DB registration unit
626 Distance image information deriving unit
627 Feature parameter deriving unit
628 Feature parameter correction unit
629 Output unit
63 Storage unit
631 Endoscopic image DB
632 Recording medium
P Program
64 Input/output I/F
7 Display unit
70 Endoscopic image selection screen
71 Integrated image display screen
711 Viewpoint position field
712 Viewpoint direction field
713 Thumbnail display field
714 Display option field
715 Display mode switching field
8 Input unit
9 Learning model

The invention claimed is:

1. A device for converting a signal from an endoscope into an image comprising:
a processor configured to
acquire an endoscopic image of a patient from the endoscope via a signal transmitted from the endoscope to the processor;
acquire a virtual endoscopic image reconstructed on the basis of a three-dimensional medical image obtained by capturing an image of the patient in advance;
reconstruct a corrected virtual endoscopic image that matches most with the endoscopic image on the basis of a degree of matching between the acquired virtual endoscopic image and the acquired endoscopic image; and
output to a display diagnosis support information based on a feature parameter corrected according to a correspondence between each pixel of the acquired endoscopic image and a distance image obtained from the reconstructed virtual endoscopic image, wherein
the display displays in words whether the endoscopic image shows the presence or absence of a lesion on a first screen in response to receiving the diagnosis support information output from the processor, and
the display displays in words the effective mass number of a selected pixel of the virtual endoscopic image on the first screen that also displays in words whether the endoscopic image shows the presence or absence of a lesion in response to receiving the diagnosis support information output from the processor.

2. The device according to claim 1, wherein the processor is further configured to:
   measure an insertion distance of the endoscope inserted into a body of the patient;
   acquire bending history information of the endoscope; and
   correct a Z coordinate, which is the insertion distance of the endoscope, a viewpoint direction, and a viewpoint position of a virtual endoscope according to the acquired bending history information.

3. The device according to claim 1, wherein the processor is further configured to:
   reconstruct the distance image on the basis of the virtual endoscopic image; and
   correct a pixel value of each pixel of the corresponding endoscopic image according to a distance obtained from the distance image on the basis of the reconstructed distance image.

4. The device according to claim 3, wherein the processor is further configured to correct the feature parameter of each image region of the corresponding endoscopic image on the basis of the reconstructed distance image.

5. The device according to claim 4, wherein the processor is further configured to output the diagnosis support information including a tumor candidate on the basis of the corrected pixel value of each pixel or the corrected feature parameter.

6. The device according to claim 4, wherein the processor is further configured to output a recognition result by using a trained image recognition model that outputs the recognition result in a case where the corrected endoscopic image corrected on the basis of the corrected pixel value of each pixel or the corrected feature parameter is input.

7. The device according to claim 1, wherein the display displays in words whether the endoscopic image shows the presence or absence of a lesion, in association with the display of the endoscopic image in response to receiving the diagnosis support information output from the processor.

8. The device according to claim 1, wherein the display displays, in addition to the words indicating the presence or absence of a lesion, the stage of a symptom of the patient in response to receiving the diagnosis support information output from the processor.

9. The device according to claim 1, wherein the display displays information in
   a management ID column,
   a patient ID column,
   a diagnosis content column, and
   a diagnosis date and time column, in response to receiving the diagnosis support information output from the processor.

10. A device for converting a signal from an endoscope into an image comprising:
    a processor configured to
       acquire an endoscopic image of a patient from the endoscope via a signal transmitted from the endoscope to the processor;
       acquire a virtual endoscopic image reconstructed on the basis of a three-dimensional medical image obtained by capturing an image of the patient in advance;
       reconstruct a corrected virtual endoscopic image that matches most with the endoscopic image on the basis of a degree of matching between the acquired virtual endoscopic image and the acquired endoscopic image;
       output to a display diagnosis support information based on a feature parameter corrected according to a correspondence between each pixel of the acquired endoscopic image and a distance image obtained from the reconstructed virtual endoscopic, wherein the display displays in words whether the endoscopic image shows the presence or absence of a lesion in response to receiving the diagnosis support information output from the processor;
       reconstruct the distance image on the basis of the virtual endoscopic image;
       correct a pixel value of each pixel of the corresponding endoscopic image according to a distance obtained from the distance image on the basis of the reconstructed distance image; and
       correct the feature parameter of each image region of the corresponding endoscopic image on the basis of the reconstructed distance image, wherein
    the display outputs, in response to receiving the diagnosis support information output from the processor, a recognition result by using a trained image recognition model that outputs the recognition result in a case where the corrected endoscopic image corrected on the basis of the corrected pixel value of each pixel of the corresponding endoscopic image or on the basis of the corrected feature parameter is input, and
    the processor is further configured to output AI diagnosis support information using AI to output the recognition result.

* * * * *